(12) United States Patent
Baldwin et al.

(10) Patent No.: US 11,612,551 B2
(45) Date of Patent: *Mar. 28, 2023

(54) WHIPPED FORMULATIONS

(71) Applicants: FORMULATED SOLUTIONS, LLC, Largo, FL (US); BEIERSDORF AG, Hamburg (DE)

(72) Inventors: Stephen Baldwin, Flanders, NJ (US); Scott Carpenter, Palm Harbor, FL (US); Heidi Graham, Charlottesville, VA (US); Nanhye Kim, New Providence, NJ (US); Tom Meyer, Germantown, TN (US); David Reynolds, Ooltewah, TN (US); Jerry Vancleave, Lakeland, TN (US); Eric Dann, Safety Harbor, FL (US); Thomas Dann, Palm Harbor, FL (US); Renee Nelson, Brandon, FL (US); Brian Dann, Clearwater, FL (US)

(73) Assignees: FORMULATED SOLUTIONS, LLC, Largo, FL (US); BEIERSDORF AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/300,289

(22) PCT Filed: May 11, 2017

(86) PCT No.: PCT/US2017/032278
§ 371 (c)(1),
(2) Date: Nov. 9, 2018

(87) PCT Pub. No.: WO2017/197194
PCT Pub. Date: Nov. 16, 2017

(65) Prior Publication Data
US 2019/0282464 A1 Sep. 19, 2019

Related U.S. Application Data

(60) Provisional application No. 62/334,862, filed on May 11, 2016, provisional application No. 62/351,385, (Continued)

(51) Int. Cl.
| | |
|---|---|
| A61K 8/04 | (2006.01) |
| A61K 8/27 | (2006.01) |
| A61Q 17/04 | (2006.01) |
| A61Q 19/00 | (2006.01) |
| A61K 8/19 | (2006.01) |
| A61Q 7/00 | (2006.01) |
| B65D 83/14 | (2006.01) |
| A61Q 11/00 | (2006.01) |
| A23P 30/40 | (2016.01) |
| A61K 9/12 | (2006.01) |
| A61Q 5/06 | (2006.01) |

(Continued)

(52) U.S. Cl.
CPC .............. *A61K 8/046* (2013.01); *A23P 30/40* (2016.08); *A61K 8/19* (2013.01); *A61K 8/27* (2013.01); *A61K 9/122* (2013.01); *A61Q 5/06* (2013.01); *A61Q 7/00* (2013.01); *A61Q 11/00* (2013.01); *A61Q 17/04* (2013.01); *A61Q 19/00* (2013.01); *A61Q 19/004* (2013.01); *B65D 83/207* (2013.01); *B65D 83/62* (2013.01); *B65D 83/752* (2013.01); *A61K 2800/22* (2013.01); *A61K 2800/87* (2013.01)

(58) Field of Classification Search
CPC .......... A61K 8/046; A61K 9/122; A61K 8/27; A61K 8/19; A61K 2800/22; A61K 2800/87; B65D 83/207; B65D 83/62; B65D 83/752; A61Q 7/00; A61Q 11/00; A61Q 19/004; A61Q 5/06; A61Q 17/04; A61Q 19/00; A23P 30/40; A61P 17/02
See application file for complete search history.

(56) References Cited

U.S. PATENT DOCUMENTS

| | | |
|---|---|---|
| 3,395,215 A | 7/1968 | Schubert et al. |
| 3,710,538 A | 1/1973 | Lowy |

(Continued)

FOREIGN PATENT DOCUMENTS

| | | |
|---|---|---|
| AU | 2017263531 A1 | 10/2018 |
| AU | 2017263533 A1 | 10/2018 |

(Continued)

OTHER PUBLICATIONS

English translation of Blatt et al. (EP 2319586 A1) (Year: 2011).*
Office Action received in U.S. Appl. No. 16/300,323, filed Jun. 12, 2020, 17 pages.
International Search Report and Written Opinion received in PCT/US2017/032292 dated Jul. 26, 2017, pp. 10.
International Preliminary Report received in PCT/US2017/032292 dated Nov. 13, 2018, pp. 7.

(Continued)

*Primary Examiner* — Robert A Wax
*Assistant Examiner* — Quanglong N Truong
(74) *Attorney, Agent, or Firm* — Liang & Hennessey LLP; Stanley D. Liang

(57) ABSTRACT

The present disclosure relates to, inter alia, a formulation in a package, the formulation comprises one or more active agents and is co-mingled with a whipping agent prior to being filled under pressure into the package. The whipping agent is added in sufficient amounts to be dispersed in the formulation. The pressurized package is under sufficient pressure suitable to maintain the whipping agent dispersed in the formulation; and the pressurized package is under sufficient pressure to expel the formulation as a whipped formulation upon application of external force on the formulation in the package.

14 Claims, 44 Drawing Sheets

Related U.S. Application Data filed on Jun. 17, 2016, provisional application No. 62/396,415, filed on Sep. 19, 2016, provisional application No. 62/396,424, filed on Sep. 19, 2016.

(51) Int. Cl.
  *B65D 83/20* (2006.01)
  *B65D 83/62* (2006.01)

(56) References Cited

U.S. PATENT DOCUMENTS

| | | |
|---|---|---|
| 3,970,584 A | 7/1976 | Hart et al. |
| 4,670,272 A | 6/1987 | Chen et al. |
| 5,104,987 A | 4/1992 | King |
| 5,214,925 A | 6/1993 | Hoy et al. |
| 5,560,859 A | 10/1996 | Hartmann et al. |
| 5,858,343 A | 1/1999 | Szymczak |
| 6,322,776 B1 | 11/2001 | Ortega |
| 2004/0052826 A1 | 3/2004 | Fernandez-Kleinlein et al. |
| 2004/0197270 A1 | 10/2004 | Mundschenk |
| 2004/0241099 A1 | 12/2004 | Popp et al. |
| 2004/0247534 A1 | 12/2004 | Stoltz |
| 2004/0258627 A1 | 12/2004 | Riedel et al. |
| 2004/0258628 A1 | 12/2004 | Riedel et al. |
| 2005/0079142 A1 | 4/2005 | Brunckhorst et al. |
| 2008/0138296 A1 | 6/2008 | Tamarkin et al. |
| 2008/0253973 A1 | 10/2008 | Tamarkin et al. |
| 2008/0260655 A1 | 10/2008 | Tamarkin et al. |
| 2011/0281827 A1 | 11/2011 | Tamarkin et al. |
| 2012/0087872 A1 | 4/2012 | Tamarkin et al. |
| 2012/0213712 A1 | 8/2012 | Kasai et al. |
| 2012/0288462 A1 | 11/2012 | Lebok et al. |
| 2012/0288465 A1 | 11/2012 | Loechel |
| 2012/0301422 A1 | 11/2012 | Meyer |
| 2013/0011341 A1 | 1/2013 | Nguyen et al. |
| 2013/0233310 A1 | 9/2013 | Hilgers et al. |
| 2014/0079648 A1 | 3/2014 | Cohen |
| 2014/0120039 A1 | 5/2014 | Baldwin et al. |
| 2014/0131395 A1 | 5/2014 | Chang |
| 2016/0101051 A1 | 4/2016 | Tamarkin et al. |
| 2016/0202051 A1 | 7/2016 | Heist et al. |
| 2019/0142709 A1 | 5/2019 | Baldwin et al. |
| 2019/0151207 A1 | 5/2019 | Baldwin et al. |
| 2019/0282463 A1 | 9/2019 | Baldwin et al. |
| 2019/0367256 A1 | 12/2019 | Baldwin et al. |

FOREIGN PATENT DOCUMENTS

| | | | |
|---|---|---|---|
| CN | 1217650 A | 5/1999 | |
| CN | 1713891 A | 12/2005 | |
| CN | 103547247 A | 1/2014 | |
| CN | 110035737 A | 7/2019 | |
| DE | 10229812 A1 | 1/2004 | |
| DE | 10304721 A1 | 8/2004 | |
| EP | 1391192 A1 | 2/2004 | |
| EP | 1508326 A1 | 2/2005 | |
| EP | 2319586 A1 | 5/2011 | |
| EP | 2636401 A1 | 9/2013 | |
| EP | 3454662 A1 | 3/2019 | |
| EP | 3454826 A1 | 3/2019 | |
| EP | 3454946 A1 | 3/2019 | |
| EP | 3454949 A1 | 3/2019 | |
| ES | 2560540 T3 | 2/2016 | |
| JP | H3131680 | 6/1991 | |
| JP | H0625051 B2 | 2/1994 | |
| WO | 0103663 A1 | 1/2001 | |
| WO | 2004022019 A1 | 3/2004 | |
| WO | 2005007516 A2 | 1/2005 | |
| WO | 2012154918 A2 | 11/2012 | |
| WO | 2017112727 A1 | 6/2017 | |
| WO | 2017197193 A1 | 11/2017 | |
| WO | 2017197194 A1 | 11/2017 | |
| WO | 2017197195 A1 | 11/2017 | |
| WO | 2017197196 A1 | 11/2017 | |
| WO | 2017197202 A1 | 11/2017 | |

OTHER PUBLICATIONS

Aurena Laboratories "SunScreen Bag on Valve", Retrieved from the Internet, Nov. 19, 2014, pgs.
International Search Report and Written Opinion received in PCT/US2017/032277 dated Aug. 1, 2017, pp. 15.
International Preliminary Report received in PCT/US2017/032277 dated Nov. 13, 2018, pp. 10.
International Search Report and Written Opinion received in PCT/US2017/032278 dated Jul. 26, 2017, pp. 9.
International Preliminary Report received in PCT/US2017/032278 dated Nov. 13, 2018, pp. 6.
Mintel, "Hair Styling Foam", Oct. 2013, XP002772098, Online.
Mintel, "Pack Facial Mask", Mar. 2016, XP002772099, Online.
Mintel, "Body Whip Moisture Cream", Jul. 2008, XP002772100, Online.
Mintel, "Body Whip Cream", Aug. 2009, XP002772101, Online.
International Search Report and Written Opinion received in PCT/US2017/032279 dated Jul. 28, 2017, pp. 11.
International Preliminary Report received in PCT/US2017/032279 dated Nov. 13, 2018, pp. 8.
International Search Report and Written Opinion received in PCT/US2017/032281 dated Aug. 1, 2017, pp. 16.
International Preliminary Report received in PCT/US2017/032281 dated Nov. 13, 2018, pp. 11.
Mexican Patent Office, Mexican Official Action for Mexican App. No. MX/a/2018/013754 (dated Jun. 22, 2021), pp. 1-6.
USPTO, Non-Final Rejection of the U.S. Exam Report for U.S. Appl. No. 16/300,342 (dated Jun. 24, 2021), pp. 1-13.
Dailymed, "Coppertone Defend and Care Oil Free Lotion SPF 30," www.dailymed.nim.nih.gov. Published online Dec. 17, 2015, pp. 1-3.
Australia IP, Examination report No. 1 for standard patent application for Australian App. No. 2017263538 (dated Feb. 25, 2021).
USPTO, Non-Final Rejection of the U.S. Exam Report for U.S. Appl. No. 16/300,270 (dated Jul. 23, 2020).
USPTO, Non-Final Rejection of the U.S. Exam Report on U.S. Appl. No. 16/300,245 (dated Feb. 5, 2021).
CIPO, Examination Report and Examination Search Report for Canadian App. No. 3,023,714 (dated Mar. 1, 2021).
EPO, Communication pursuant to Article 94(3) EPC for European App. No. 17726753.1.
Australia IP, Examination report No. 1 for standard patent application for Australian App. No. 2017263531 (dated Feb. 25, 2021).
USPTO, Non-Final Rejection of the U.S. Exam Report on U.S. Appl. No. 16/300,245 (dated Jul. 23, 2020).
USPTO, Final Rejection of the U.S. Exam Report on U.S. Appl. No. 16/300,323 (dated Nov. 18, 2020).
CIPO, Examination Report and Examination Search Report for Canadian App. No. 3,023,669 (dated Jan. 29, 2021).
Australia IP, Examination report No. 1 for standard patent application for Australian App. No. 2017263532 (dated Feb. 25, 2021).
CIPO Examination Report and Examination Search Report for Canadian App. No. 3,023,680 (dated Feb. 17, 2021).
EPO, Communication pursuant to Article 94(3) EPC for European App. No. 17725450.5 (dated Mar. 19, 2021).
Australia IP, Examination report No. 1 for standard patent application for Australian App. No. 2017263533 (dated Feb. 25, 2021).
CIPO, Examination Report and Examination Search Report for Canadian App. No. 3,023,702 (dated Feb. 1, 2021).
EPO, Communication pursuant to Article 94(3) EPC for European App. No. 17726754.9 (dated Feb. 23, 2021).
Australia IP, Examination report No. 1 for standard patent application for Australian App. No. 2017263534 (dated Feb. 25, 2021).
USPTO, Non-Final Rejection of the U.S. Exam Report on U.S. Appl. No. 16/300,342 (dated Jul. 8, 2020).
CIPO, Examination Report and Examination Search Report for Canadian App. No. 3,023,703 (dated Feb. 12, 2021).
EPO, Communication pursuant to Article 94(3) EPC for European App. No. 17726162.5 (dated Apr. 2, 2021).
EPO, Communication pursuant to Article 94(3) EPC for European App. No. 17725453.9 (dated Mar. 19, 2021).
USPTO, Final Rejection of the U.S. Exam Report on U.S. Appl. No. 16/300,342 (dated Dec. 11, 2020).

(56) References Cited

OTHER PUBLICATIONS

USPTO, Non-Final Rejection of the U.S. Exam Report on U.S. Appl. No. 16/300,323 (dated Jun. 12, 2020).
USPTO, Non-Final Rejection of the U.S. Exam Report on U.S. Appl. No. 16/300,270 (dated Feb. 5, 2021).
Food Crumbles, The Science of Foams in Food, Apr. 5, 2020, https://foodcrumbles.com/science-of-foams-in-food (Year 2020), 14 pgs.
BPO, Brazilian Office Action received in Brazilian Application No. BR112018073118-8 dated Nov. 8, 2021, 4 pages.
Chinese Office Action received in Chinese Application No. 201780028415.1 dated Dec. 6, 2021, pp. 14.
Chinese Office Action received in Chinese Application No. 201780028486.1 dated Nov. 8, 2021, pp. 12.
USPTO, Non-Final Rejection of the U.S. Exam Report for U.S. Appl. No. 16/300,342 (dated Aug. 10, 2022).
Chinese Office Action received in 201880031248.0, dated Apr. 18, 2022, pp. 6.
Zhang et al., "Nonionic Surfactant Application Patent Technology," China Light Industry Press, Mar. 31, 2001, pp. 1-2.
Chinese National Intellectual Property Administration, Chinese Second Office Action for App. No. 201780028415.1 (dated Sep. 5, 2022), pp. 1-17.
USPTO, Non-Final Rejection of the U.S. Exam Report on U.S. Appl. No. 16/300,323 (dated Feb. 8, 2023), 19 pages.

\* cited by examiner

Results for Evaluation of Whipped Zinc Oxide (10% w/w) Cream

| Whippability | Spreadability and Texture of Resultant Whipped-foams | Stability of Whipped-foams at RT | |
| --- | --- | --- | --- |
| | | Initial (T=0) | T=10 Minutes |
| Yes | 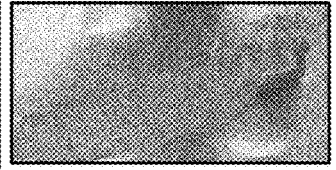 Soft / Smooth Texture Spread Easily |  |  |

FIG. 1

Results for Evaluation of Whipped Zinc Oxide (40% w/w) Ointment

| Whippability | Spreadability and Texture of Resultant Whipped-foams Product | Stability of Whipped-foams at RT | |
| --- | --- | --- | --- |
| | | Initial (T=0) | T=10 Minutes |
| Yes |  Soft / Smooth Texture Spread Easily |  |  |

FIG. 2

Appearance and Stability of "Whipped-foam" Delivered from Whipped Zinc Oxide Products Stored at 50°c/75%RH for 1 Day.
| | Whipped Zinc Oxide (ZnO) Products | |
| --- | --- | --- |
| | 10% w/w ZnO Cream | 40% w/w ZnO Ointment |
| "Whipped-foam" Dispensed After Storage At 50°c, 1 Day and then Allowed to Cool to RT. | 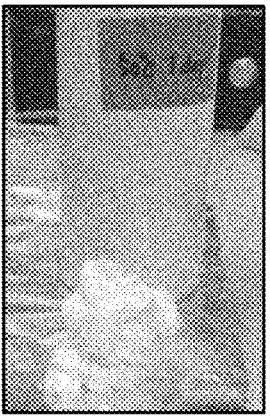 | 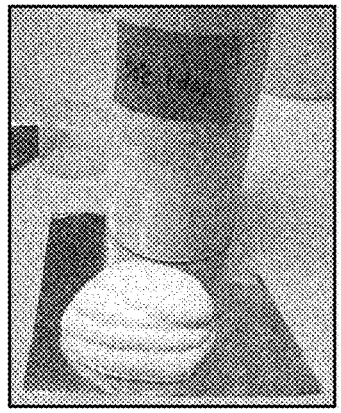 |
FIG. 3

| Run No. | Cut-bag pressure (psi) | Product density (g/L) | Initial | After 20 minutes at RT |
|---|---|---|---|---|
| 1 | 20 | 50 | 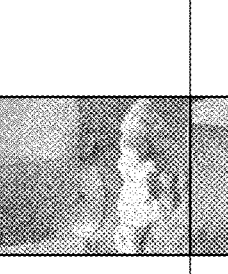 | 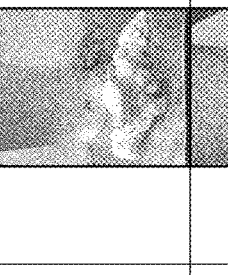 |
|  |  | 125 | 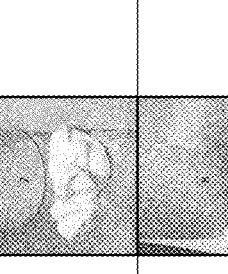 | 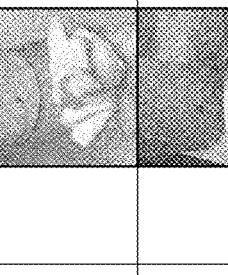 |
|  |  | 200 |  | 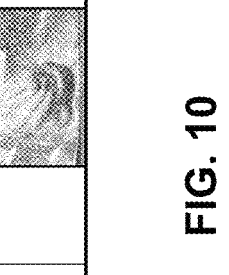 |
FIG. 10

| Run No. | Cut-bag pressure (psi) | Product density (g/L) | Initial | After 20 minutes at RT |
|---|---|---|---|---|
| 1 | 45 | 50 |  |  |
|  |  | 125 | 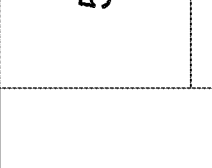 | 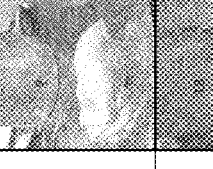 |
|  |  | 200 | 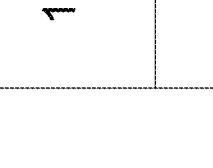 |  |
FIG. 12

| Run No. | Cut-bag pressure (psi) | Product density (g/L) | Initial | After 20 minutes at RT |
|---|---|---|---|---|
| 1 | 20 | 50 | | |
| | | 125 | | |
| | | 200 | | |

FIG. 13

| Run No. | Cut-bag pressure (psi) | Product density (g/L) | Initial | After 20 minutes at RT |
|---|---|---|---|---|
| 1 | 32.5 | 50 | | |
| | | 125 | | |
| | | 200 | | |

FIG. 14

| Run No. | Cut-bag pressure (psi) | Product density (g/L) | Initial | After 20 minutes at RT |
|---|---|---|---|---|
| 1 | 45 | 50 | | |
| | | 125 | | |
| | | 200 | | |

| Run No. | Cut-bag pressure (psi) | Product density (g/L) | "Whipped-foam" dispensed at T=0* | "Whipped-foam" dispensed after T=2 min. at RT |
|---|---|---|---|---|
| 1 | 20 | 50 |  |  |
|  |  | 125 |  |  |
|  |  | 200 |  |  |
FIG. 19

| Run No. | Cut-bag pressure (psi) | Product density (g/L) | Initial | After 20 minutes at RT |
|---|---|---|---|---|
| 1 | 20 | 50 | 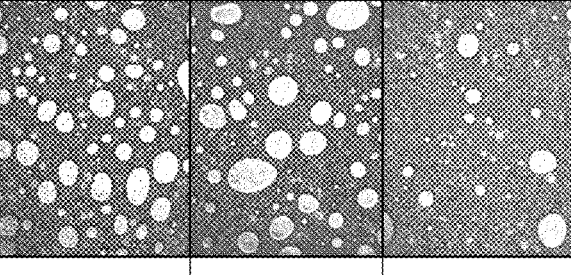 | 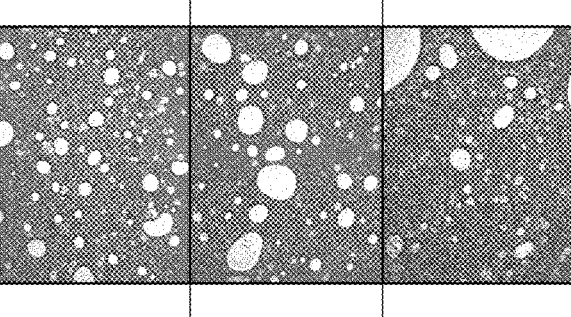 |
| | | 125 | | |
| | | 200 | | |
FIG. 22

| Run No. | Cut-bag pressure (psi) | Product density (g/L) | Initial | After 20 minutes at RT |
|---|---|---|---|---|
| 1 | 32.5 | 50 | | |
| | | 125 | | |
| | | 200 | | |

FIG. 23

| Run No. | Cut-bag pressure (psi) | Product density (g/L) | Initial | After 20 minutes at RT |
|---|---|---|---|---|
| 1 | 45 | 50 | | |
| | | 125 | | |
| | | 200 | | |

FIG. 24

WHIPPED FORMULATIONS

TECHNICAL FIELD

This invention relates to the field of whipped or whippable formulations. More specifically, the invention relates to whipped or whippable formulations, such as for topical application, such as, for example, skincare products.

BACKGROUND

High viscosity and high solids products are often found to be difficult to distribute on the skin or a secondary surface and selection of an appropriate amount of product can often be difficult for a user to estimate.

Also, a key factor for ensuring the effectiveness of a formulation, such as skincare (such as, for example, diaper rash products), sunscreen, vitamins for oral administration, woundcare for animals or humans, whip cream, haircare, medical hair & scalp treatments, topical analgesics, skin protection, etc. is end-user compliance and satisfaction.

Ideally, the skincare formulation should be easily applied to the skin of the user, and have a good texture and "feel" on the skin of the users.

Likewise, other products, such as for suncare, vitamins for oral administration, woundcare for animals or humans, whip cream, for haircare, for medical hair & scalp treatments, for topical analgesics, for skin protection, etc. could benefit from being administered as a whipped product, without the possibility of abuse.

SUMMARY

This disclosure provides a formulation in a package, which may be pressurized. The formulation comprises one or more skincare active agents and is co-mingled (co-processed) with a whipping agent (e.g., a gas propellant; a first gas propellant) prior to being filled under pressure into the package. The first propellant is added in sufficient amounts to be dispersed in the formulation. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the package comprises a pressure generating and maintaining component. In certain embodiments, the component comprises one or more (second) gas and/or liquid propellants. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the one or more gas and/or liquid propellants do not co-mingle with the formulation.

In other aspects, this disclosure provides a method of preparing a whippable formulation, comprising: filling a formulation comprising one or more skincare active agents co-mingled (co-processed) with a whipping agent (e.g., a gas propellant; a first gas propellant) under pressure into a package; wherein the whipping agent is added in sufficient amounts to be dispersed in the formulation. In certain embodiments, the package is under sufficient pressure suitable to maintain the whipping agent dispersed in the formulation. In certain embodiments, the pressurized package is under sufficient pressure to expel the formulation as a whipped formulation upon application of external force on the formulation in the package. In certain embodiment, the method is performed under controlled temperature. In certain embodiments, the package maintains at least a minimal amount of pressure until substantially all the formulation in the package is expelled as a whipped formulation. In certain embodiments, the package comprises a pressure generating and maintaining component. In certain embodiments, the component comprises one or more (second) gas and/or liquid propellants. In certain embodiments, the pressure generating and maintaining component is present in the package in sufficient amounts and pressure to expel the formulation as a whipped formulation upon application of external force on the formulation in the package. In certain embodiments, the one or more gas and/or liquid propellants do not co-mingle with the formulation.

In other aspects, this disclosure provides a method of using a formulation that is a whipped formulation product disclosed herein, comprising administering the formulation to a subject in need thereof.

In other aspects, this disclosure provides a package comprising the formulation disclosed herein.

Numerous other aspects are provided in accordance with these and other aspects of the invention. Other features and aspects of the present invention will become more fully apparent from the following detailed description and the appended claims.

BRIEF DESCRIPTION OF THE DRAWINGS

FIG. 1 shows results for evaluation of whipped zinc oxide (10% w/w) cream.

FIG. 2 shows results for evaluation of whipped zinc Oxide (40% w/w) ointment.

FIG. 3 shows appearance and stability of "Whipped-Foam" delivered from whipped zinc oxide products stored at 50° C./75% RH for 1 day.

DETAILED DESCRIPTION

Figure 4:
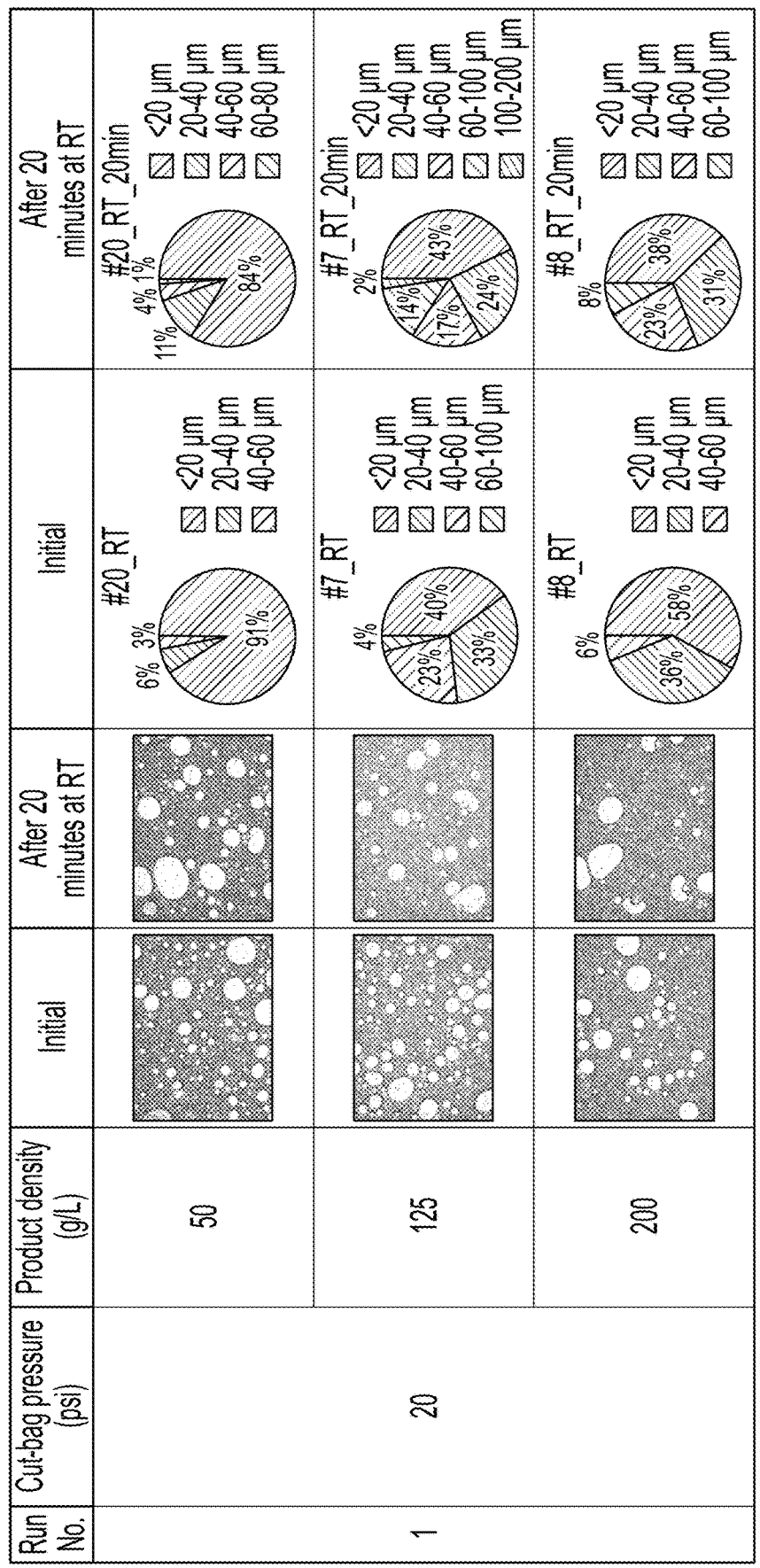
FIG. 4 shows results of bubble size and distribution at various product densities and at 20 psi cut-bag pressure.

As used herein, the word "a" or "plurality" before a noun represents one or more of the particular noun. For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

This disclosure provides a formulation in a package, which may be pressurized. The formulation comprises one or more skincare active agents and is co-mingled (co-processed) with a whipping agent (e.g., a gas propellant; a first gas propellant) prior to being filled under pressure (and in certain embodiments under controlled temperature) into the package. The whipping agent is added in sufficient amounts to be dispersed in the formulation. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the package comprises a pressure generating and maintaining component. In certain embodiments, the component comprises one or more (second) gas and/or liquid propellants. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the one or more as and/or liquid propellants do not co-mingle with the formulation. In certain embodiments, one of the one or more skincare active agents is a solid ingredient or a high viscosity ingredient. In certain embodiments, the formulation comprises less than 20% water.

No UV filter substances are used for the foam-boosting of self-foaming.

The disclosed whipped formulation may be referred to herein as whipped formulation, whipped formulation product, whipped product, and the like.

The disclosed whippable formulation may be referred to herein as whippable formulation, whippable formulation product, whippable product, and the like.

A whipped formulation is at one time a whippable formulation.

The term "can" may be used to also mean "package."

A subject may be a human subject (user) or may be an animal subject (user). The terms "subject" and "user" are used interchangeably.

In other aspects, this disclosure provides a method of preparing a whippable formulation, comprising: filling a formulation comprising one or more skincare active agents co-mingled (co-processed) with a whipping agent (e.g., a gas propellant; a first gas propellant) under pressure into a package, which may be pressurized; wherein the whipping agent is added in sufficient amounts to be dispersed in the formulation. In certain embodiments, the package is under sufficient pressure suitable to maintain the whipping agent dispersed in the formulation. In certain embodiments, the package is under sufficient pressure to expel the formulation as a whipped formulation upon application of external force on the formulation in the package. In certain embodiments, the method is performed under controlled temperature. In certain embodiments, the package maintains at least a minimal amount of pressure until substantially all the formulation in the package is expelled as a whipped formulation. In certain embodiments, the package comprises a pressure generating and maintaining component. In certain embodiments, the component comprises one or more (second) gas and/or liquid propellants. In certain embodiments, the pressure generating and maintaining component is present in the package in sufficient amounts and pressure to expel the formulation as a whipped formulation upon application of external force on the formulation in the package. In certain embodiments, the one or more gas and/or liquid propellants do not co-mingle with the formulation. In certain embodiments, one of the one or more skincare active agents is a solid ingredient or a high viscosity ingredient. In certain embodiments, the formulation comprises less than 20% water.

In other aspects, this disclosure provides a method of using a formulation that is a whipped formulation product disclosed herein, comprising administering the formulation to a subject in need thereof.

In other aspects, this disclosure provides a package, which may be pressurized, comprising a whippable formulation. The formulation comprises one or more skincare active agents and is co-mingled (co-processed) with a whipping agent (e.g., a gas propellant; a first gas propellant) prior to being filled under pressure (and in certain embodiments under controlled temperature) into the package. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the package comprises a pressure generating and maintaining component. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the pressure generating and maintaining component comprises one or more (second) gas and/or liquid propellants. In certain embodiments, the one or more gas and/or liquid propellants do not co-mingle with the formulation. In certain embodiments, one of the one or more skincare active agents is a solid ingredient or a high viscosity ingredient. In certain embodiments, the formulation comprises less than 20% water.

In certain embodiments, the whipped formulation comprises a high concentration of a solid ingredient (i.e., high solids), a high viscosity ingredient, or both.

In certain embodiments, a solid ingredient is one that is not easily dissolved in water or another solvent. In certain embodiments, the solid ingredient includes, without limitation, zinc oxide, titanium dioxide, wax, inorganic clay, minerals, microcapsules and other solid particles, or a mixture thereof. In certain embodiments, the formulation comprises from about 10% to about 85% solids content (i.e., solid ingredient being from about 10% to about 85%). In certain embodiments, the formulation comprises from about 10% to about 60% solids content. In certain embodiments, the formulation comprises from about 10% to about 50% solids content. In certain embodiment, the solid ingredient may be up to and in excess of about 40%. In certain embodiments, the formulation comprises zinc oxide, such that the high solids content is up to or in excess of about 40%, about 50%, about 60%, about 85% etc.

In certain embodiments, a high viscosity ingredient has a viscosity of about 75,000-450,000 cps.

The whipped formulation comprising high solids or high viscosity ingredients may be a topical therapeutic skin care formulation. This formulation provides easily "spreadable", low drag application experience, with such an experience being highly desirable for the treatment of sensitive or damaged skin. Such formulation generally has a specific gravity in excess of 1. For example, the specific gravities may be about, or in excess of, 1.1-3; such as, for example, about 1.1, or about 1.4-1.5. These formulations can be improved through infusion of compressed gas, which in turn is held in a steady gas-infused super saturated state, until time of release into ambient conditions, at which time the formulation becomes "transformed" into a reduced density product form, through the expansion of highly compressed saturated gas.

The whipped formulation comprising high solids or high viscosity ingredients is effectively transformed from a paste into a reduced density gas emulsion with a multitude of gas microbubbles. These bubbles are continuously distributed through the whipped formulation and may express on the surface of the dispensed product as agglomerated bubbles, signaling to the consumer the uniqueness of the transformed formulation, further differentiating it from standard BOV dispensed products and further reinforcing the perception of a "light and airy" application experience. The density of the formulation may be reduced, lowering "pre-gas" or "cut-bag" pressures thus reducing finished can pressures (of the package) and may allow for lower pressurized can ratings to be leveraged, further reducing costs and technical requirements of the package. Certain first gas propellants, includes, without limitation, oxygen and carbon dioxide, may also be used to evoke various therapeutic and/or cosmetic skin care responses.

This transformed formulation also enables the use of "soft touch" secondary application tools, including, without limitation, sponges, brushes, and the like, further increasing the utility of the formulation by allowing the user to apply what would normally be a thick, viscous paste in a fashion more akin to a lower viscosity, lower drag cream in a "no touch" manner.

An additional benefit of this system is the described reduced viscosity transformation of the high solids formulation may help the user to better visually control the amount of product applied, while still permitting the creation of a highly occlusive coating. This is achieved as a result of the increased volume to mass product ratio created during dispensing.

In certain embodiments, the pressurized package is under sufficient pressure to expel the formulation upon application of external force on the formulation, either with a second gas and/or liquid propellant or mechanical force to generate enough pressure to keep the first gas microdispersed or in emulsion.

In certain embodiments, the disclosed formulations and methods allow for very high levels of inert gas dissolved into the product and effectively held under pressure in a gas-emulsion, preventing unwanted bubble agglomeration, providing for highly uniform product characteristics. The result is a rich, thick "whipped-cream-style" lotion that provides confidence of sunscreen coverage (in the case where the product is a sunscreen), while offering surprisingly fast "rub-in"; while not altering the inherent moisturization and protection properties of the otherwise thick, lipid-rich base formulation.

Whippable products include, in addition to for skincare and suncare (sunscreen and after sun care), for example and without limitation:

Category—Class—Whipped Benefit
Whip Cream—Food—Anti-Abuse
Peanut Butter—Food—Ease of Application
Dessert Topping—Food—Ease of Application
Topical Analgesic—OTC Drug—Improved Absorption
Burn Cream—Medical Device Rx—Reduced Spread-ability Pain
Medical Haircare/Hair loss—NDA—Reduced Consumer Complaints/Failure to empty
Medical Haircare/Scalp treatment—OTC Drug—Improved Delivery/Application
Petrolatum Gel—OTC Drug—Ease of Application
Hair Styling Product—Cosmetic—Novel Delivery of Thicker Products
Diaper Rash Prevention—OTC Drug—Novel Delivery of Thicker Products
Tooth Whitener—Cosmetic—Better Coverage
Oral Care/Toothpaste—Cosmetic—Improved Delivery
Anti-Fungal treatment—OTC/Rx Drug—Reduced Spread-ability Pain/Improved Absorption
Eye-lid Cleanser—Cosmetic—Novel Delivery
Psoriasis treatment—Medical Device—Reduced Spread-ability Pain
Colon-Rectal Treatment—Rx—Improved Drug Delivery and Absorption
Acne treatment—OTC Drug—Novel Delivery
Hand Sanitizer—OTC Drug—Formulation Approach
Natural Deodorant—Cosmetic—Improved Spread-ability
Shave Prep—Cosmetic—Novel Delivery of Thicker Products
Wound Care—Medical Device—Novel Delivery of Thicker Products
Self-Tanner—Cosmetic—Improved Delivery
Body Moisturizer—Cosmetic—Novel Delivery of Thicker Products
Lice Treatment—Medical Device/OTC—Novel Delivery of Thicker Products
Hair Depilatory—OTC Drug—Novel Delivery of Thicker Products
Whipped Vitamins (Children's & Adult's)—Nutritionals—Novel Delivery/Ease of Application
Topical Whipped Pet Heartworm/Flea & Tick Treatment—Animal Health—Novel Delivery/Ease of Application
Ingestible Whipped Pet Heartworm/Flea & Tick Treatment—Animal Health—Novel Delivery/Ease of Application
Anti-Hemorrhagic—Rx/Device—Formulation Compatibility/Non-Flammability/Surgical Application.

Thus, in certain embodiments, the formulation disclosed herein comprise one or more active agents for each of the above formulations.

In certain embodiments, the whipped formulation product is a skincare product, comprising one or more skincare active agents. In certain embodiments, the whipped formulation is a diaper rash product.

In certain embodiments, the whipped formulation comprises high solids (including zinc oxide), up to and in excess of about 85%.

A subject may be a human subject (user) or may be an animal subject (user). "Subject" and "user" are used interchangeably.

In certain embodiments, the formulation further comprises a foaming agent. In certain embodiments, the formulation is for topical application.

In certain embodiments, the pressurized package in which pressure may be generated and/or maintained sufficient for the disclosed formulations is a Bag-on-valve, Piston Can, or Bag-in-Can. In other embodiments, the pressurized package is a mechanical pressure system, including for example, bladder system (such as Exxal Atomos System), which is a PowerContainer system with a rubber bladder around the outside providing pressure to the internal volume.

In certain embodiments, the package is a bag on valve (BOV) pressurized assembly, comprising a two way fill/dispensing valve, an attached internal high barrier bag affixed to said valve, and rigid container capable of holding positive pressure, affixed to the valve. In certain further embodiments, the container is glass, barrier resin, metal/alloy, or another material capable of holding positive pressure. In certain other further embodiments, the container is pre-pressurized with one or more gas and/or liquid propellants prior to filling. In certain further embodiments, the BOV pressurized assembly dispenses the whipped product in a metered dispensing system and not a continuously dosing system.

In certain embodiments, pre-pressurizing the package is not needed. In certain embodiments, the package is under Zero Cut Bag Pressure, where gas is present around bag but not pressurized above ambient. Filling the package at ambient pressure, the pressure inside the package would increase as the BOV expands. In certain embodiments, the package comprises an elastomeric tube/bag (akin to a tied off surgical tube). In certain further embodiments, a slight vacuum is applied. In certain embodiments, the package is pressure agnostic, in which the container cannot hold pressure around the bag. In certain embodiments, the package has Negative Cut Bag Pressure, where vacuum is present around the bag but not pressurized above ambient. Other such systems may be used, such as the Sterilflo® system (https://www.hydrasense.ca/en/why-choose-hydrasense/steriflo/).

In certain embodiments, the pressurized package can comprise a "pressure generating and maintaining component," which may be a component that generates and/or maintains pressure in the package. It may refer to a chemical component or components which generate pressure, e.g., compressed gas, while inside an enclosed package, device or container (such as a can, for example). Non-limiting examples of such pressure generating and maintaining components are compressed gases/propellants and liquid propellants such as, for example, $CO_2$, propane, butane, isobutane, dimethyl ether, nitrous oxide, nitrogen, oxygen, air, isopentane, hydrofluroolefin, and the like, and suitable blends of such propellants. When a valve is opened by applying an external force, the formulation or ingredients in the device are dispensed in a 'whipped' form or a foamy form. This chemical component or components does not co-mingle with the formulation and may not be dispended with the whipped formulation.

A "skincare active agent" includes all those materials which are regarded as acceptable for use as active skin-protecting/treating ingredients. A skincare active agent includes, for example and without limitation, skin protectants, anti-inflammatory agents, antioxidants, topical anesthetics, antimycotics, keratolytics, and/or anti-aging agents. Approval by a regulatory agency may sometimes be required for inclusion of active agents in formulations intended for human contact including but not limited to zinc oxide for diaper rash treatments or petrolatum, white petrolatum, mineral oil, glycerin and dimethicone as skin protectants, ibuprofen, diclofenac, felbianc, ketoprofen, or piroxicam, as topical anti-inflammatories, lidocaine and its salt forms, and benzocaine and its salt forms as topical anesthetics, Imidazole, triazole, and thiazole antifungals (e.g., miconazole, clotrimazole, efinaconazole, and abafungin), terbinafine hydrochloride, tolnaftate as antimycotics, salicylic acid, urea, and lactic acid as keratolytics as well as agents used as self-tanners or sunscreen active ingredients and the like.

Other active agents are contemplated. These include, for example and without limitation, sunscreen active agents, after sun active agents, vitamins, food, etc. Any active agents that can be included as a whipped formulation or a whippable formulation are within the scope of this invention.

In certain embodiments, the package does not display any bearding. Bearding is leakage forced by continued expansion of product still contained within the flow channel of the actuator.

In certain embodiments, the formulation is characterized by microdispersion. In certain embodiments, the formulation is characterized by substantially consistent microvoid after the formulation is expelled from the package. In certain embodiments, the formulation is highly emollient after the formulation is expelled from the package. In certain embodiments, the formulation is readily spreadable and spread evenly after the formulation is expelled from the package.

In certain embodiments, the whipping agent is an aerosol propellant (including hydrocarbon propellant, compressed gas propellant, soluble gas propellant, and liquefied gas propellant) or a liquid propellant.

In certain embodiments, the whipping agent is a gas propellant. The gas propellant is, for example and without limitation, nitrogen, nitrous oxide, carbon dioxide, Argon, air or oxygen. In certain embodiments, the gas propellant in the formulation is between about 0.01% w/w to about 15.00% w/w.

In certain embodiments, the whipping agent is a liquefied gas propellant, which includes, for example and without limitation, propane, isobutene, N-butane, Dymel 152a, 134a, hydrocarbons, DME (dimethyl ether), 1,3,3,3-tetrafluoropropene, and HFCs (1,1,2-tetrafluoroethane).

In certain embodiments, the whipping agent is a hydrocarbon propellant, which includes, for example and without limitation, methane, ethane, propane, butanes, and pentanes.

In certain embodiments, the formulation has one or more of characteristics such as little or no wetness after application, having a collapse time of at least 60 seconds, or structurally stable for at least 10 minutes.

The disclosed whipped formulation product represents the careful culmination of advancements in formulation, processing, and packaging to meet the end result of delivering a rich, creamy, spreadable, lightweight whipped product for consumer application.

Formulation:

Non-shear thickening emulsion chemistry has been developed to allow for high levels of gas dispersion, physical stability during temperature and pressure extremes, and post-dispensing foam stability. The chemistry has also been customized to allow for the inclusion of consumer-relevant ingredients that may include, for example and without limitation, skincare active agents (e.g., diaper rash treatment agents), skin protectants, moisturizers, emulsifying agents, film forming agents, thickening agents, skin feel aesthetic enhancers, antifungals, pH adjusters, pro vitamin additives, physical skin barriers, anti-bacterial agents, skin colorants, etc. Other ingredients are also contemplated, such as, without limitation, pain relief additives.

Processing:

In processing of certain embodiments, the blended formulation is transferred into a hopper, pressurized and under a controlled temperature, rate of flow and pressure, and is transferred into a high shear, continuous-flow, high-pressure "whipping" head, which rapidly mixes the base formulation with a series of infusion gas injector ports which controls the gas pressure and rates of flow with a selection of gases (or gas) to rapidly co-mingle the whipping agent and formulation solution, effectively dispersing the gas into the formulation prior to injection into the package. The gas-infused formulation is then tested for density inline and controlled under pressure and finally injected under pressure into the desired package.

In certain embodiments, the whipping agent is co-mingled with the formulation prior to filling the formulation into the package.

In certain embodiments, the whipping agent is nitrous oxide gas. In certain embodiments, the nitrous oxide in the formulation is about 0.1% w/w to about 4.0% w/w. In certain embodiments, the nitrous oxide in the formulation is about 0.1% w/w to about 10.0% w/w. In certain embodiments, the Nitrous Oxide in the formulation is about 0.1% w/w to about 1.9% w/w. In certain embodiments, the nitrous oxide in the formulation is about 0.1%, 1.0%, 1.9%, 2.0%, 3.0%, 4.0%, 5.0% w/w to about 6%, 7%, 8%, 9%, 10 w/w. Nitrous oxide has a slight sweet odor that can contribute to fragrance benefits (dual purpose gas benefits). Nitrous Oxide has a slight sweet odor that can contribute to fragrance benefits (dual purpose gas benefits).

In certain embodiments, certain other gases can serve as a particularly good whipping agent, as evaluated by the known or estimated Ostwald Coefficients of the blended mixture and gases. Taking into consideration the potential negative effects of co-mingling of the gases with base blended formulation, example being $CO_2$, which can react with water-containing formulas to create carbonic acid and cause shifts in product pH. Alternatively, $CO_2$ can be used as a whipping gas to deliberately modify the pH of the formulation to reach targeted pH levels. Gas propellant or combinations may also include, without limitation, $CO_2$, isobutane, nitrogen, Argon, air, oxygen, isopentane, other suitable gases, and combination thereof.

In certain embodiments, the whipping agent in the formulation is between about 0.01% w/w to about 15.00% w/w.

Unless otherwise noted or otherwise clear in context to a person of ordinary skill in the art, all % herein are weight to weight (w/w).

Packaging:

In certain embodiments, the pressure in the pressurized package is initially between about 15 psig to about 60 psig. In certain embodiments, the final pressure in the pressurized package is between about 80 psig to about 160 psig. In certain embodiments, the pressure initially is about 40 psig to 45 psig. In certain embodiments, the final pressure is about 110 psig to 120 psig.

In certain embodiments, the package is a Bag on Valve (BOV) pressurized assembly, comprising a two way fill/dispensing valve, an attached internal high barrier bag (affixed to valve), and rigid container capable of holding positive pressure (affixed to the valve). The container may be glass, barrier resin, metal/alloy, or another material capable of holding positive pressure. The container may be "pre-pressurized" with a combination of gaseous and/or liquid propellants prior to filling, with internal pressure expected to build as the internal volume is displaced during pressurized BOV filling.

The Bag on Valve assembly and accompanying "air gap" created between bag and the pressurized rigid container help to create an insulated barrier between the formulation and the user environment. This isolative barrier is helpful to moderate the temperature swings that might be experienced when taking this product from an ambient (indoor) location to a cooler or warmer environment, such as into the sun or into vehicles located in low/high temperature environments. This barrier helps to buffer formulation temperature change and help the formulation deliver a more consistent product experience (lower temperatures can form more rigid foam structures and high temperatures can cause weaker foam structures). This feature can be particularly useful for products formulated with lower melt point foam-formers, intended for use in elevated temperature environments.

Bag on Valve delivery systems differ from traditional aerosol delivery systems in at least the following district ways: Aerosols require propellant gases to be co-joined or co-mingled into the base formulation, as would be the case in single or multiphase system. These systems use the propellant gas to both expel the product and as a foaming and/or particle breakup agent. By contrast, a Bag on Valve system includes the use of a bag within a pressurized package. The bag is in direct contact with the single phase formulation and is expelled by application of pressure to the outside of the bag. As such, the propellant gas inside the package never comes in contact with the product. Particle breakup or foaming can be accomplished through the dispensing actuator design and/or through the inclusion of a secondary gas within the formulation.

This BOV design has several distinct benefits over traditional aerosol systems including without limitation:

Very high levels of product evacuation (>99% or even greater than 99.5%)

Has 3600 Dispense (Spray Any-Way)

The ability to dispense formulas without the need to comingle with the propellant gas ("pure" formulation concentrate)

The ability to include gases within the formation as a foaming or particle breakup mechanism that might not serve as a sufficient propellant system The ability to use two different gases within the system, one optimized as a propellant and one optimized as a foaming, forming (put in hand etc or particle breakup additive.

For example, in certain embodiments, Nitrous Oxide is used as a whipping agent without allowing "free gas" to be expelled and potentially abused. By contrast, whipped cream packaging which is sold in a traditional aerosol permits the user the ability to release and potentially abuse the gas propellant/whipping agent.

The pressure generating and maintaining component may be a gas, such as gaseous propellant, a liquid, such as a liquid propellant or a blend of gas and liquid. As used herein, a gaseous propellant may also be a compressed gas, such as $CO_2$, nitrous oxide and the like. As used herein, a liquid propellant may also be a liquefied gas, such as isobutane and the like.

The pressure generating and maintaining component can be formulated inside the device in a variety of ways, depending upon the nature of the component or components that form the pressure generating and maintaining component. The vehicle, while acting as pressure-generator, may be a gas, even though it may have been packaged as, for example, a gas, a liquid or a solid. Non-limiting examples of the gas are carbon dioxide ($CO_2$), nitrous oxide ($N_2O$) and the like. Thus, for example, if the vehicle is carbon dioxide, the carbon dioxide can be 'derived' inside the sealed pressurized container in several ways. For example, the gas could be pumped into the container.

If generating the gas by chemical reaction between a base and an acid, non-limiting examples of suitable bases include sodium bicarbonate, sodium carbonate, potassium bicarbonate, potassium carbonate and the like. Non-limiting examples of suitable acids include acetic acid, citric acid and the like. Sodium bicarbonate with citric acid is a suitable combination. Because the components are being combined inside of the sealed container (device), the gas produced during the reaction is trapped which pressurizes the container.

One advantage of the inventive system is that the gas introduced or produced may be non-flammable.

In certain embodiments, the whipped formulation product is characterized by microdispersion. In certain embodiments, the whipped formulation product is characterized by substantially consistent microvoid.

In certain embodiments, the whipping agent is a suitable gas. In certain embodiments, the whipping agent is co-mingled with the formulation prior to filling the formulation into the package.

In certain embodiments, the whipping agent is nitrous oxide gas. In certain embodiments, the nitrous oxide in the formulation is about 0.1% w/w to about 4.0% w/w. In certain embodiments, the nitrous oxide in the formulation is about 0.1% w/w to about 10.0% w/w. In certain embodiments, the Nitrous Oxide in the formulation is about 0.1% w/w to about 1.9% w/w. In certain embodiments, the nitrous oxide in the formulation is about 0.1%, 1.0%, 1.9%, 2.0%, 3.0%, 4.0%, 5.0% w/w to about 6%, 7%, 8%, 9%, 10 w/w. Nitrous oxide has a slight sweet odor that can contribute to fragrance benefits (dual purpose gas benefits).

In certain embodiments, certain other gases can serve as a particularly good whipping agent, as evaluated by the known or estimated Ostwald Coefficients of the blended mixture and gases. Taking into consideration the potential negative effects of co-mingling of the gases with base blended formulation, example being $CO_2$, which can react with water-containing formulas to create carbonic acid and cause shifts in product pH. Alternatively, $CO_2$ can be used as a whipping gas to deliberately modify the pH of the formulation to reach targeted pH levels. Gas propellant or combinations include, without limitation, $CO_2$, argon, isobutane, nitrogen, Argon, air, oxygen, isopentane, other suitable gases, and combination thereof.

In certain embodiments, the whipping agent in the formulation is between about 0.01% w/w to about 15.00% w/w.

In certain embodiments, the whipping agent is an aerosol propellant (including hydrocarbon propellant, compressed gas propellant, soluble gas propellant, and liquefied gas propellant) or a liquid propellant.

In certain embodiments, the whipping agent is a gas propellant. The gas propellant is, for example and without limitation, nitrogen, nitrous oxide, carbon dioxide, Argon, air or oxygen. In certain embodiments, the gas propellant in the formulation is between about 0.01% w/w to about 15.00% w/w.

In certain embodiments, the whipping agent is a liquefied gas propellant, which includes, for example and without limitation, propane, isobutene, N-butane, Dymel 152a, 134a, hydrocarbons, DME (dimethyl ether), 1,3,3,3-tetrafluoropropene, and HFCs (1,1,1,2-tetrafluoroethane).

In certain embodiments, the whipping agent is a hydrocarbon propellant, which includes, for example and without limitation, methane, ethane, propane, butanes, and pentanes.

In certain embodiments, the whipped formulation product comprises at least one recognized skincare active agent.

In certain embodiments, the whipped formulation product further comprises other ingredients, such as, for example and without limitation, one or more fatty alcohols—selected from, for example and without limitation, cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol (lanette 22), erucyl alcohol and 2-octyl-dodecanol. In certain embodiments, the whipped formulation is an After Sun lotion (contains Cetyl alcohol) but optionally without any added behenyl alcohol.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In one embodiment, the disclosed whipped product formulation dispenses in a continuous stream when an external pressure is applied to the device, such as by depressing the valve/actuator, thereby eliminating the need to squeeze and shake the formulation out of a bottle or tube.

In another embodiment, the disclosed whipped product in its device (package) operates as a "one-touch" delivery system; in such system, the user will hold down the actuator until the desired amount of formulation is dispensed.

In another embodiment, the disclosed whipped product in its package offers a continuous delivery system for an application, such as, for example and without limitation, skincare applications and suncare applications. Traditionally, "continuous delivery" is typically offered as a spray product and has been very successful due to the ease and speed that it provides for sunscreen application. Many consumers, however, prefer lotions/gels over sprays and would benefit from a continuous delivery mechanism. The present invention offers such an advantage.

The disclosed whipped formulation product can be used for any application that would benefit from such product, including, for example and without limitation, skincare, sunscreen, after sun care, vitamins, woundcare, etc. For each application, the formulation needs to comprise the corresponding active agent(s) and may further comprise other appropriate ingredients.

The disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel during application. This formulation spreads quickly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

The term "emulsion" identifies oil-in-water (o/w) or water-in-oil (w/o) type dispersion formulations intended for application to the skin, and air emulsion. Such dispersion formulations include, for example and without limitation, lotions and creams providing cosmetic or therapeutic benefits. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers, food, vitamins, etc., depending on the intended uses for the formulations.

In certain embodiments, the whipped formulation product comprises one or more of a thickening agent and/or an emulsifying agent.

Suitable emulsifiers are those known in the art for producing oil-in-water type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase or both, and assists with both the formation and the maintenance, or stability, of the emulsion.

Non-limiting examples of suitable emulsifiers or surfactants include pharmaceutically acceptable, non-toxic, non-ionic, anionic and/or cationic surfactants. Examples of suitable non-ionic surfactants include, for example and without limitation, glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, Prolipid and the like. An example of a suitable Prolipid is Prolipid 141 which lists behenyl alcohol, glyceryl stearate, palmitic acid, stearic acid, myristyl alcohol, lauryl alcohol, cetyl alcohol and lecithin as its ingredients in its Formula Data Sheet. Examples of suitable anionic surfactants are soaps including, for example and without limitation, alkali soaps, such as sodium, potassium and ammonium salts of aliphatic carboxylic acids, usually fatty acids, such as sodium stearate. Organic amine soaps include, for example and without limitation, organic amine salts of aliphatic carboxylic acids, usually fatty acids, such as triethanolamine stearate. Metallic soaps include salts of polyvalent metals and aliphatic carboxylic acids, usually fatty acids, such as aluminum stearate. Other classes of suitable anionic surfactants include, for example and without limitation, sulfated fatty acid alcohols such as sodium lauryl sulfate, sulfated oils such as the sulfuric ester of ricinoleic acid disodium salt, and sulfonated compounds such as alkyl sultanates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sultanate such as aryl naphthalene with alkyl substitutes. Examples of suitable cationic surfactants include, for example and without limitation, amine salts such as octadecyl ammonium chloride, quaternary ammonium compounds such as benzalkonium chloride. Non-limiting examples of emulsifiers include a mixture of cetearyl glucoside and cetearyl alcohol, available under the trade name Emulgade PL68/50 from Henkel KGaA, and PEG 30 dipolyhydroxy stearate, available under the trade name Arlacel 135 from ICI. Also preferred are various $C_{12-15}$, $C_{12-16}$ and $C_{14-15}$ alcohols available from various manufacturers, and Ceteareth 2, 10, 18, 22, Ceteth-1 and 20, cetyl dimethicone copolyol, and cetyl phosphate, glyceryl stearate, Oleth 3 and 10, polyglyceryl 3 methylglucose dis-tearate sorbitan isostearate, steareth 2, 10, and/or 20.

Other suitable emulsifiers are those known in the art for producing water-in-oil type emulsions. Non-limiting examples of some suitable water-in-oil emulsions include, for example and without limitation, Cithrol GMO 50-LQ (Glyceryl Oleate (&) Propylene Glycol), SIMALINE WO (PEG-30 Dipolyhydroxystearate; available from Seppic), FLUIDANOV 20X (Octyldodecanol & Octyldodecyl Xyloside; available from Seppic), ES-5300 (Lauryl PEG-10 Tris(trimethylsiloxy)silylethyl Dimethicone; available from Dow Corning), Abil EM90 (Cetyl PEG/PPG-10/1 Dimethicone; available from Evonik) and Abil WE09 (Polyglyceryl-4 Isostearate and Cetyl PEG/PPG-10/1 Dimethicone and Hexyl Laurate; available from Evonik). The typical water-in-oil emulsifier has a HLB value of about 4 to about 6, however, this "rule" is also known to have numerous exceptions.

It may be advantageous to incorporate thickening agents, such as, for instance, Avicel RC-591, Carbopol Ultrez, Carbopol ETD 2001, available from the B. F. Goodrich Co, Abil Wax 9801, a surfactant available from Evonik, Alginic Acid, available from Kelco, cellulose gum, available from TIC Gums, ammonium acrylates copolymer, ammonium polyacryloyl dimethyl taurate, bentonite available from Southern Clay, guar hydroxpropyltrimonium chloride available from Henkel, hydroxy propylprocellulose available from Aqualon, magnesium aluminum silicate, available from Salomon, potassium alginate available from Kelco, beeswax available from Strah & Pitsch, and behenyl alcohol available from Nikko.

The disclosed formulation/formulations may contain a wide range of additional, optional components. The CTFA Cosmetic Ingredient Handbook, Seventh Edition, 1997, the Eighth Edition, 2000, and the personal care council website (http://www.personalcarecouncil.org/) describe a wide variety of cosmetic and pharmaceutical ingredients commonly used in skin care formulations, which are suitable for use in the formulations of the present invention. Examples of these functional classes disclosed in these references include, for example and without limitation: absorbents, abrasives, anti-caking agents, anti-foaming agents, antioxidants, binders, biological additives, buffering agents, bulking agents, chelating agents, chemical additives, colorants, cosmetic astringents, cosmetic biocides, cryoprotectants, film stabilizers, denaturants, drug astringents, external analgesics, film formers, fragrance components, humectants, pacifying agents, pH adjusters, plasticizers, preservatives, propellants, reducing agents, skin bleaching agents, skin-conditioning agents (emollients, humectants, miscellaneous, and occlusive), skin protectants, solvents, SPF enhancers/boosters, foam boosters, hydrotropes, solubilizing agents, suspending agents (nonsurfactant), sunscreen agents, ultraviolet light absorbers, water-proofing agents, and viscosity increasing agents (aqueous and nonaqueous).

An emollient is a substance which helps to smooth and soften the skin, and may also reduce its roughness, cracking or irritation. Non-limiting examples of suitable emollients include, for example and without limitation, mineral oil, lanolin oil, coconut oil, cocoa butter, olive oil, almond oil, macadamia nut oil, synthetic jojoba oils, natural Sonora jojoba oils, safflower oil, corn oil, liquid lanolin, cottonseed oil and peanut oil. Preferably, the emollient is a mineral oil NF. One or more emollients may be present ranging in amounts from about 1 percent to about 30 percent by weight.

Other suitable emollients include, for example and without limitation, Aloe Barbadensis Leaf Extract, which is a mixture of Aloe Barbadensis Leaf Extract (&) Cocos Nucifera (Coconut) Oil (&) Mineral Oil. squalane, castor oil, polybutene, sweet almond oil, avocado oil, calophyllum oil, ricin oil, vitamin E acetate, olive oil, silicone oils such as dimethylopolysiloxane and cyclomethicone, linotenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and poly-alcohols such as those of glycol and glyceryl, ricinoleates esters such as isopropyl adipate, hexyl laurate and octyl dodecanoate, dicaprylyl maleate, hydrogenated vegetable oil, phenyltrimethicone, and jojoba oil.

Other suitable emollients which are solids or semi-solids at ambient temperatures may be used. Such solid or semi-solid cosmetic emollients include, for example and without limitation, petrolatum, glyceryl dilaurate, hydrogenated lanolin, hydroxylated lanolin, acetylated lanolin, isopropyl lanolate, butyl myristate, cetyl myristate, myristyl myristate, myristyl lactate, cetyl alcohol, isostearyl alcohol and isocetyl lanolate. One or more of these emollients can be optionally included in the formulation.

The whipped formulations can further comprise skin protectant active agents. Suitable examples include, for example and without limitation, (with preferred weight percent ranges), Allantoin (0.5 to 2 percent); Aluminum hydroxide gel (0.15 to 5 percent), Calamine (1 to 25 percent); Cocoa butter (greater than 50 percent); Cod liver oil (5 to 14 percent); Dimethicone (1 to 30 percent); Glycerin (20 to 45 percent); Hard fat (greater than 50 percent); Kaolin (4 to 20 percent); Lanolin (12.5 to 50 percent); Mineral oil (greater than 50% percent); Petrolatum/White petrolatum (in certain embodiments, greater than 30% percent); Topical starch (10 to 98 percent); Zinc acetate (0.1 to 2 percent); Zinc carbonate (0.2 to 2 percent); and Zinc oxide (1 to 25 percent), and zinc oxide in ointment (1 to 40 percent). Additional skin protectant active agents may include Colloidal oatmeal or Sodium bicarbonate.

In certain embodiments, water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or formulation can range from about 15 percent to 95 weight percent. In other embodiments, water is not required.

A humectant is a moistening agent that promotes retention of water due to its hygroscopic properties. Suitable humectants include, for example and without limitation, sorbitol, glycerin, polymeric glycols such as polyethylene glycol and polypropylene glycol, and mannitol. Preferably, the humectant is glycerin, Sorbitol 70% USP or polyethylene glycol 400, NF. More preferably, the humectant is Sorbitol 70% USP. One or more humectants can optionally be included in the formulation in amounts from about 1 percent to about 20 percent by weight, preferably about 3 percent by weight. Other suitable humectants include, inter alia, fructose, glucose, lactic acid, PCA, potassium lactate and PCA, propylene glycol, sodium lactate and PCA.

An antimicrobial preservative may be part of the disclosed formulation. An antimicrobial preservative is a substance or preparation which destroys, prevents or inhibits the proliferation of, microorganisms in the skincare formulation, and which may also offer protection from oxidation. Preservatives are frequently used to make self-sterilizing, aqueous based products such as emulsions. This is done to prevent the development of microorganisms that may grow in the product during the manufacture and distribution of the product and/or during use by consumers, who may further inadvertently contaminate the products during normal use. Typical preservatives include, for example and without limitation, the lower alkyl esters of para-hydroxyben-zoates (parabens), especially methylparaben, propylparaben, isobutylparaben and mixtures thereof, benzyl alcohol, phenyl ethyl alcohol and benzoic acid. The preferred preservative is benzyl alcohol. One or more antimicrobial preservatives can optionally be included in an amount ranging from about 0.001 to about 10 weight percent, preferably about 0.05 to about 1 percent.

An antioxidant may be part of the disclosed formulation. An antioxidant is a natural or synthetic substance added to the sunscreen to protect from or delay its deterioration due to the action of oxygen in the air (oxidation) and to protect the skin from sun damage. Antioxidants prevent oxidative deterioration which may lead to the generation of rancidity and nonenzymatic browning reaction products. Typical suitable antioxidants include, for example and without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Oxynex (Oxynex ST liquid is a mixture of diethylhexyl syringyliden-emalonate and caprylic/capric triglyceride), Vitamin A, Vitamin E and Vitamin C. One or more antioxidants can optionally be included in the formulation in an amount ranging from about 0.001 to about 5 weight percent, preferably about 0.01 to about 0.5 percent.

Chelating agents may be part of the disclosed formulation. Chelating agents are substances used to chelate or bind metallic ions, such as with a heterocyclic ring structure so that the ion is held by chemical bonds from each of the participating rings. Suitable chelating agents include, for example and without limitation, ethylene diaminetetraacetic acid (EDTA), EDTA disodium, calcium disodium edetate, EDTA trisodium, citric acid, EDTA tetrasodium and EDTA dipotassium. One or more chelating agents can optionally be included in the formulation in amounts ranging from about 0.001 to about 0.2 weight, percent preferably about 0.01% weight percent.

The disclosed formulation may include foam stabilizers or foam stabilizing agents. There are many examples of such agents and means to achieve foam stability. Non-limiting examples of suitable foam stabilizers include, for example and without limitation, the Avicels, Capmul S12L, Capmul S18L, Amilite GCK-12, Amadol CMA-2, Ampholak 7 CX-C, Ampholak X C0-30, Polyox WSR N-10, Amaranth S, Foam-Coll 5, Blanose 12M31XP, Genu carrageenan, Avanel S150CG and others. Avicel is an example that can be used in the formulation. For example, Avicel RC-591 is a mixture of cellulose gum and microcrystalline cellulose. Some foam stabilizers also help improve long term high temperature stability.

Fragrances are aromatic substances which can impart an aesthetically pleasing aroma to the skincare or sunscreen formulation and may be part of the disclosed formulation. Typical fragrances include, for example and without limitation, aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

A pH modifier may be part of the disclosed formulation. A pH modifier is a compound that will adjust the pH of a formulation to a lower, e.g., more acidic pH value, or to a higher, e.g., more basic pH value. The disclosed formulations may contain such pH modifiers as is necessary.

The disclosed whipped formulation product has been developed, in part, to offer consumers a unique and better way to apply topical products such as sunscreen and skin creams to themselves and others.

One advantage of the disclosed whipped formulation product is during dispensing the density of the formulation contained within the package may drop measurably. The resulting dispensed product represents a whipped product (a foam) of substantial rigidity and body, slow to collapse under ambient and elevated temperature conditions but easy to "break" upon physical manipulation, as for example during rubbing. This allows for a more "controlled" and even dispersal/spreading/distribution of product as compared to the initial "un-whipped" presentation of the formulation.

Another advantage of the disclosed whipped product arises from the ability to contain such a large "dispensed volume" in such a condensed package format, allowing for a far more consumer friendly and portable package size/format for such a large volume of dispensed product.

In certain embodiments, the disclosed whipped formulation product can allow for more control of spread over body.

In certain embodiments, the disclosed whipped formulation product allows for high levels of product evacuation, particularly for viscous products as compared to traditional non-pressurized emulsion packaging. In certain embodiments, the disclosed whipped formulation product with its pressured system allows for elevated levels of gas to be dispersed into formulation, beyond what ambient condition would normally allow, which can increase whipping potential (lower resulting dispensed densities) and reduce sputtering that can be caused by dispersing high levels of gas into formulation but failing to provide adequate pressure to contain the dispersed gas. In certain embodiments, the disclosed whipped formulation product results in reduced corrosion potential by separating the formulation from the rigid, pressurized container (if metal) by containing the formulation in the internal bag.

In certain embodiments, the disclosed whipped formulation product can have its gas propellant or combination, pressure, and gas dispersion customized for each formulation. Whereas oil and water emulsions are particularly well suited for specific gases, liquid propellants can provide much larger bubble structures. BOV dispensing mechanism allows for co-blending of the various types of liquid and gas-phase propellant allowing to dispense whipped products without substantially altering temperature or potentially induce a cooling effect due to phase change energy absorption.

The disclosed whipped product is a light and spreadable formulation and thus may be particularly well suited for sensitive or compromised skin applications, such as applying a whipped diaper rash product.

The disclosed whipped product form is designed to dispense, for example and without limitation, lotion/cream/ointment/oral dosage forms/whipped cream in a controlled manner by delivering a pressurized, foaming formulation via a dispensing orifice at the touch of a button. The product is dispensed via an actuator that depresses a valve stem into a female aerosol valve. Upon activation, the gas-saturated formulation experiences a drop in pressure as it moves from a pressurized containment system to ambient conditions. This change in pressure allows the saturated gas to rapidly expand, creating bubbles within the formulation, leading to a formulation of reduced density. Formulation customizations allow these bubbles to remain stable for 10 seconds or longer, permitting the user to spread the resulting product onto a surface with enhanced coverage benefits.

Although specific suppliers of commercially available ingredients may be listed herein, it is understood that these products may be available from additional suppliers and that the instant invention is not limited to only that ingredient from the specifically cited supplier. Rather the supplier is being provided as an example of what is commercially available.

Description of Certain Embodiments of the Whipped Product

Luxurious whipped product, whipped, light, spongy, soft, pillowy
No shake whipping
Has 3600 Dispense (Spray Any-Way)
Not runny; stays where you put it
Easy to apply and handle, faster, easier application
More controllable, no drip allows precise placement, no smear mess but pull product to control application. Can apply multiple dollops to body at one time. Thus can put package down and not have to touch again while rubbing in multiple dollops
Quick rub-out time
Different sensory (drag of product), smoothness
Connect emotionally with application experience
Perception—whipped dries more quickly
After feel—no wetness/drag/tackiness
Coping mechanism: whipped made convenient/quiet/easy dispose
Characterization of the product—brightness, density, surface tension, pH, stability, sheer, dose, sound, drag (skin feel)—low drag, sheen, full bodied, insulation, contact temperature, wetness, slip, sound cue
Change in physical properties only, maintains formulation properties with enhanced application benefits, "transforms application but not properties"
Micro-voids, micro-bubbles, infused, air emulsion, trap gas in structure
Consistent whipped product over life of product—beginning to end
Reduce in dead inventory
Stable, super-dispersed nitrous oxide loading, helps to create microbubbles and thus unique structure
Can create variable drag experience based on processing reduced drag application, increased/better/easier application
low sheer application for sensitive/damaged skin
Create and maintain higher solubility product through containment under elevated pressure (allows constant pressure overtime)
Size of nozzle (sheer rate impact) →sound profile In certain embodiments, the formulation is expelled from the package without shaking the package.

Sensory Impact

The disclosed whipped formulation product represents the careful culmination of advancements in formulation, processing, and packaging to deliver a rich, creamy, spreadable, lightweight whipped product for consumer application. The disclosed formulation also delivers desired sensory impact to a user.

Sensory impact (such as appearance of the whipped product, sound upon dispensing the product from the can, and impact on the skin of the whipped formulation, etc.) to the user may be evaluated by, for example, trained personnel to determine how product variants are perceived differently by the user, with statistical confidence. Those formulations determined to have desired sensory impact are thus selected. In certain embodiments, the user's senses are highly satisfied by the disclosed formulation after its application on the user.

Two intertwined process variables may contribute to controlling the consumer experience associated with a base formula; gas loading (e.g., nitrous oxide) into the formulation with the active ingredient, which impacts density, spreadability, sound, and physical appearance of product; and pre-gas can pressure, which influences stability of gas emulsion, sound, speed of dispense, sputtering, and "quality" characteristics. Multiple product variants, combining these two process variables, are run and are being physically evaluated. Physical measurements may be made, including CT scans to yield "in can" product profile characterization details; dispensing observations (such as appearance of the whipped product, sound upon dispensing the product from the can, and impact on the skin of the whipped formulation, etc.), and high temperature foam stability; and post-dispensing physical measurements including density, bubble size, and bubble size distribution. Sensory impact (such as appearance, sound, and skin impact) to the user of these multiple product variants may be evaluated by, for example, trained personnel to determine how product variants are perceived differently by the user, with statistical confidence. Some of these tested whipped formulations would have desired sensory impact to the user. For any given product, the following parameters, as well as any other parameters that impact a user's sense(s), may be evaluated.

Appearance: visual compactness, integrity of shape, gloss, hue, intensity, brightness, opacity, whitening, etc.

Sound impact upon dispensing from the can: volume, tone, crackling/popping, sputtering, etc.

Skin Feel: firmness, stickiness, cohesiveness, peaking, wetness, spreadability, coolness, thickness, slipperiness, oiliness, waxiness, greasiness, rubs to absorbency, tautness, roughness, thickness of residue, grittiness, graininess, chalkiness, peeling/flaking, pilling, powdery-ness, plastic/coated, etc.

In certain embodiments, the whipped formulations have desired sensory impact to a user, who may be a human user. In certain embodiments, the formulations have high sensory impact to the user; in certain embodiments, the high sensory impact is characterized by one or more of the following: positive appearance, low sound impact, high integrity of shape, visual compactness, high spreadability, positive skin feel, afterfeel (immediately after application or after a few minutes after application, such as about 10 minutes after) as well as other sensory input perceivable by a user.

The disclosed method allows for tweaking the consumer experience attributes of a whipped formulation in multiple directions, allowing is to deliver "soft and gentle" or "aggressive and greasy," etc., depending on consumer preference. Some of the attributes are: appearance, sound impact, integrity of shape, spreadability, and skin feel. All these, as well as other parameters, may be chosen such that the whipped formulation has the desired attributes.

For appearance, in certain embodiments, the appearance is a well-formed dollop; in other embodiments, such as for Kid's Messy-Loud sunscreen, the product upon dispensing sputters.

For sound impact, in certain embodiments, such as Kid's Messy-Loud sunscreen, the sound impact upon dispensing is obnoxiously loud and disruptive; in other embodiments, the sound impact is as low as possible.

For skin feel, in certain embodiments, such as Baby and Clearly Sheer, the skin feel provided by the formulation is a soft, none greasy-feel experience; in other embodiments, such as sunscreen for sport users who want to feel their sunscreen is working hard and staying with them as they move, the skin feel provided is one or more of greasiness, heaviness, and glossy.

In certain embodiments, the disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sunscreen during application. This formulation spreads quickly and disappears rapidly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In certain embodiments, the disclosed formulation has one or more of the following physical characteristics: a majority of bubbles being of a bubble size of less than 20 µm, high number of bubbles, high bubble density, and high foam stability. In certain embodiments, the disclosed formulations have high foam stability at high temperatures, such as at 25° C. to 37° C., or 37° C. to 50° C.

In certain embodiments, the color of the whipped formulation post-dispensing is white. The whiteness of the whipped lotion may be used as a visual queue for application on skin.

In certain embodiments, the formulation has at least about 60% of the gas bubbles at ≤100 µm, after the formulation is expelled from the package. In certain embodiments, the formulation has at least about 40% of the gas bubbles at ≤60 µm, after the formulation is expelled from the package.

In certain embodiments, the whipped formulation product is characterized by microdispersion. In certain embodiments, the whipped formulation product is characterized by substantially consistent microvoid.

In certain embodiments, the whipped formulation product is highly emollient. In certain embodiments, the whipped formulation product has about 60% or more of the gas bubbles at ≤100 µm. In certain other embodiments, the whipped formulation product has about 40% or more of the gas bubbles at ≤60 µm. The gas bubbles are formed from the gas propellant co-mingled with the formulation prior to filling the formulation into the package.

In certain embodiments, the formulation has one or more of characteristics such as little or no wetness after application, having a collapse time of at least 60 seconds, or structurally stable for at least 30 minutes. Examples For this invention to be better understood, the following examples are set forth. These examples are for purposes of illustration only and are not to be construed as limiting the scope of the invention in any manner.

Example 1

Currently, A+D® Diaper rash products are available as an original ointment and zinc oxide cream. For this study, A+D® zinc oxide cream, which contains 10% w/w zinc oxide, is utilized to explore the feasibility of developing a new whipped delivery system. In addition, the feasibility of developing a whipped 40% (w/w) zinc oxide ointment is evaluated. The whipped zinc oxide cream and ointment evaluated in this study are manufactured and packaged at the intended manufacturing site. Formulation details and brief manufacturing process for the tested whipped products are summarized in Tables 1 through 4.

As summarized in FIGS. 1 and 2, both whipped zinc oxide (ZnO) products (10% ZnO cream and 40% ZnO ointment) are whippable and produced whipped-foams having excellent spreadability with soft/smooth texture. The resultant whipped-foams are stable at least 10 minutes at room temperature (RT), suggesting that consumers (particularly mothers) can control the speed of distributing these whipped products on babies and still have "light and airy" application experience. The stability results in FIG. 3 clearly show that both whipped ZnO products are able to deliver "whipped-foam" with adequate structure after storage at 50° C./75% RH for 1 day.

Accordingly, it is feasible to develop whipped zinc oxide products spanning a large ZnO concentration range, having positive whipped characteristics.

TABLE 1

Formulation Information of Whipped Zinc Oxide (10% w/w) Cream

Table 1.A: Composition of Whipped Zinc Oxide (10% w/w) Cream (Finished Products)

| Component | Concentration (% w/w) |
| --- | --- |
| Zinc Oxide (10% w/w) Cream Concentrate | 98.00 |
| Nitrous Oxide | 2.00 |

TABLE 1-continued

Formulation Information of Whipped Zinc Oxide (10% w/w) Cream

Table 1.B: Ingredient Composition of Zinc Oxide (10% w/w) Cream Concentrate (Base Formulation)

| Ingredient | Concentration (% w/w) |
| --- | --- |
| Ozokerite Wax SP-1021P | 2.00 |
| Paraffin Wax NF | 1.00 |
| Synthetic Bees Wax | 1.50 |
| Light Mineral Oil, NF | 15.00 |
| Dimethicone, NF 350 cst | 1.00 |
| Purified Water, USP | 45.98 |
| Zinc Oxide, USP | 10.00 |
| Sorbitol Solution, USP 70% | 20.00 |
| Benzyl Alcohol, NF | 0.40 |
| Cithrol GMO 50-LQ (Arlacel 186) | 3.00 |
| *Aloe Barbadensis* Leaf Extract | 0.05 |
| Cod Liver Oil, 1000A/100D | 0.05 |
| Fragrance, Baby Powder | 0.02 |

TABLE 2

Laboratory manufacturing process for Whipped Zinc Oxide (10% w/w) Cream

Table 2.A. Zinc Oxide (10% w/w) Cream Concentrate (Base Formulation)

| | Concentration (% w/w) | Manufacturing Directions |
| --- | --- | --- |
| Part A Ingredients | | |
| Light Mineral Oil, NF | 15.00 | Step 1: In a container large enough to hold the entire batch, add Light Mineral Oil of Part A and begin heating to 160-168° F. while mixing. Add the other Part A ingredients, maintaining temperature at 160-168° F. (target 165° F.). Note: visually confirm the waxes are completely melted. |
| Synthetic Bees Wax | 1.50 | |
| Ozokerite Wax SP-1021P | 2.00 | |
| Paraffin Wax NF | 1.00 | |
| Dimethicone, NF 350 cst | 1.00 | |
| Part B Ingredients | | |
| Purified Water, USP | 45.98 | Step 2: Add the hot (160-168° F.) water of Part B to the main batch while mixing. Add Part B Zinc Oxide (Active) and mix to form the emulsion (maintain temperature at 160-168° F.). |
| Zinc Oxide, USP | 10.00 | |
| Part C Ingredient | | |
| Sorbitol Solution, USP 70% | 20.00 | Step 3: Add Part C Sorbitol Solution to the batch while mixing. |
| Part D Ingredients | | |
| Benzyl Alcohol, NF | 0.40 | Step 4: Add Part D Benzyl Alcohol to the batch and mix to disperse. With continued mixing, add the Part D Arlacel 186 and proceed immediately to the next Step. |
| Cithrol GMO 50-LQ (Arlacel 186) | 3.00 | |
| Part E Ingredients | | |
| *Aloe Barbadensis* Leaf Extract | 0.05 | Step 5: Begin cooling and continue to mix until the batch temperature reaches 115-120° F. Add the Part E *Aloe Barbadensis* Leaf Extract and Cod Liver Oil while mixing. |
| Cod Liver Oil, 1000A/100D | 0.05 | |

TABLE 2-continued

Laboratory manufacturing process for Whipped Zinc Oxide (10% w/w) Cream

Part F Ingredients

| | | |
|---|---|---|
| Fragrance, Baby Powder | 0.02 | Step 6: When the batch reaches 100-105° F., add the Part F fragrance with mixing. Cool the batch to room temperature (86° F. or less). |

Table 2.B. Finished Product (Concentrate + Gas): Whipped Zinc Oxide (10% w/w) Cream

| Ingredients | Concentration (% w/w) |
|---|---|
| Zinc Oxide (10% w/w) Cream Concentrate | 98.00 |
| Nitrous Oxide ($1^{st}$ gas) | 2.00 |
| $2^{nd}$ gas | To Pressure: 40 psig |

The following progression outlines the major steps involved in the laboratory production of a Whipped embodiment (Finished Product) at ambient temperature.

(1) Gas co-processing step: The concentrate (base formulation) is added to the mixing chamber and a 1st Gas is vigorously co-mingled or dispersed with a high pressure mixing head into the base formulation at 150 psig, and held at pressure until Packaging Step.

(2) Pre-pressurizing step: Pressurizing of a 2nd gas between a bag and the inside wall of the Bag on Valve product package to no less than 40 psig.

(3) Packaging step: Packaging the pre-mixed formulation (concentrate+the 1st gas) into the pre-pressurized Bag on Valve (BOV) package by injection into the two way valve opening at a pressure of at least 400 psig.

In certain embodiments, the following process is used.

1) Concentrate Production Step: The base sunscreen emulsion was processed in accordance with the manufacturing process according to Table 1, and held for the Gas Co-Processing step.

2) Gas Co-Processing Step: The base sunscreen formulation was added to the mixing chamber and a 1st Gas was vigorously co-mingled or dispersed with a high pressure mixing head into the base formulation at 150 psig, and held at pressure until Packaging Step.

3) Pre-pressurizing step: Pressurizing of a 2nd gas between a bag and the inside wall of the Bag on Valve product package to no less than 40 psig.

4) Packaging step: Packaging the pre-mixed formulation (concentrate+the 1st gas) into the pre-pressurized Bag on Valve (BOV) package by injection into the two way valve opening at a pressure of at least 400 psig.

TABLE 3

Formulation Information of Whipped Zinc Oxide (40% w/w) Ointment

Table 3.A: Composition of Whipped Zinc Oxide (40% w/w) Ointment (Finished Products)

| Component | Concentration (% w/w) |
|---|---|
| Zinc Oxide (40% w/w) Ointment Concentrate | 98.00 |
| Nitrous Oxide | 2.00 |

Table 3.B: Ingredient Composition of Zinc Oxide (40% w/w) Ointment Concentrate (Base Formulation)

| Ingredient | Concentration (% w/w) |
|---|---|
| Ozokerite Wax SP-1021P | 1.00 |
| White Petrolatum | 4.00 |
| Synthetic Bees Wax | 1.70 |
| Light Mineral Oil, NF | 27.413 |
| Purified Water, USP | 19.00 |
| Zinc Oxide, USP | 40.00 |
| Sorbitol Solution, USP 70% | 3.00 |
| Benzyl Alcohol, NF | 0.45 |
| Cithrol GMO 50-LQ (Arlacel 186) | 3.30 |
| *Aloe Barbadensis* Leaf Extract | 0.06 |
| Cod Liver Oil, 1000A/100D | 0.055 |
| Fragrance, Baby Powder | 0.022 |

TABLE 4

Laboratory manufacturing process for Whipped Zinc Oxide (40% w/w) Ointment

Table 4A Zinc Oxide (40% w/w) Ointment Concentrate (Base Formulation)

| | Concentration (% w/w) | Manufacturing Directions |
|---|---|---|
| Part A Ingredients | | |
| White Petrolatum | 4.00 | Step 1: Add Part A ingredients in |
| Synthetic Bees Wax | 1.70 | a main vessel and heat to 74° C. |

TABLE 4-continued

Laboratory manufacturing process for Whipped Zinc Oxide (40% w/w) Ointment

| | | |
|---|---|---|
| Light Mineral Oil, NF | 27.413 | (71-76° C.) under prop agitation |
| Ozokerite Wax SP-1021P | 1.00 | (or prop speed homogenizer). |
| Cithrol GMO 50-LQ | 2.30 | |
| Part B Ingredients | | |
| Purified Water, USP | 19.00 | Step 2: Add Part B ingredients in order, slowly, under high prop speed agitation. Use cowels type disperser at rheostat min. 300 maintaining 74° C. (71-76° C.) NLT 5 minutes. If temperature drops, reheat under prop agitation. |
| Sorbitol Solution, USP 70% | 3.00 | |
| Benzyl Alcohol, NF | 0.45 | |
| Part C Ingredient | | |
| Zinc Oxide, USP | 40.00 | Step 3: Add Part C ZnO under disperser. Mix NLT 20 minutes maintaining temperature with hot plate. If needed, reheat in water bath with prop agitation. Ensure all ZnO is smoothly dispersed. |
| Part D Ingredients | | |
| Cithrol GMO 50-LQ | 1.00 | Step 4: Add Part D ingredient under disperser and mix 15 min. maintaining 74° C. (71-76° C.). Ensure there are no discreet ZnO particles, and batch is smooth. Begin cooling under side wipe agitation, pulse with disperser as needed. |
| Part E Ingredients | | |
| *Aloe Barbadensis* Leaf Extract | 0.06 | Step 5: At 55° C. (54-58° C.), switch to side wipe only and add Part E ingredients in order. Continue cooling. |
| Cod Liver Oil, 1000A/100D | 0.055 | |
| Part F Ingredients | | |
| Fragrance, Baby Powder | 0.022 | Step 6: At 38° C. (37-41° C.), add Part F ingredient. Mix NLT 20 minutes with recirculation (No ISG) and continue cooling. At 30° C., mix NLT 5 minutes and confirm warmest temperature of the batch is 30° C. at any given point. |

Table 4B Finished Product (Concentrate + Gas): Whipped Zinc Oxide (40% w/w) Ointment

| Ingredients | Concentration (% w/w) |
|---|---|
| Zinc Oxide (40% w/w) Ointment Concentrate | 98.00 |
| Nitrous Oxide (1st gas) | 2.00 |
| 2nd gas | To Pressure: 40 psig |

The following progression outlines the major steps involved in the laboratory production of a Whipped embodiment (Finished Product) at ambient temperature.

(1) Gas co-processing step: The concentrate (base formulation) is added to the mixing chamber and a 1st Gas is vigorously co-mingled or dispersed with a high pressure mixing head into the base formulation at 150 psig, and held at pressure until Packaging Step.

(2) Pre-pressurizing step: Pressurizing of a 2nd gas between a bag and the inside wall of the Bag on Valve product package to no less than 40 psig.

(3) Packaging step: Packaging the pre-mixed formulation (concentrate+the 1st gas) into the pre-pressurized Bag on Valve (BOV) package by injection into the two way valve opening at a pressure of at least 400 psig.

Example 2 Physical Characteristics Due to Changes in Gas Loading and Pre-Gas Pressure Example 2A Two intertwined process variables may contribute to controlling the consumer experience associated with a whipped formulation: (1) gas loading (e.g., Nitrous Oxide), which impacts density, spreadability, sound profile during dispensing, and physical appearance of product; and (2) pre-gas can pressure, which influences stability of gas emulsion, sound, speed of dispense, sputtering, and "quality" characteristics. Multiple product variants, combining these two process variables, were run and were being physically evaluated. Physical measurements were made, including CT scans, to yield "in can" product profile characterization details; dispensing observations (appearance, sound, etc.) and high temperature foam stability; and post-dispensing physical measurements including density, bubble size, and bubble size distribution.

Nine formulations manufactured at various process conditions, representing the practical range of "cut bag" (pre-gas) pressure and nitrous oxide loading, shown in shown in Tables 5 and 7-9 were tested.

TABLE 5

|  |  | Cut Bag Pressure (psi) | | |
|---|---|---|---|---|
|  |  | 20 | 32.5 | 45 |
| Product | 50 | X | X | X |
| Density g/L | 125 | X | X | X |
|  | 200 | X | X | X |

Each variable combination sampled was evaluated via a CT Scanner to determine bubble size and bubble size distribution while remaining in-can and under elevated pressure. The samples were then evaluated after dispensing across a wide range of factors including appearance, bubble size and distribution, and high temperature foam stability. The results are shown in FIGS. 4-27.

Figure 5:
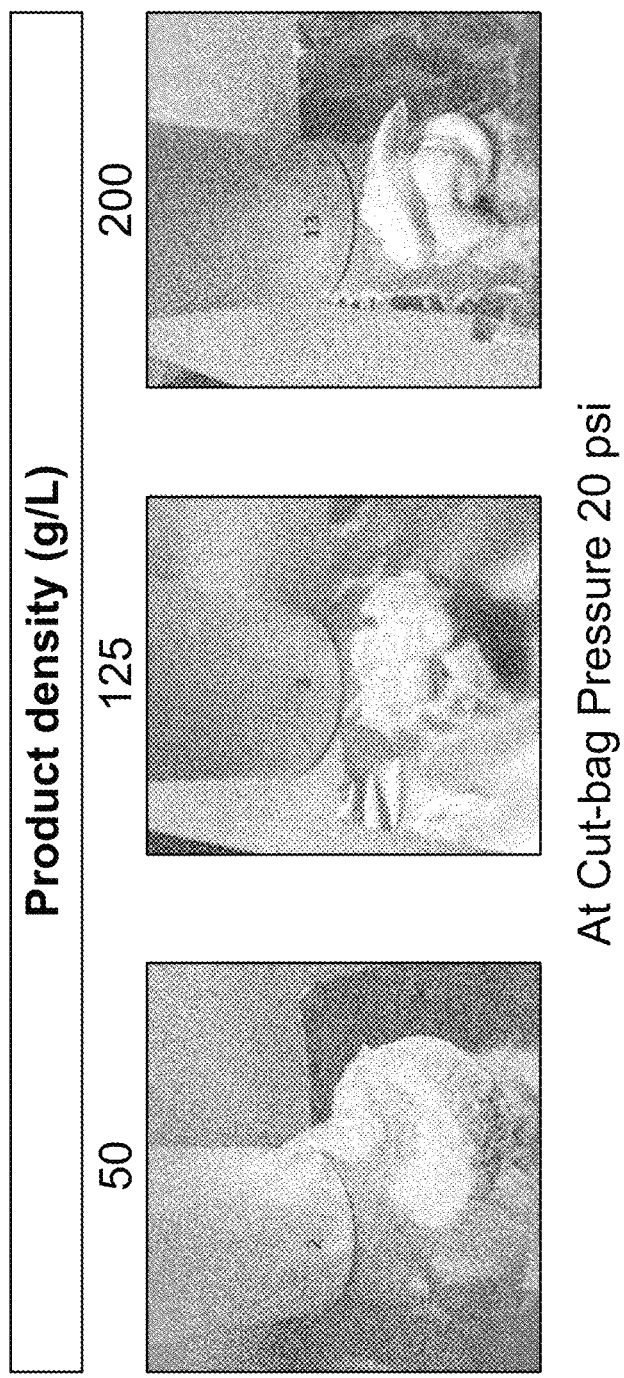
FIG. 5 shows appearance of "whipped foam" at various product densities and at 20 psi cut-bag pressure.

Some post-dispensed results are:

Appearance of "whipped foam": richer, more voluminous appearance at lower product density (FIG. 5).

Figure 6:
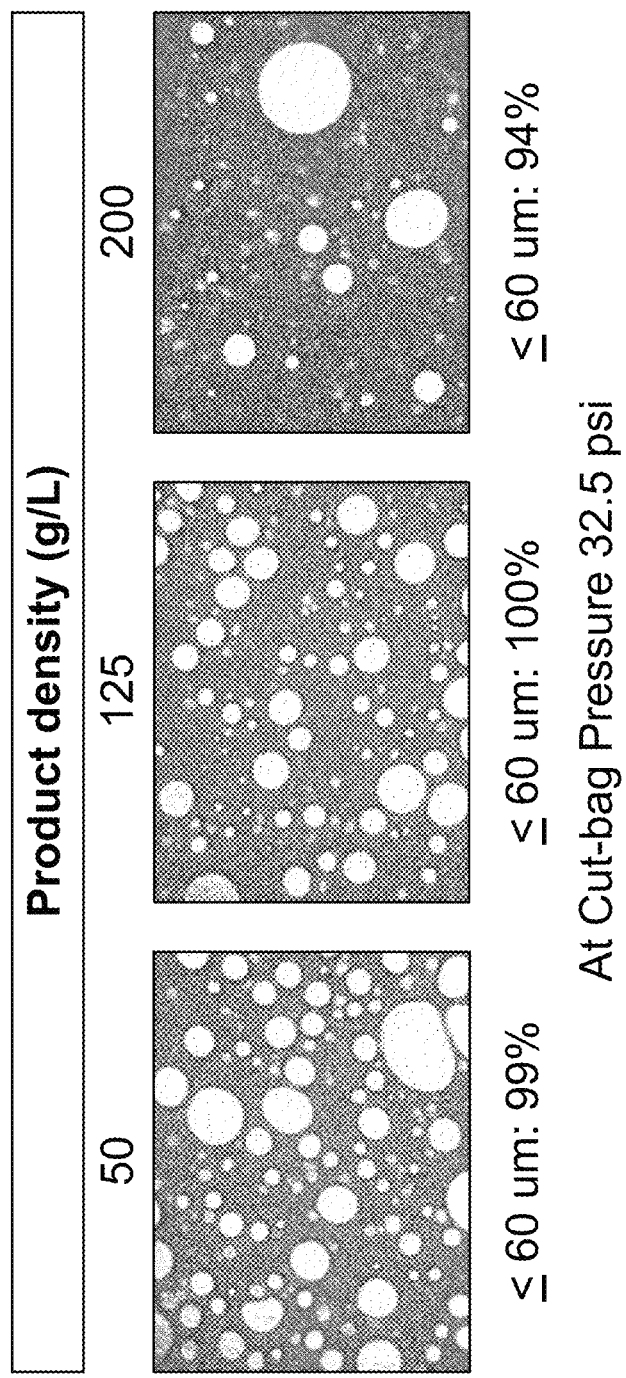
FIG. 6 shows results of bubble size and distribution at various product densities and at 32.5 psi cut-bag pressure. Lower product density leads to higher levels of small bubbles.

Gas bubble size and distribution: lower product density leads to higher levels of small bubbles (FIG. 6).

Figure 7:
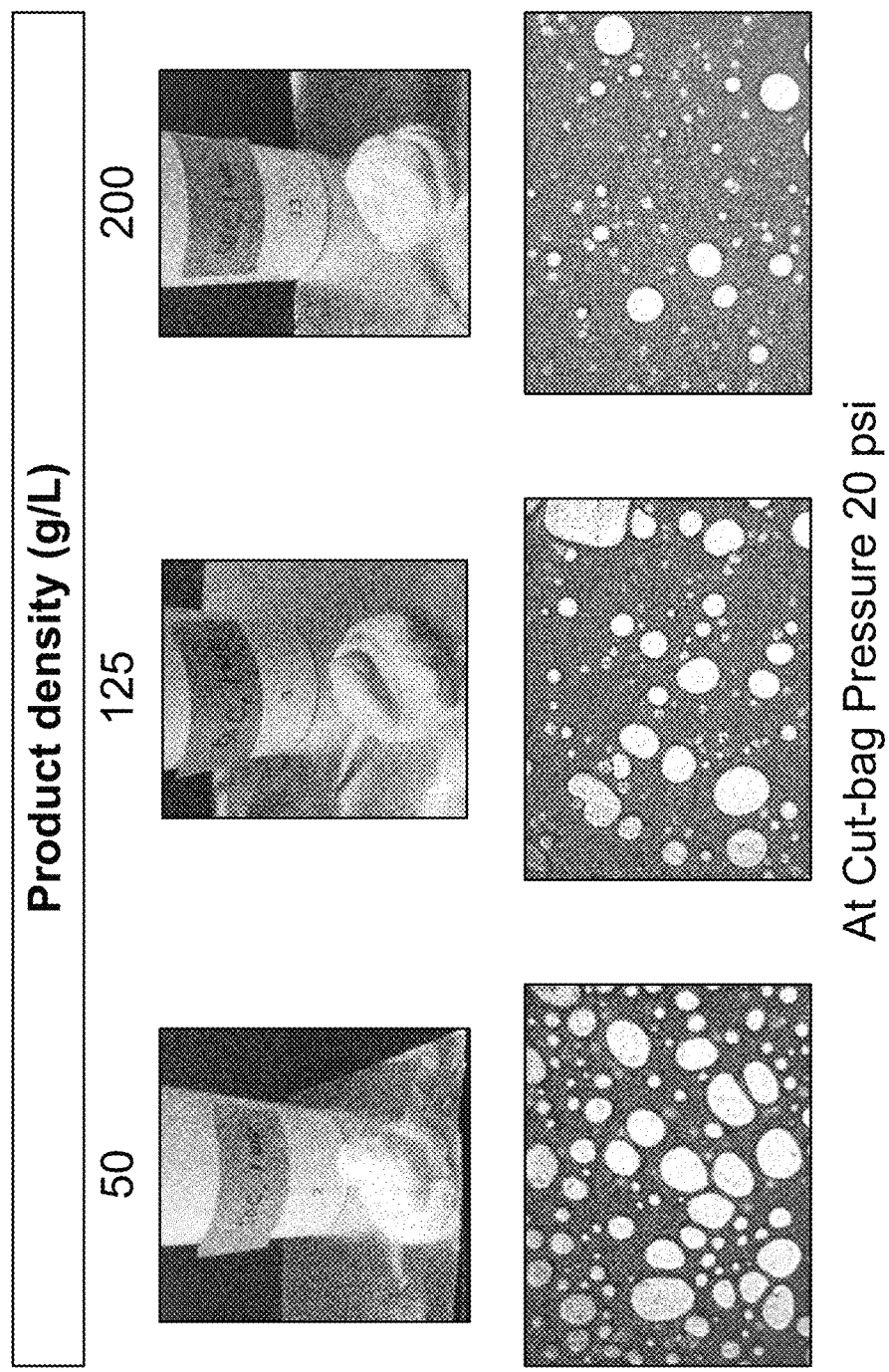
FIG. 7 shows results of high temperature stability (50° C.) at various product densities and at 20 psi cut-bag pressure.
Figure 8:
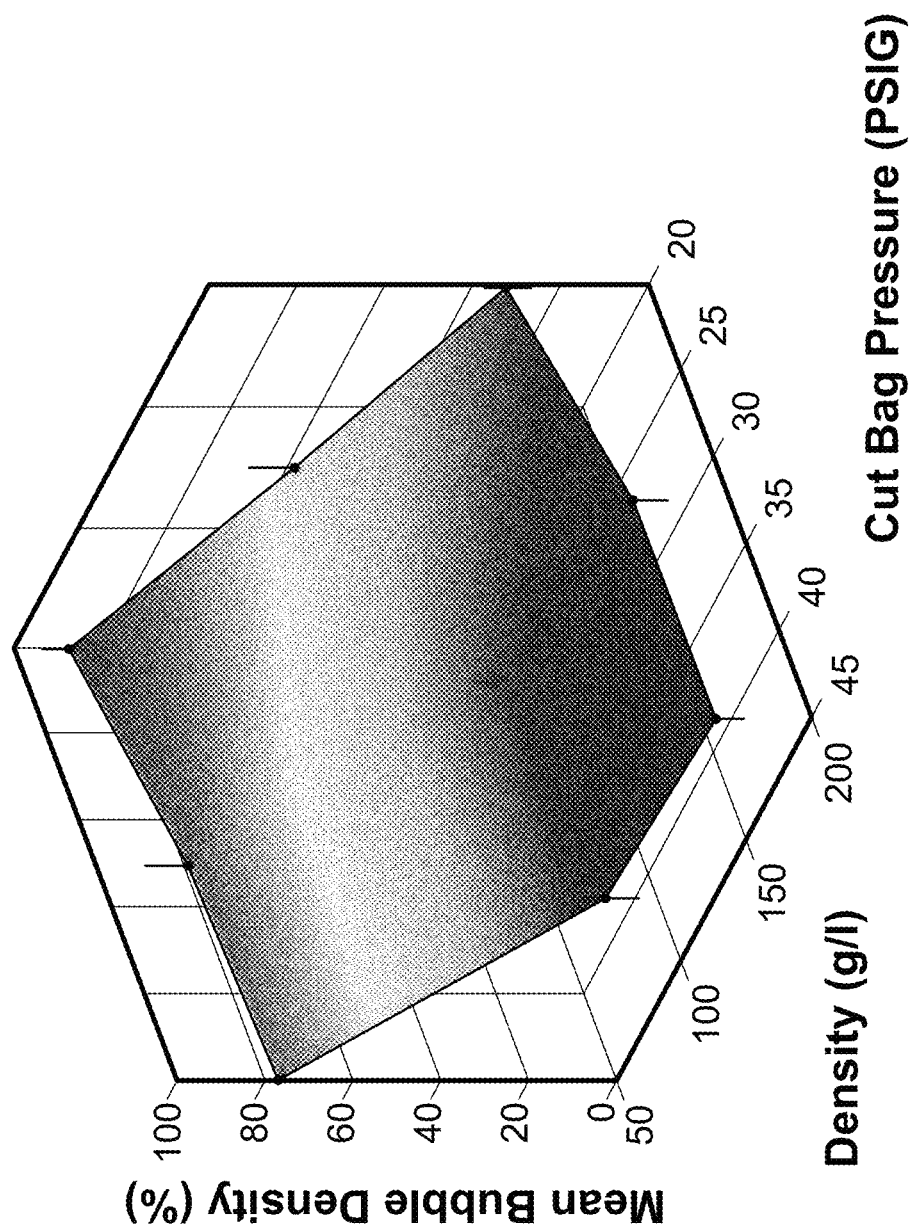
FIG. 8 shows bubble density as at various product densities and cut-bag pressures. Average distribution of bubbles sampled every 0.625 mm through the fluid normalized by total fluid volume.
Figure 9:
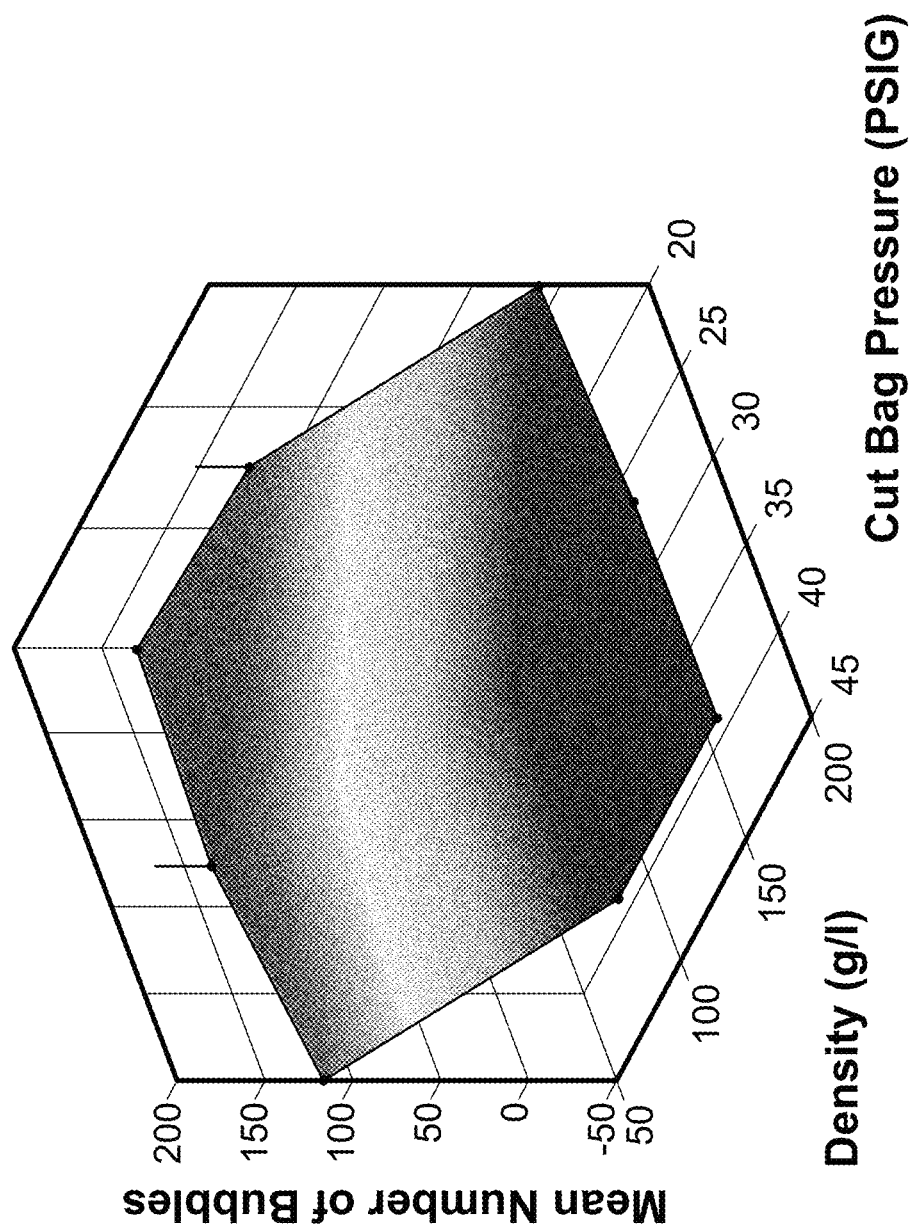
FIG. 9 shows number of bubbles at various product densities and cut-bag pressures. Average distribution of bubbles sampled every 0.625 mm through the fluid normalized by total fluid volume.
Figure 10:
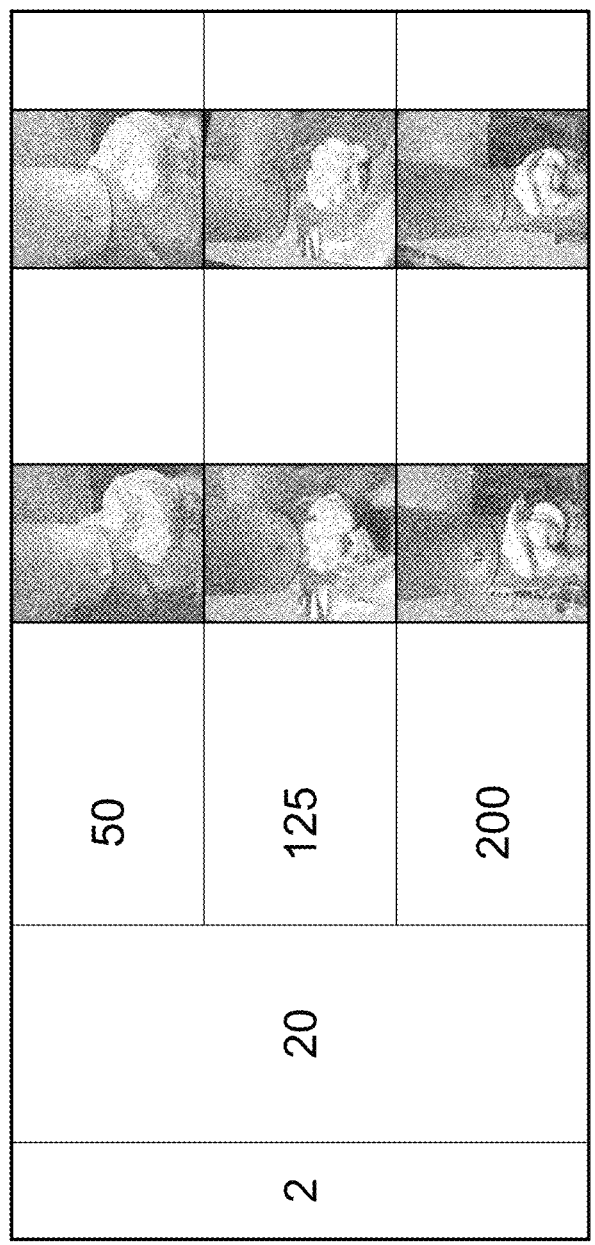
FIG. 10 shows appearances of "whipped-foam" delivered from whipped sunscreen samples manufactured at cut-bag pressure 20 psi with various product densities.
Figure 11:
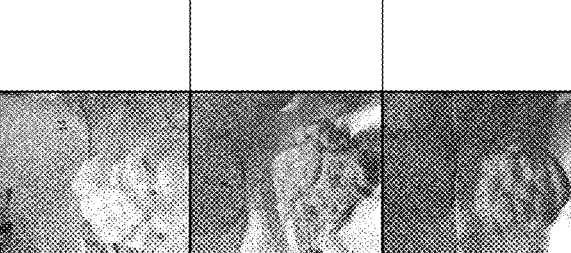
FIG. 11 shows appearances of "whipped-foam" delivered from whipped sunscreen samples manufactured at cut-bag pressure 32.5 psi with various product densities.
Figure 11:
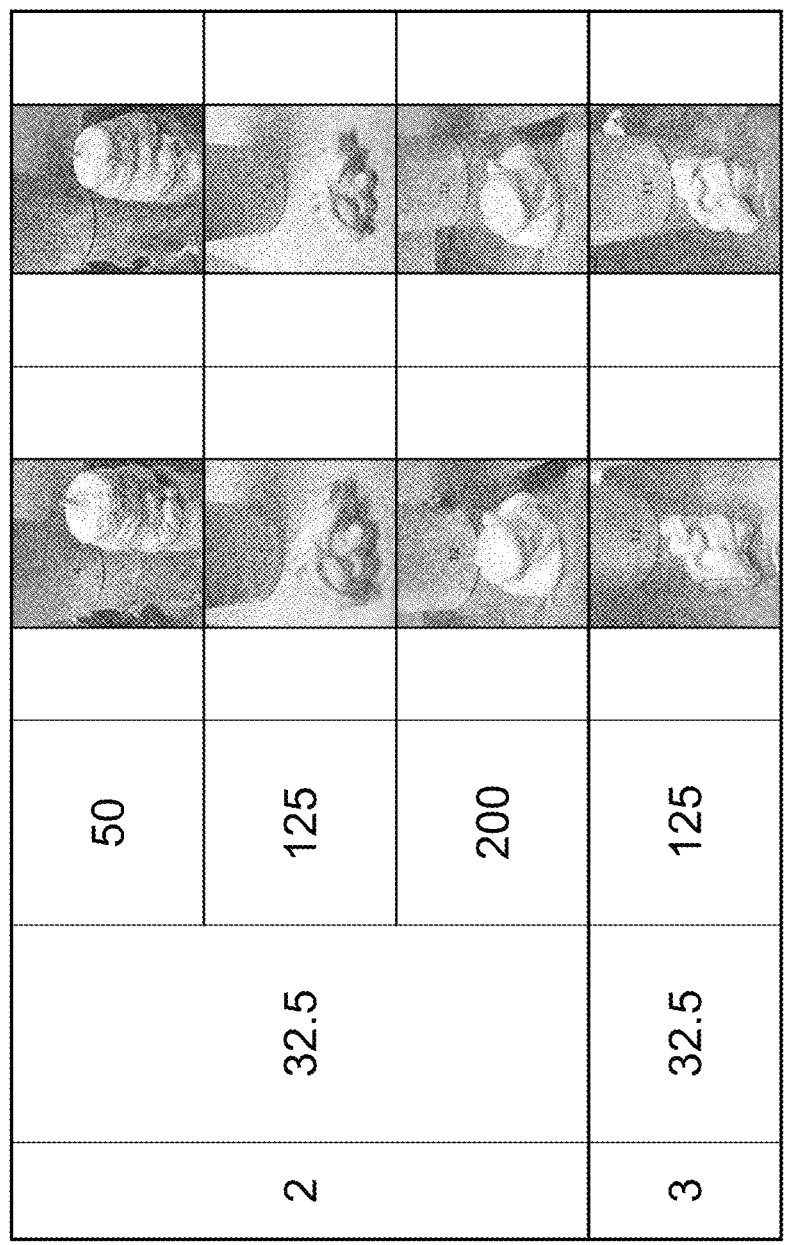
Figure 12:
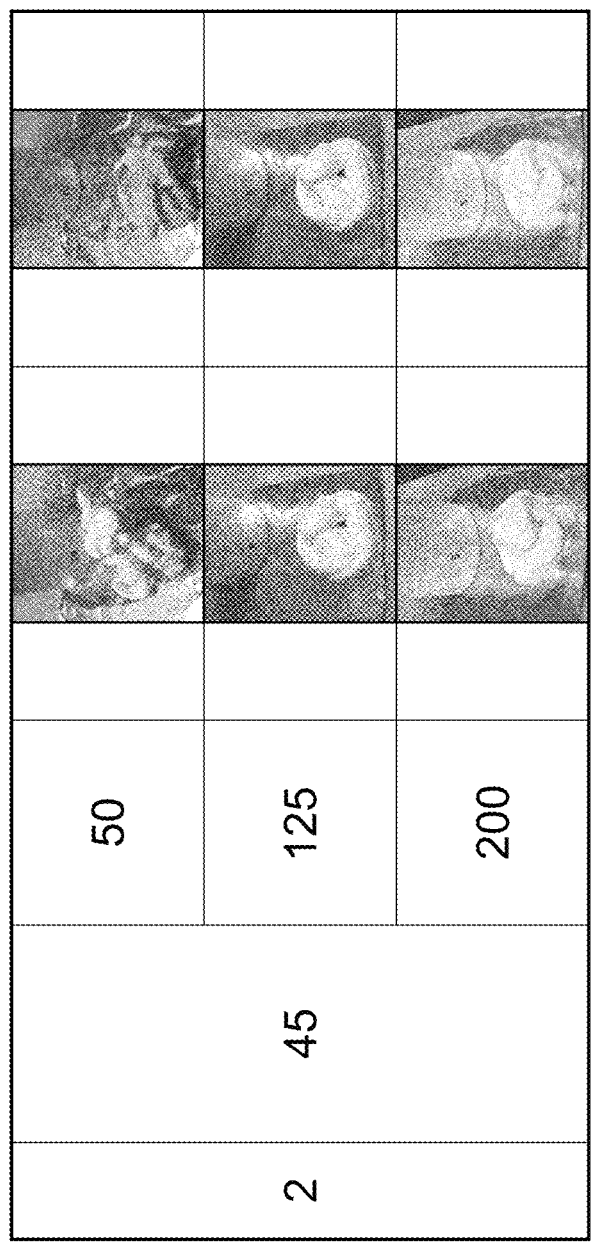
FIG. 12 shows appearances of "whipped-foam" delivered from whipped sunscreen samples manufactured at cut-bag pressure 45 psi with various product densities.
Figure 13:
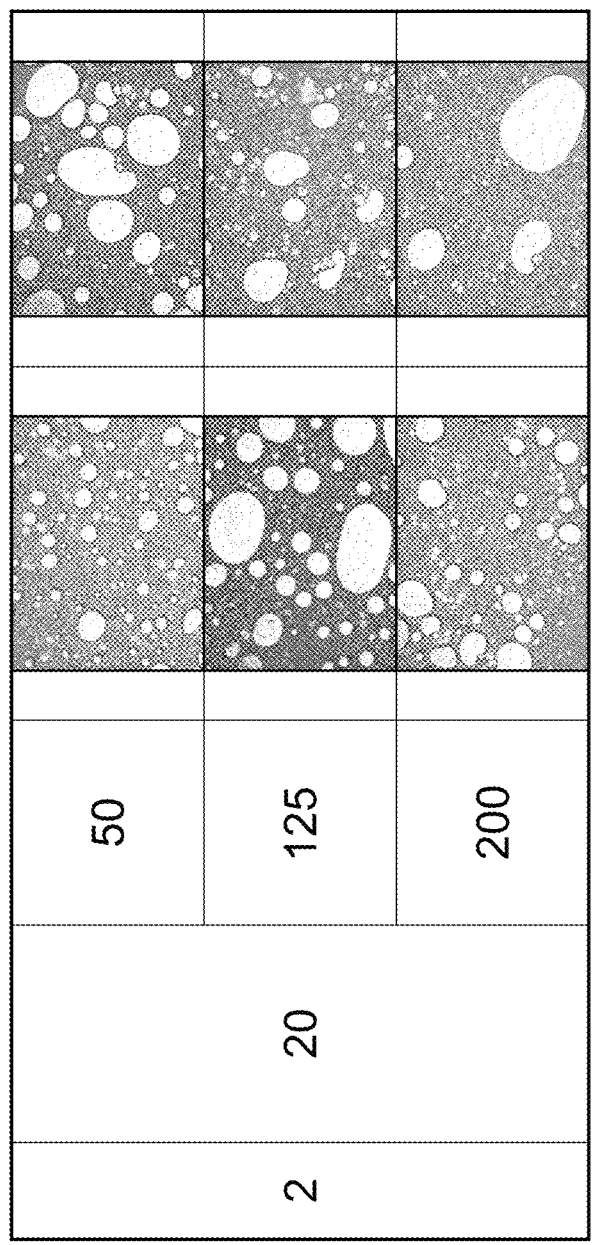
FIG. 13 Photomicrographs (at 500× magnification): Images of gas bubbles ($N_2O$) in "whipped-foam" delivered from whipped sunscreen samples manufactured at cut-bag pressure 20 psi with various product densities.
Figure 14:
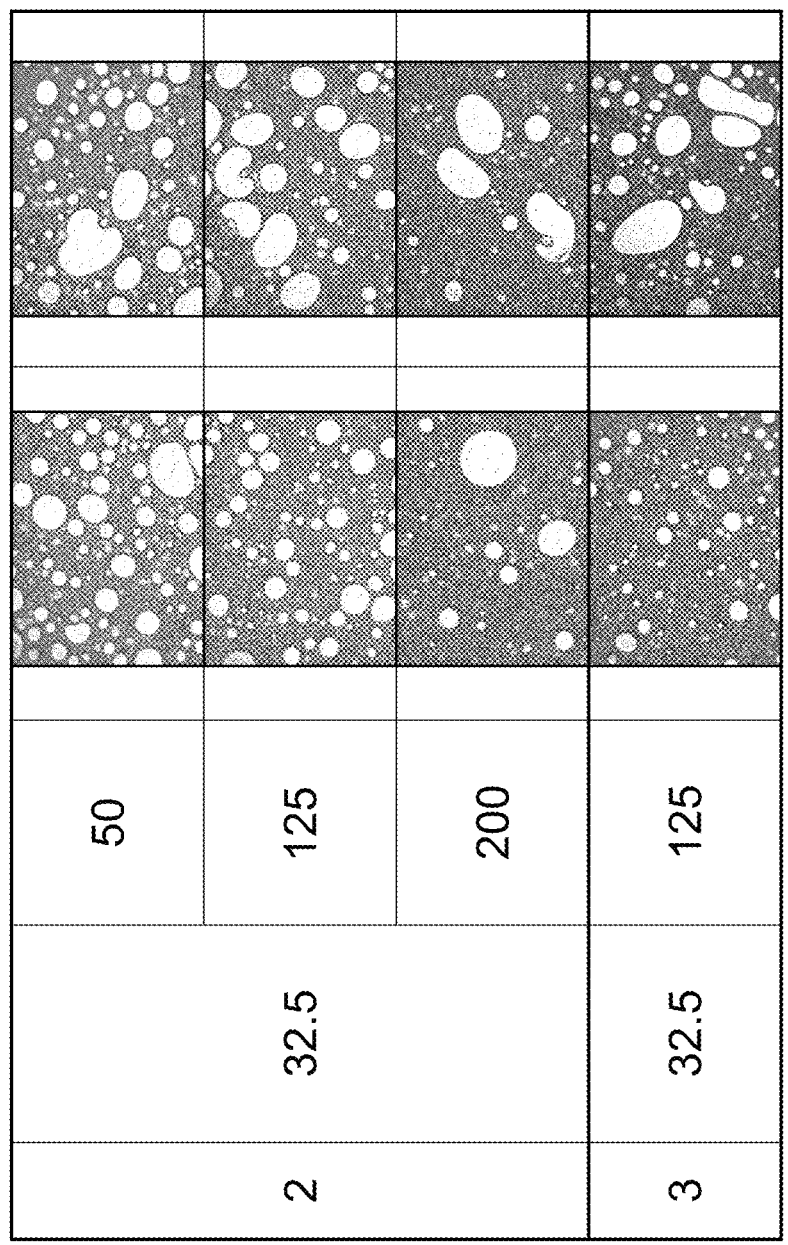
FIG. 14 Photomicrographs (at 500× magnification): Images of gas bubbles ($N_2O$) in "whipped-foam" delivered from whipped sunscreen samples manufactured at cut-bag pressure 32.5 psi with various product densities.
Figure 15:
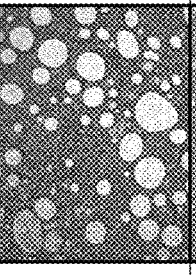
FIG. 15 Photomicrographs (at 500× magnification): Images of gas bubbles ($N_2O$) in "whipped-foam" delivered from whipped sunscreen samples manufactured at cut-bag pressure 45 psi with various product densities.
Figure 15:
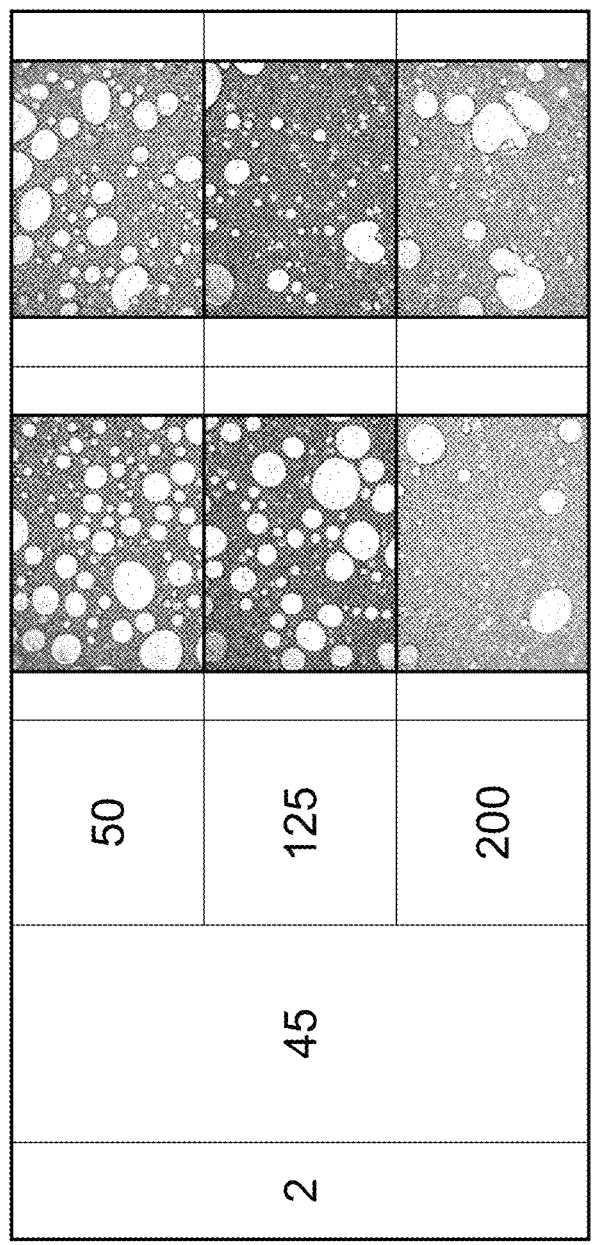
Figure 16:
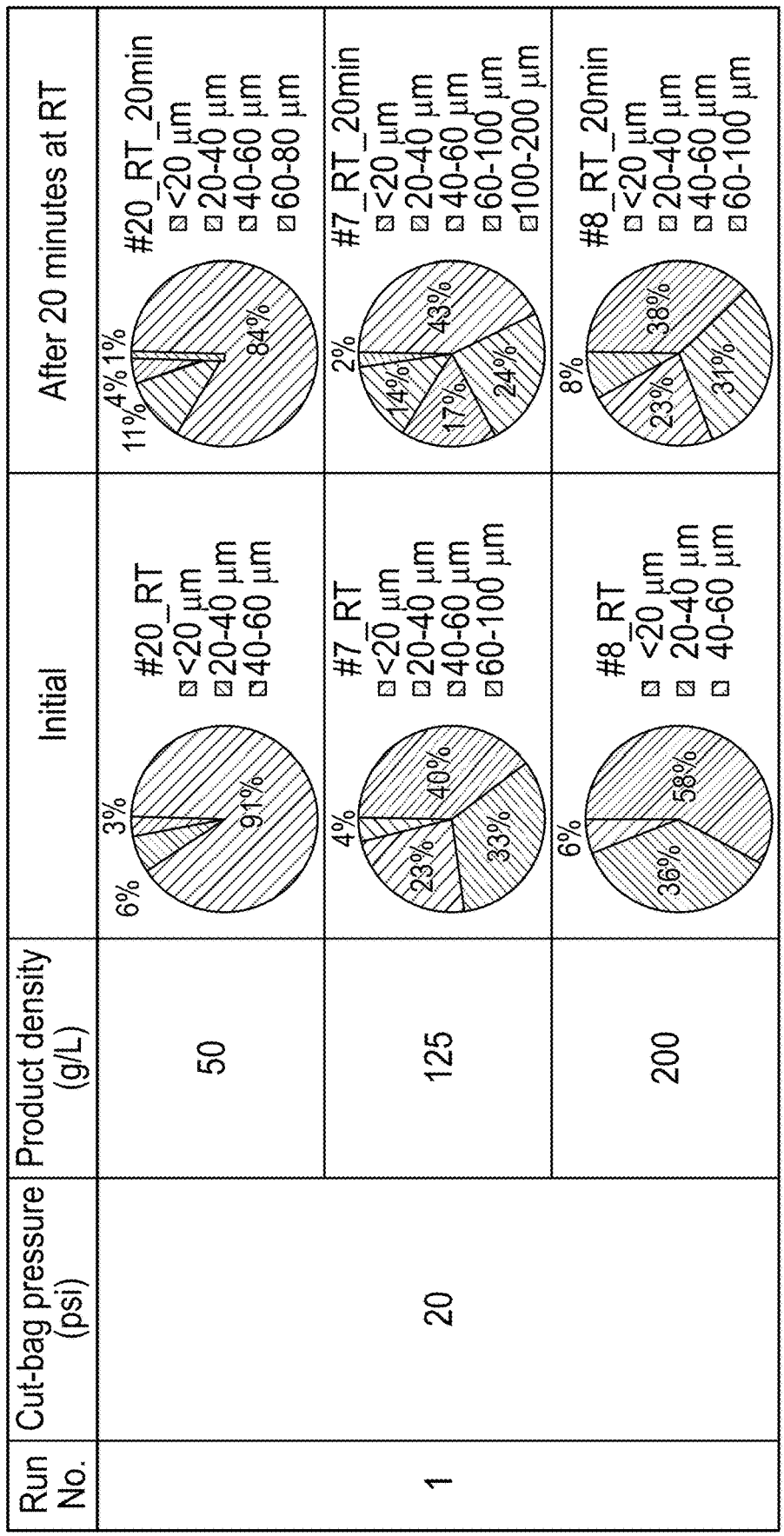
FIG. 16 Distribution of gas bubbles ($N_2O$) in photomicrographs (at 500× magnification) for "whipped-foam" delivered from whipped sunscreen samples manufactured at cut-bag pressure 20 psi with various product densities.
Figure 16:
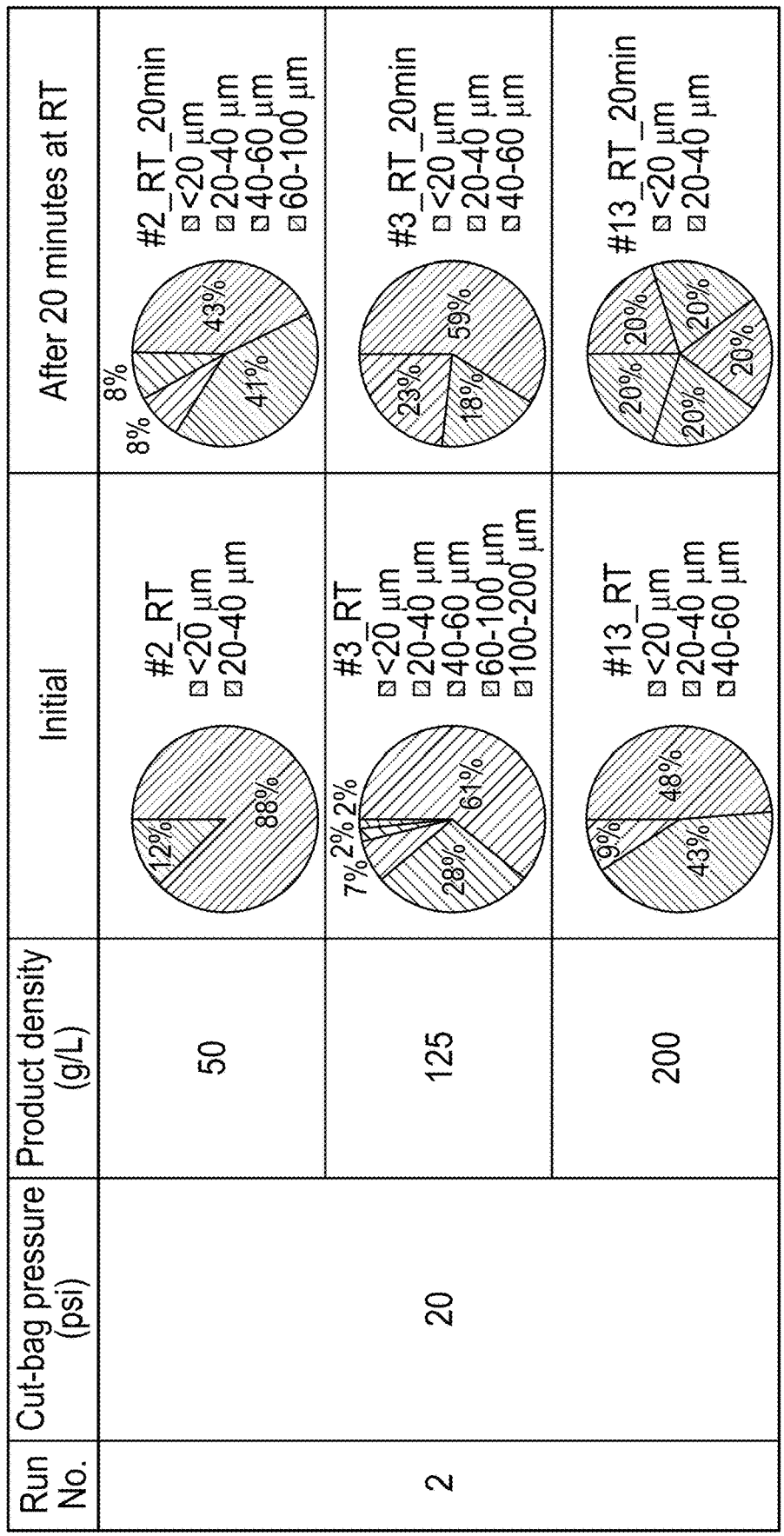
Figure 17:
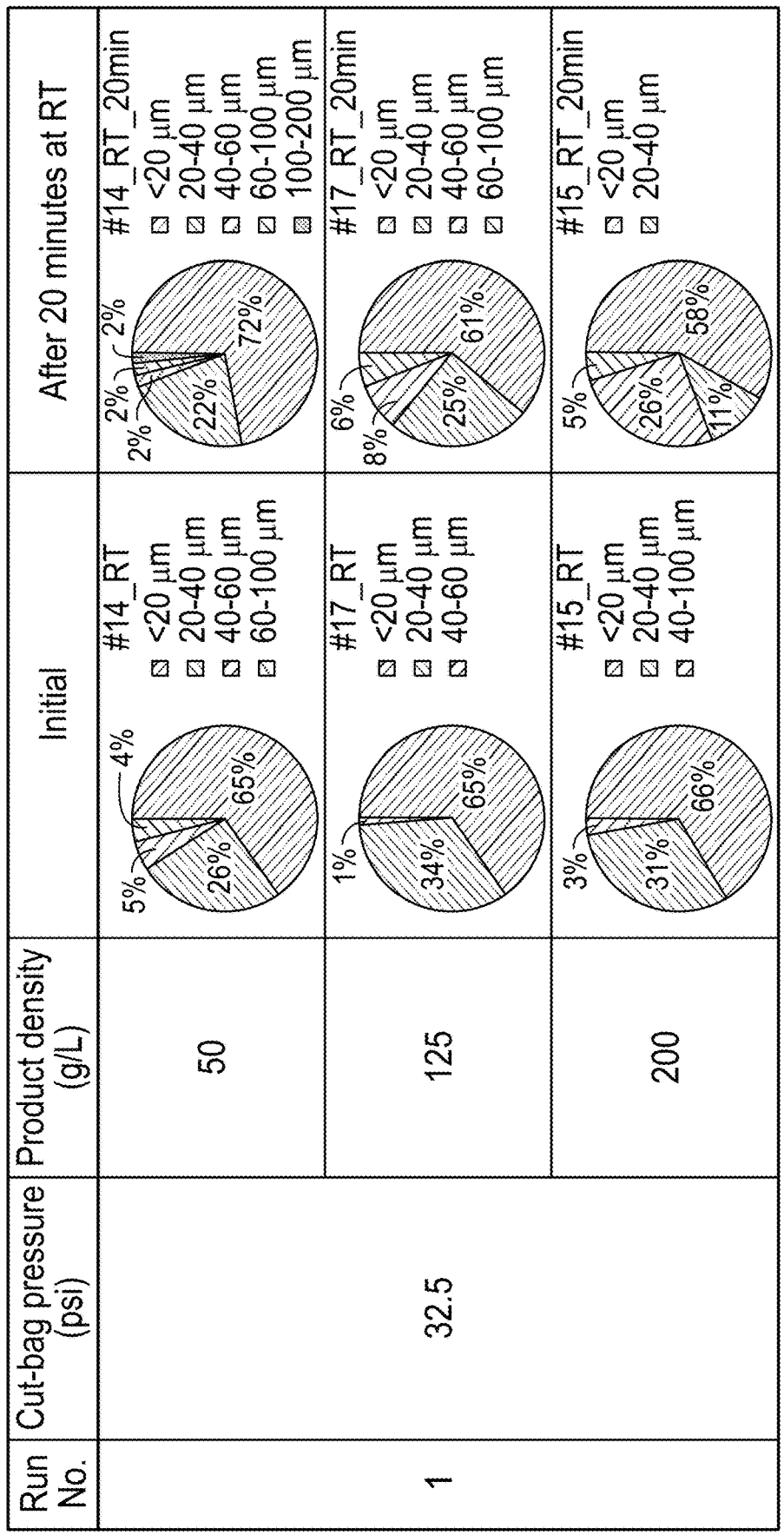
FIG. 17 Distribution of gas bubbles ($N_2O$) in photomicrographs (at 500× magnification) for "whipped-foam" delivered from whipped sunscreen samples manufactured at cut-bag pressure 32.5 psi with various product densities.
Figure 17:
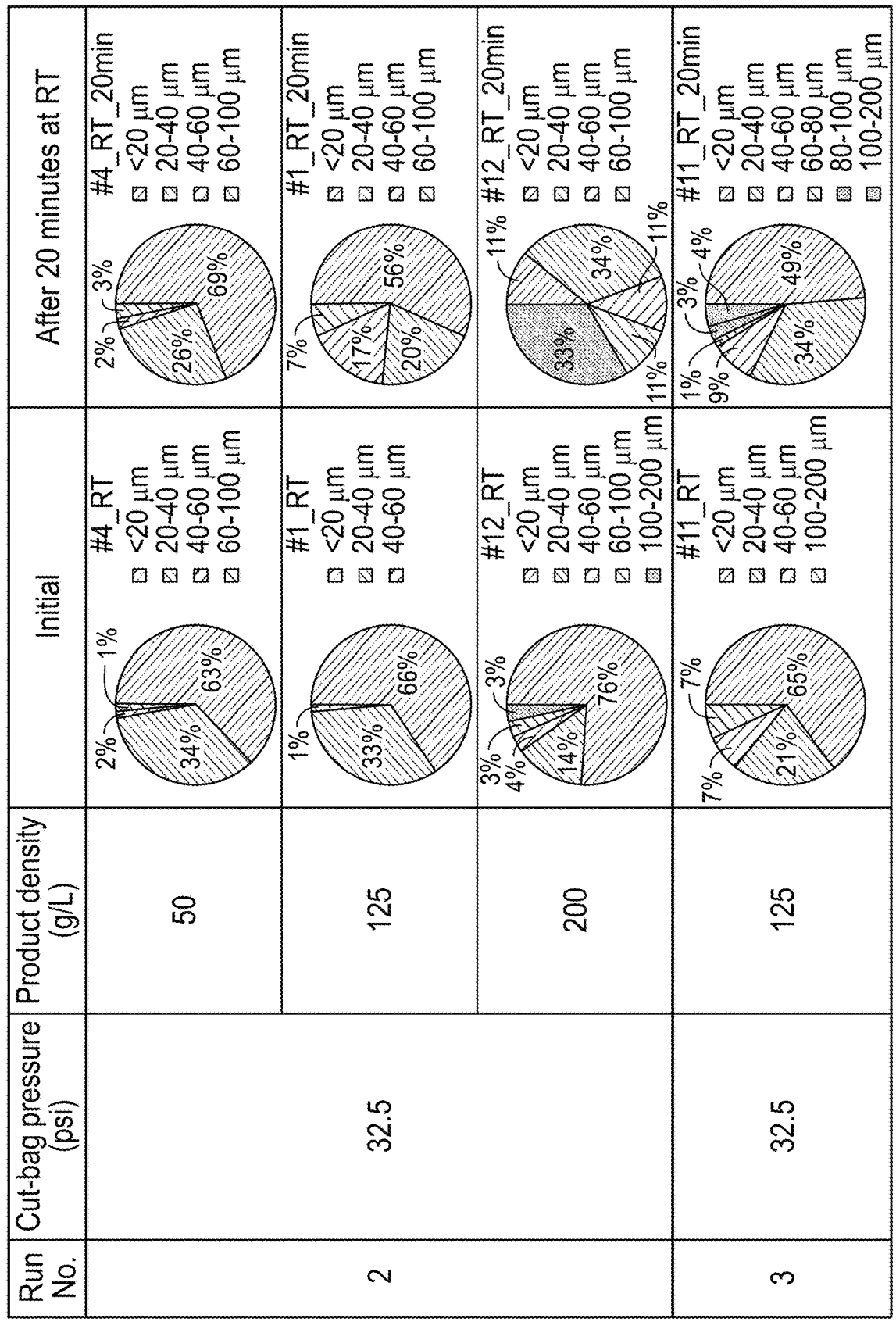
Figure 18:
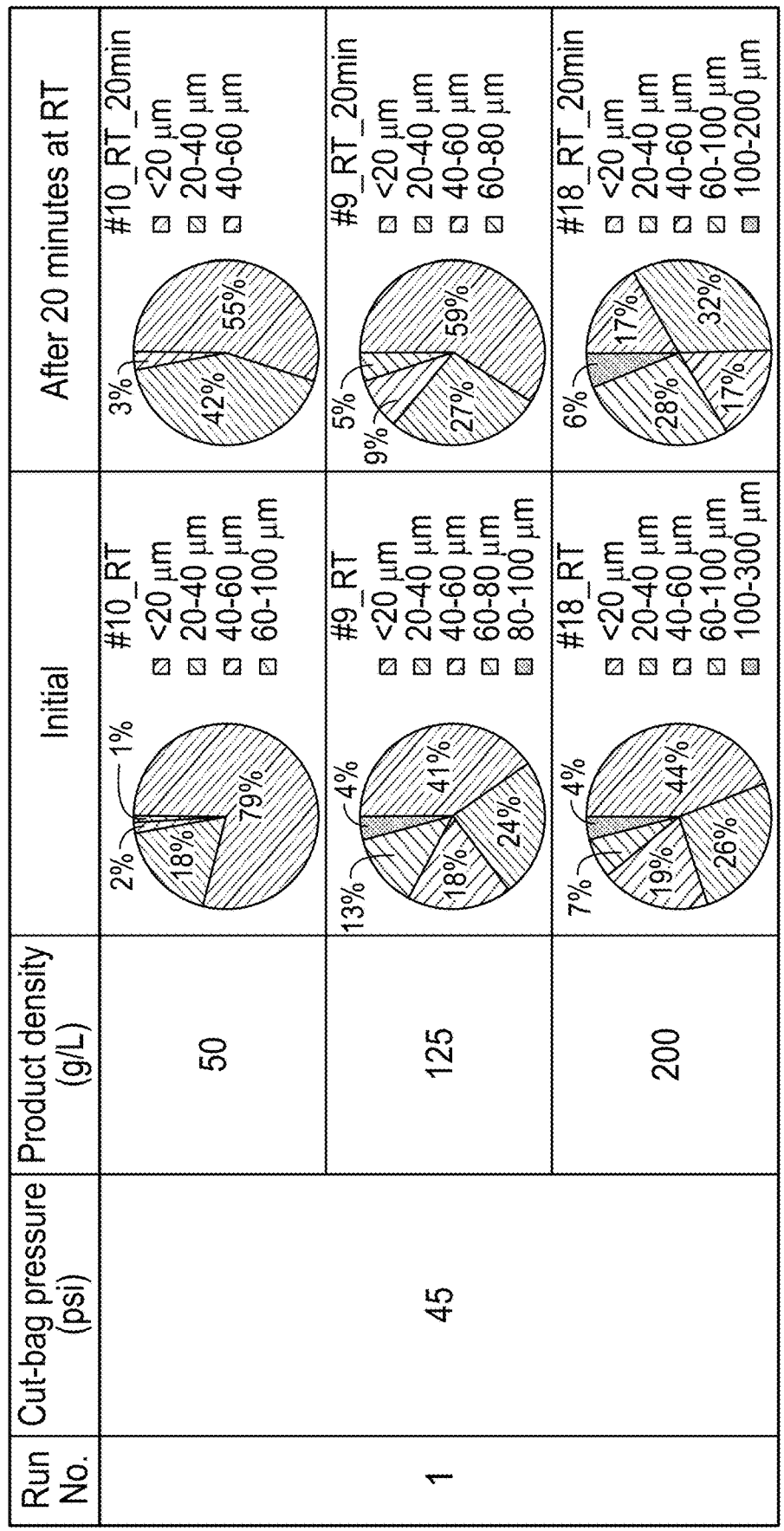
FIG. 18 Distribution of gas bubbles ($N_2O$) in photomicrographs (at 500× magnification) for "whipped-foam" delivered from whipped sunscreen samples manufactured at cut-bag pressure 45 psi with various product densities.
Figure 18:
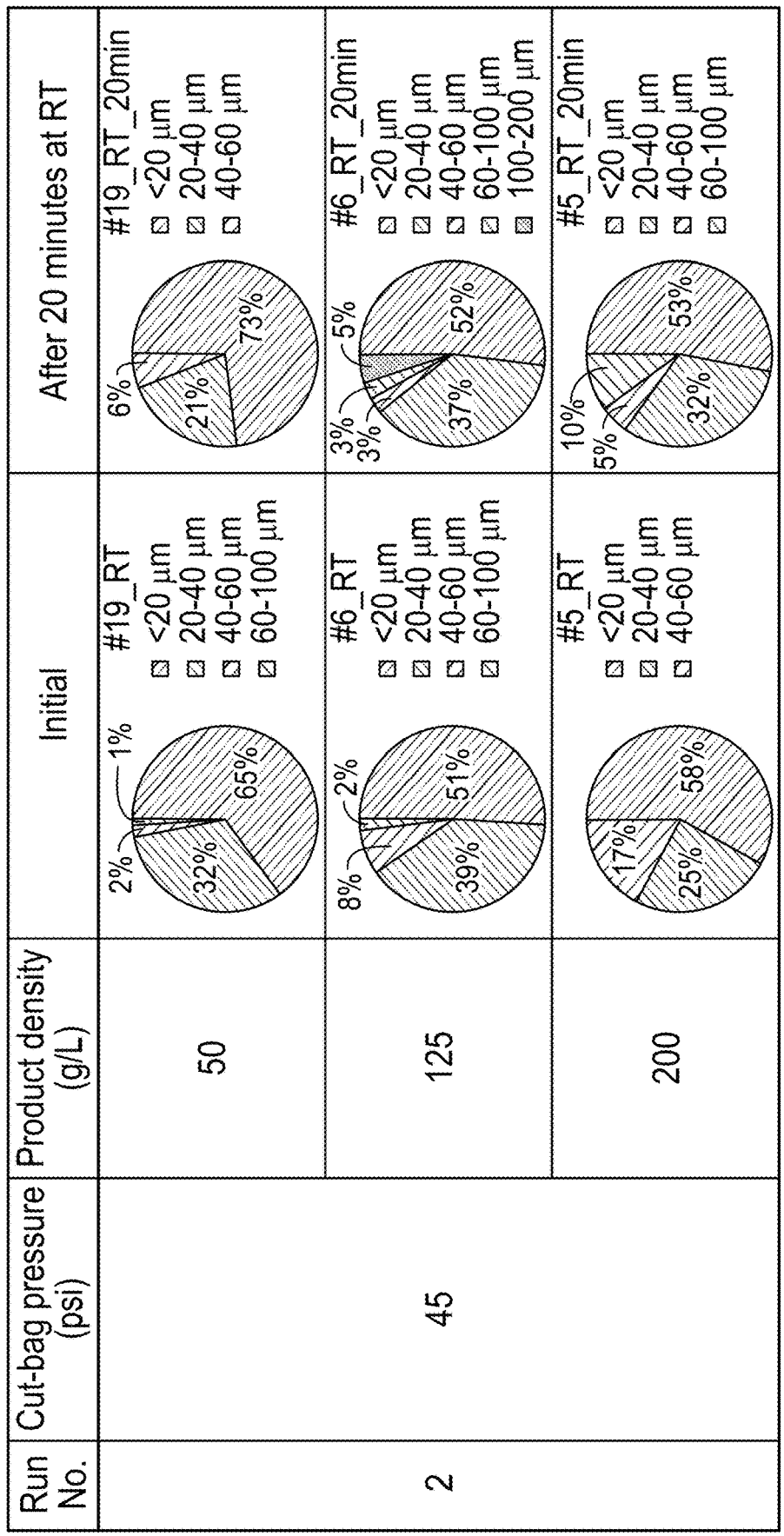
Figure 19:
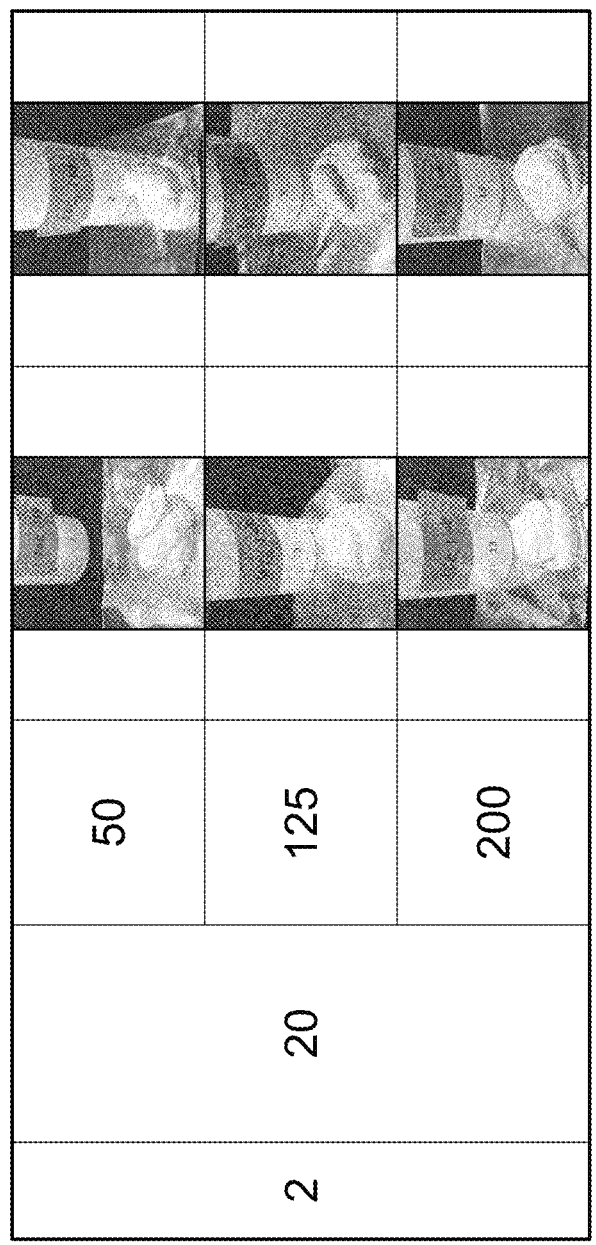
FIG. 19 Appearances and stabilities of "whipped-foam" delivered from whipped sunscreen lotion samples (manufactured at cut-bag pressure 20 psi with various product densities), which had been stored at 50° C./75% RH for 1 week. *T=0 pictures were taken right after pulling out the samples from 50° C./75% RH storage condition and the temperature of each sample was close to 50° C. when the 'whipped-foam" was dispensed; T=2 min pictures taken 2 minutes later.
Figure 20:
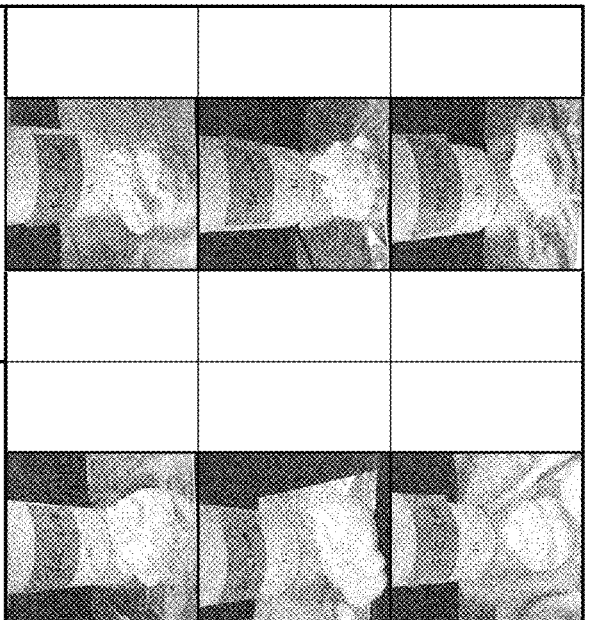
FIG. 20 Appearances and stabilities of "whipped-foam" delivered from whipped sunscreen lotion samples (manufactured at cut-bag pressure 32.5 psi with various product densities), which had been stored at 50° C./75% RH for 1 week. *T=0 pictures were taken right after pulling out the samples from 50° C./75% RH storage condition and the temperature of each sample was close to 50° C. when the 'whipped-foam" was dispensed; T=2 min pictures taken 2 minutes later.
Figure 20:
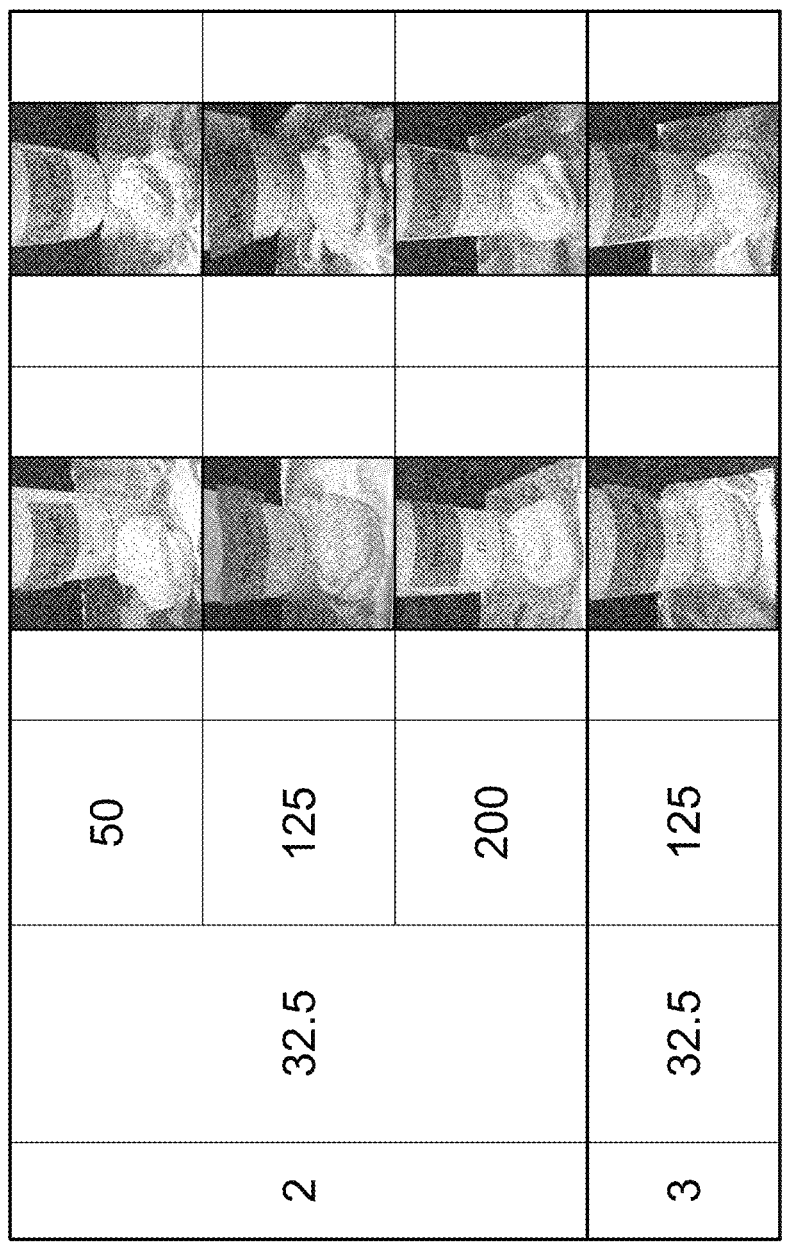
Figure 21:
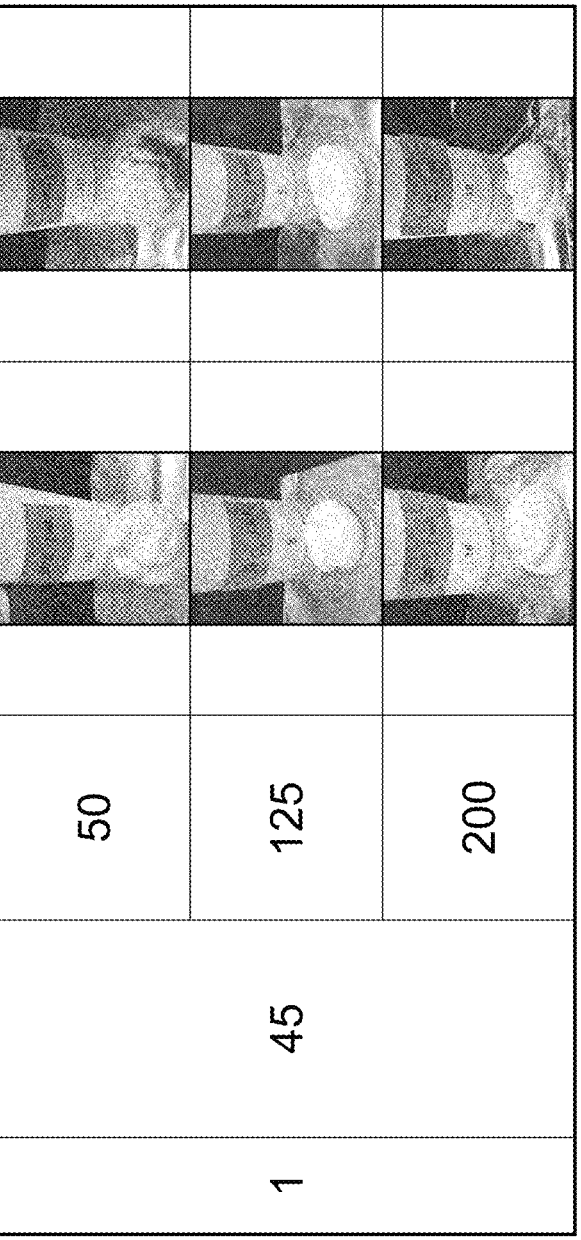
FIG. 21 Appearances and stabilities of "whipped-foam" delivered from whipped sunscreen lotion samples (manufactured at cut-bag pressure 45 psi with various product densities), which had been stored at 50° C./75% RH for 1 week. *T=0 pictures were taken right after pulling out the samples from 50° C./75% RH storage condition and the temperature of each sample was close to 50° C. when the 'whipped-foam" was dispensed; T=2 min pictures taken 2 minutes later.
Figure 21:
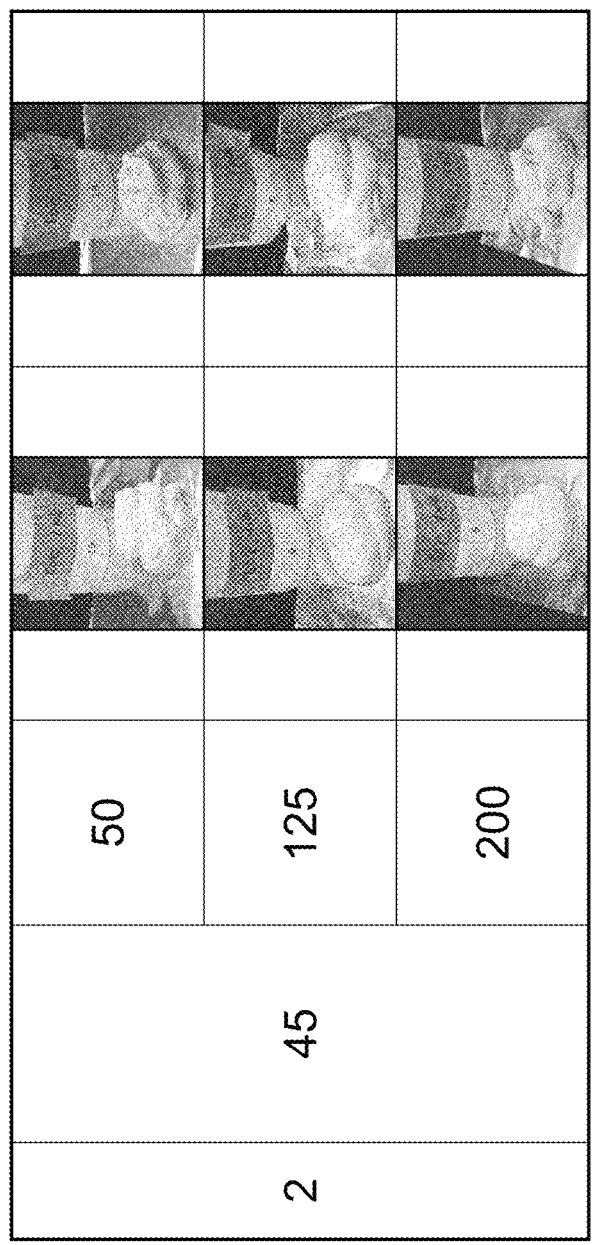
Figure 22:
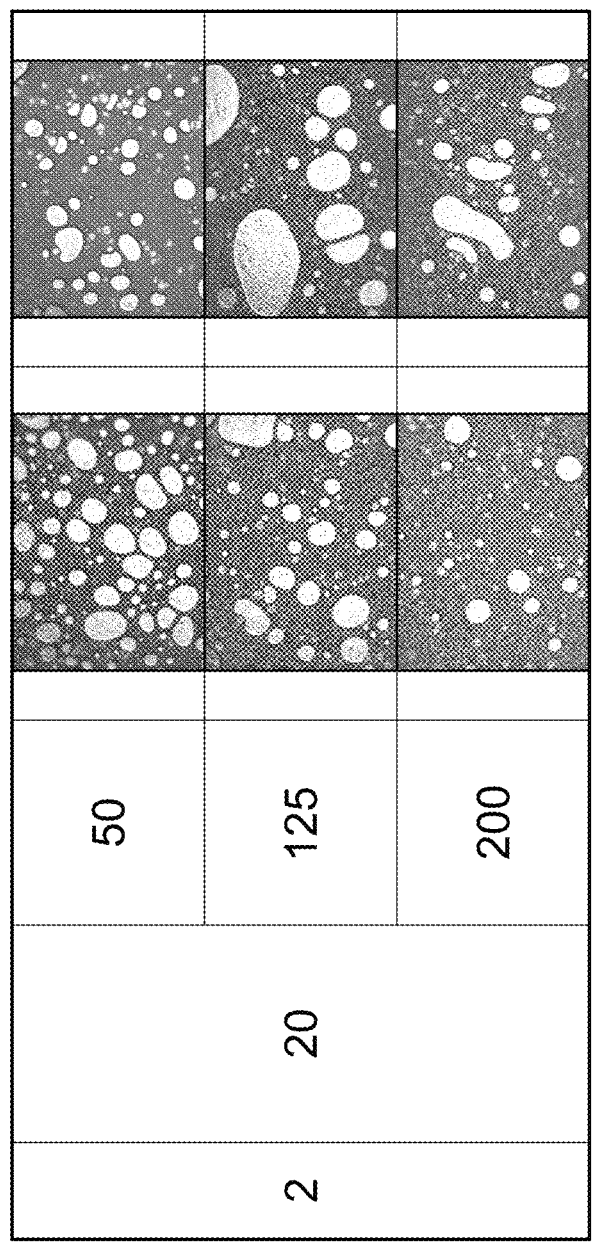
FIG. 22 Photomicrograph (at 500× magnification): Images of gas bubbles ($N_2O$) in "whipped-foam" delivered from whipped sunscreen lotion samples (manufactured at cut-bag pressure 20 psi with various product densities), which had been stored at 50° C./75% RH for 1 week.
Figure 23:
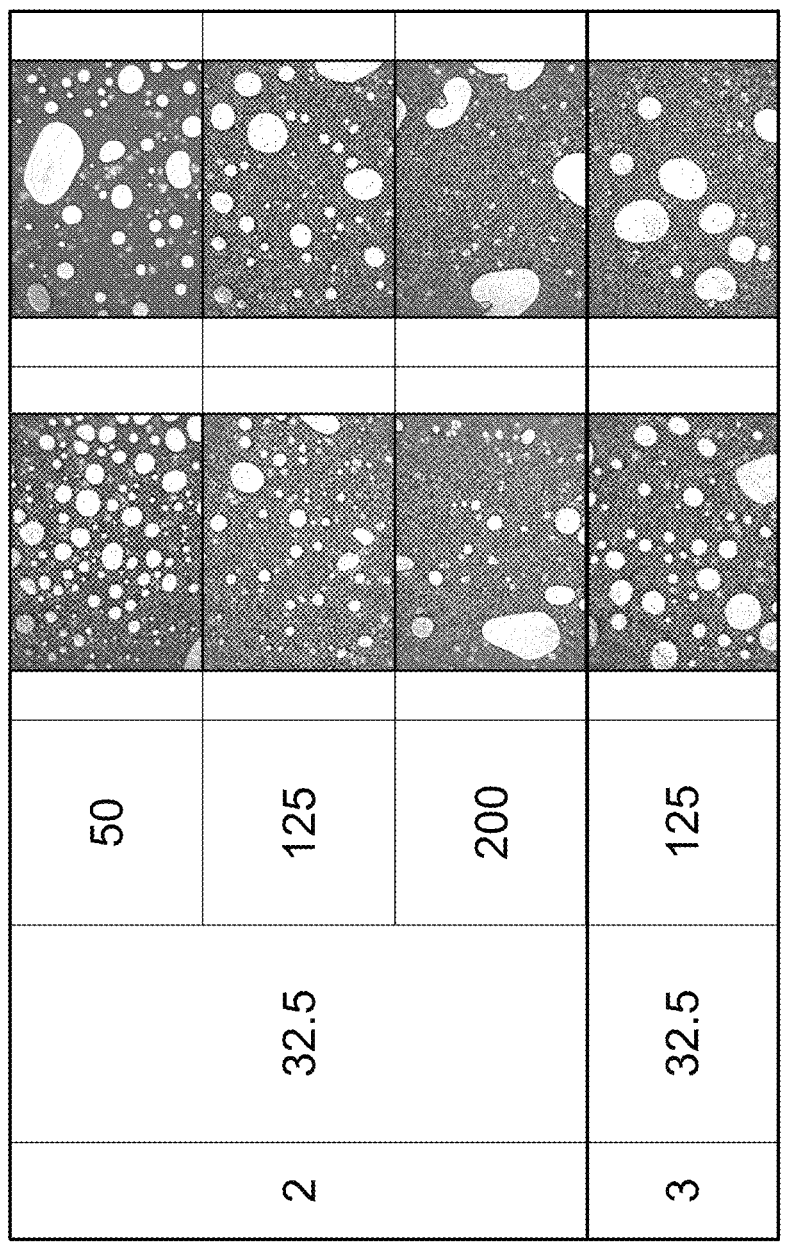
FIG. 23 Photomicrograph (at 500× magnification): Images of gas bubbles ($N_2O$) in "whipped-foam" delivered from whipped sunscreen lotion samples (manufactured at cut-bag pressure 32.5 psi with various product densities), which had been stored at 50° C./75% RH for 1 week.
Figure 24:
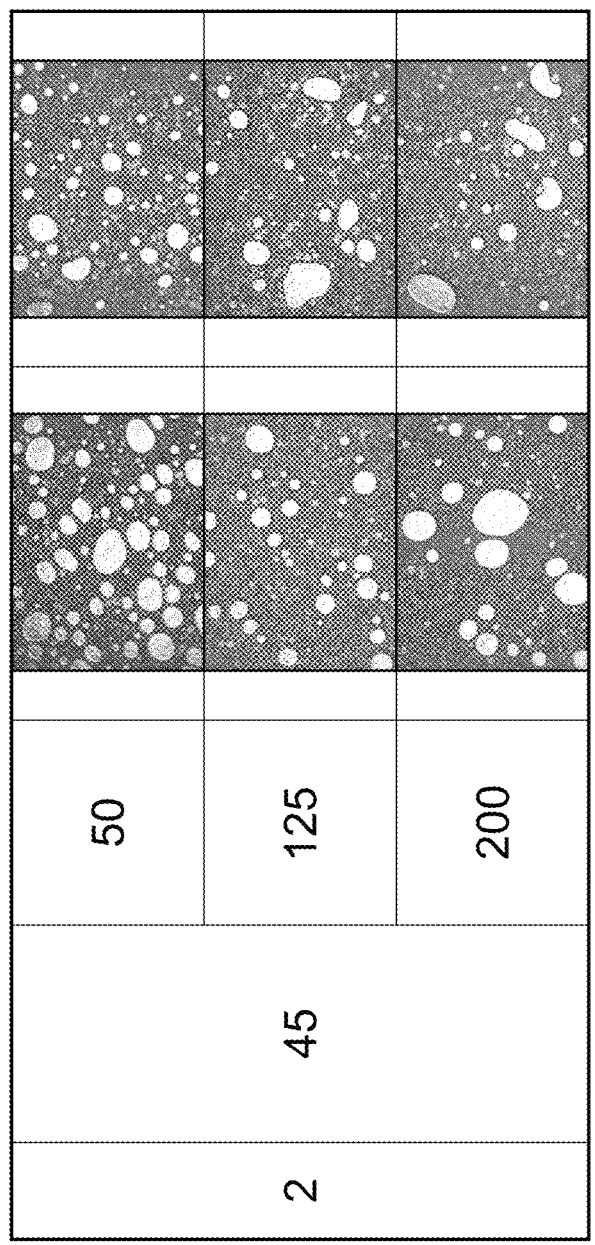
FIG. 24 Photomicrograph (at 500× magnification): Images of gas bubbles ($N_2O$) in "whipped-foam" delivered from whipped sunscreen lotion samples (manufactured at cut-bag pressure 45 psi with various product densities), which had been stored at 50° C./75% RH for 1 week.
Figure 25:
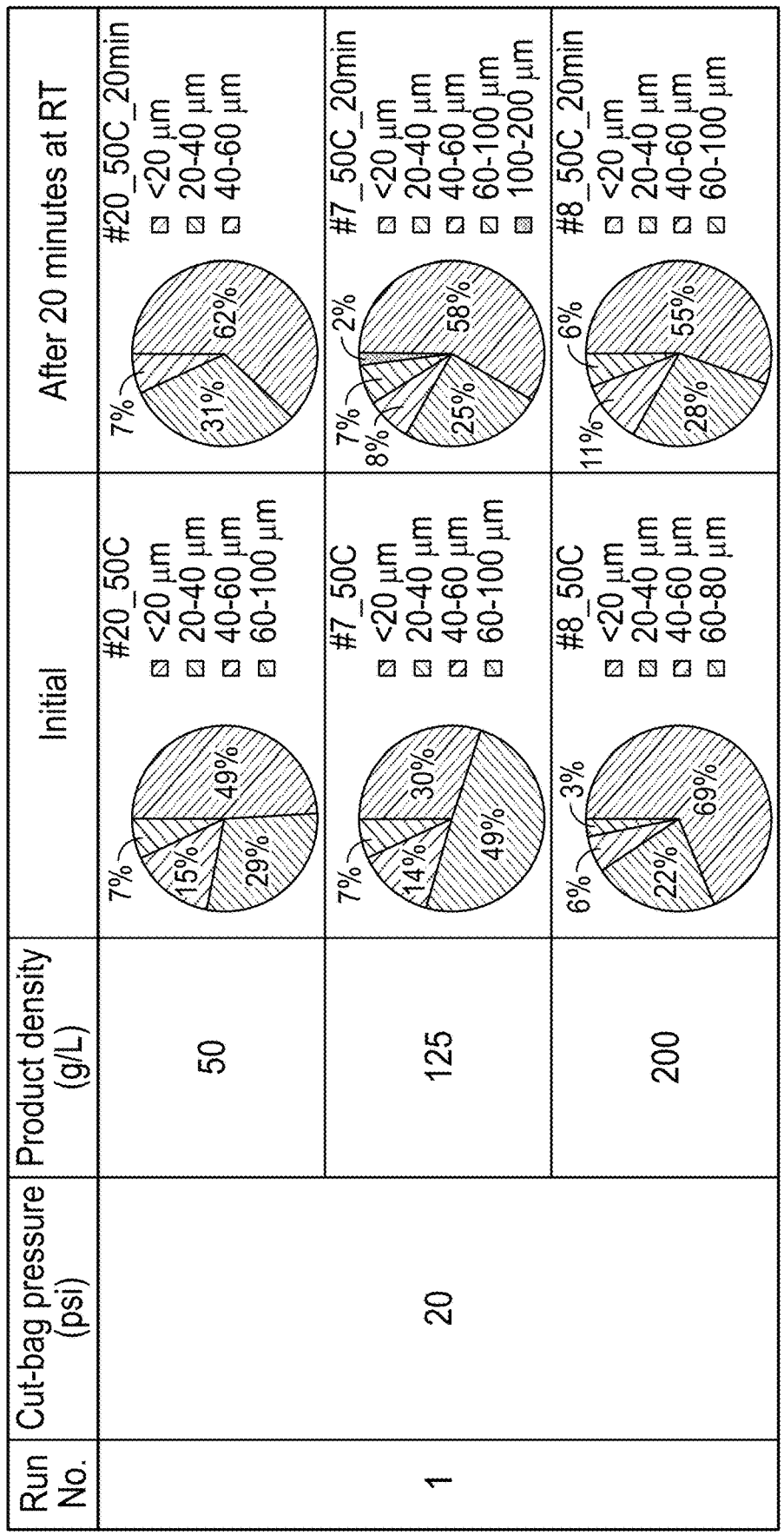
FIG. 25 Distribution of gas bubbles ($N_2O$) in photomicrographs (at 500× magnification) for "whipped-foam" delivered from whipped sunscreen samples (manufactured at cut-bag pressure 20 psi with various product densities), which had been stored at 50° C./75% rh for 1 week.
Figure 25:
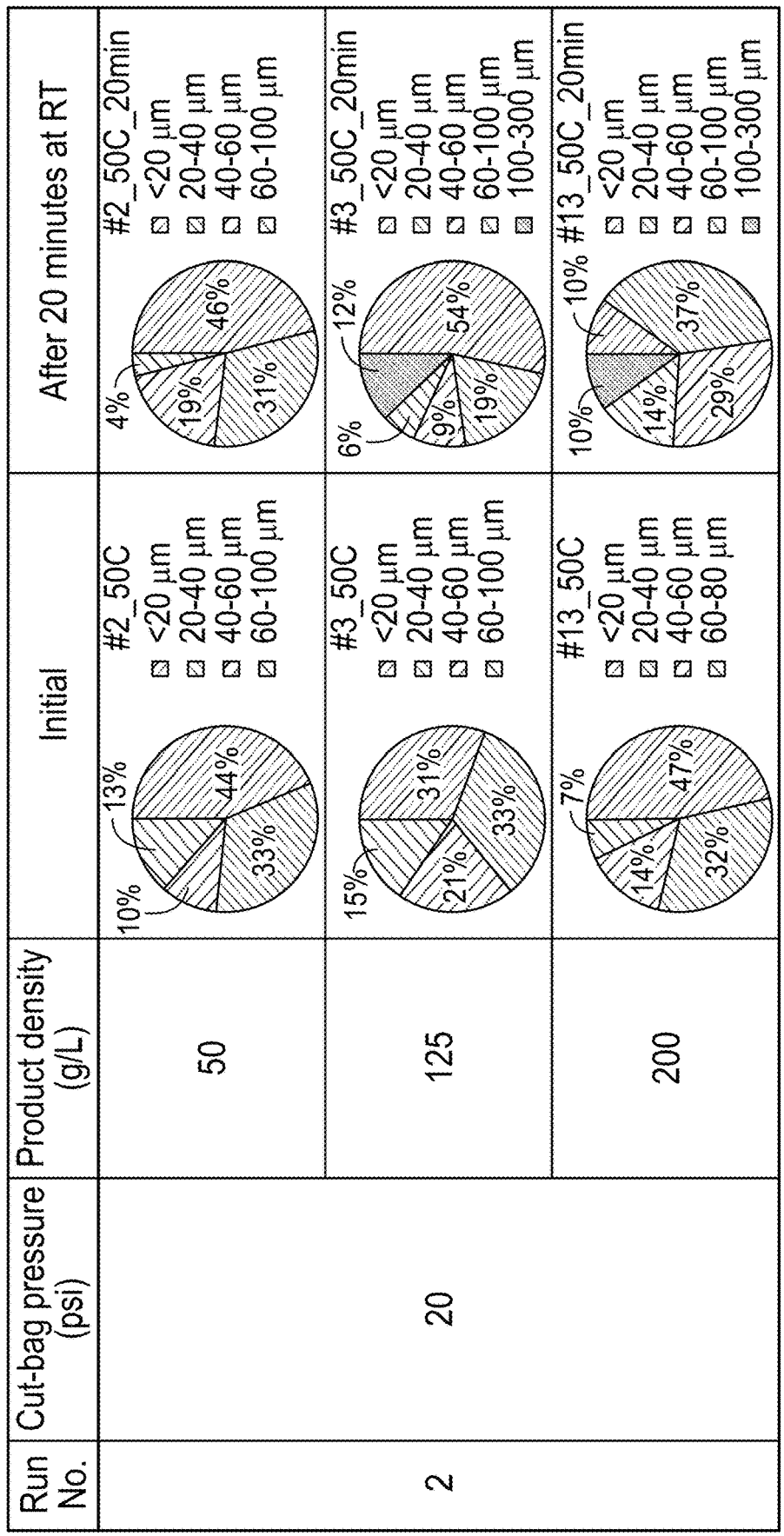
Figure 26:
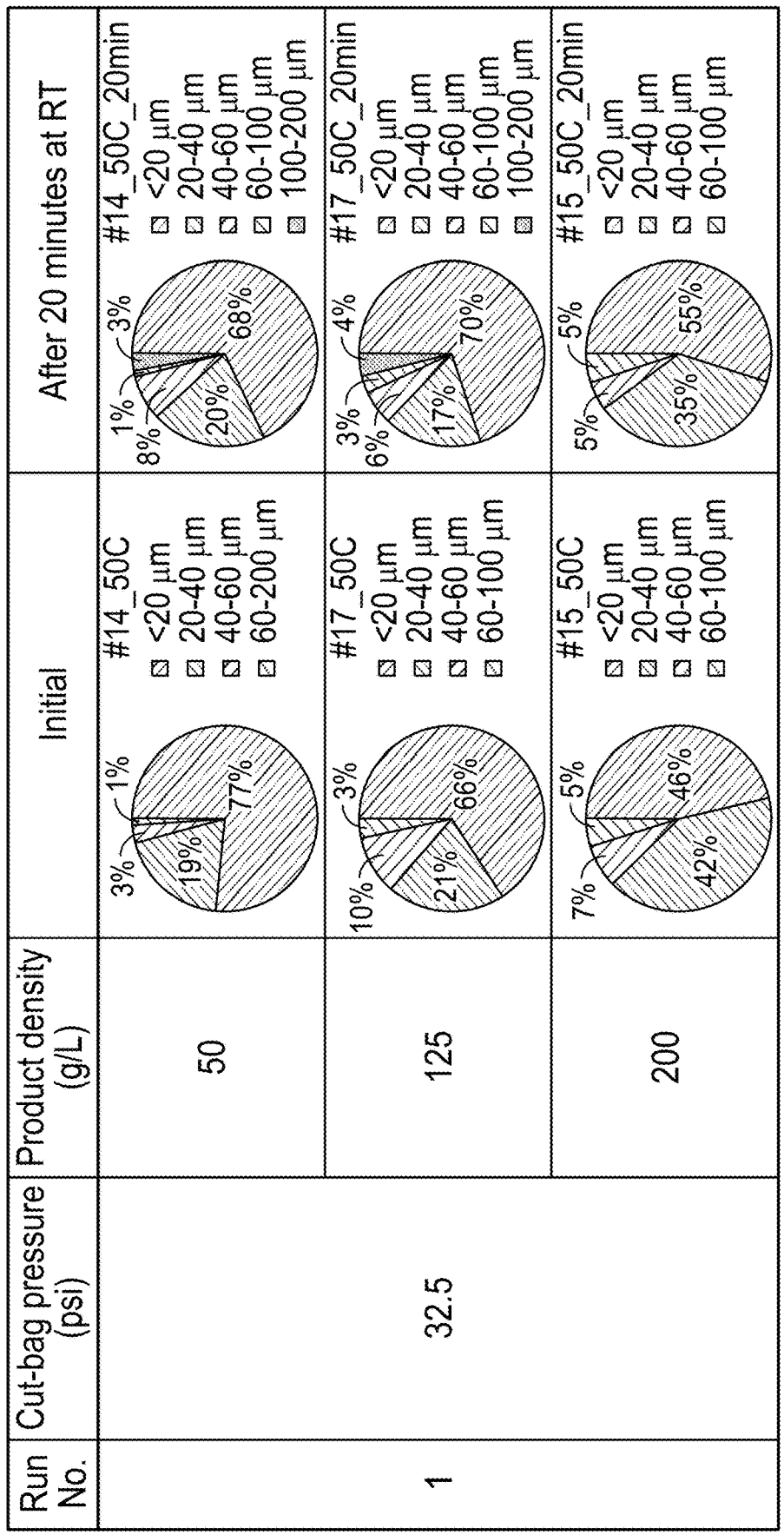
FIG. 26 Distribution of gas bubbles ($N_2O$) in photomicrographs (at 500× magnification) for "whipped-foam" delivered from whipped sunscreen samples (manufactured at cut-bag pressure 32.5 psi with various product densities), which had been stored at 50° C./75% RH for 1 week.
Figure 26:
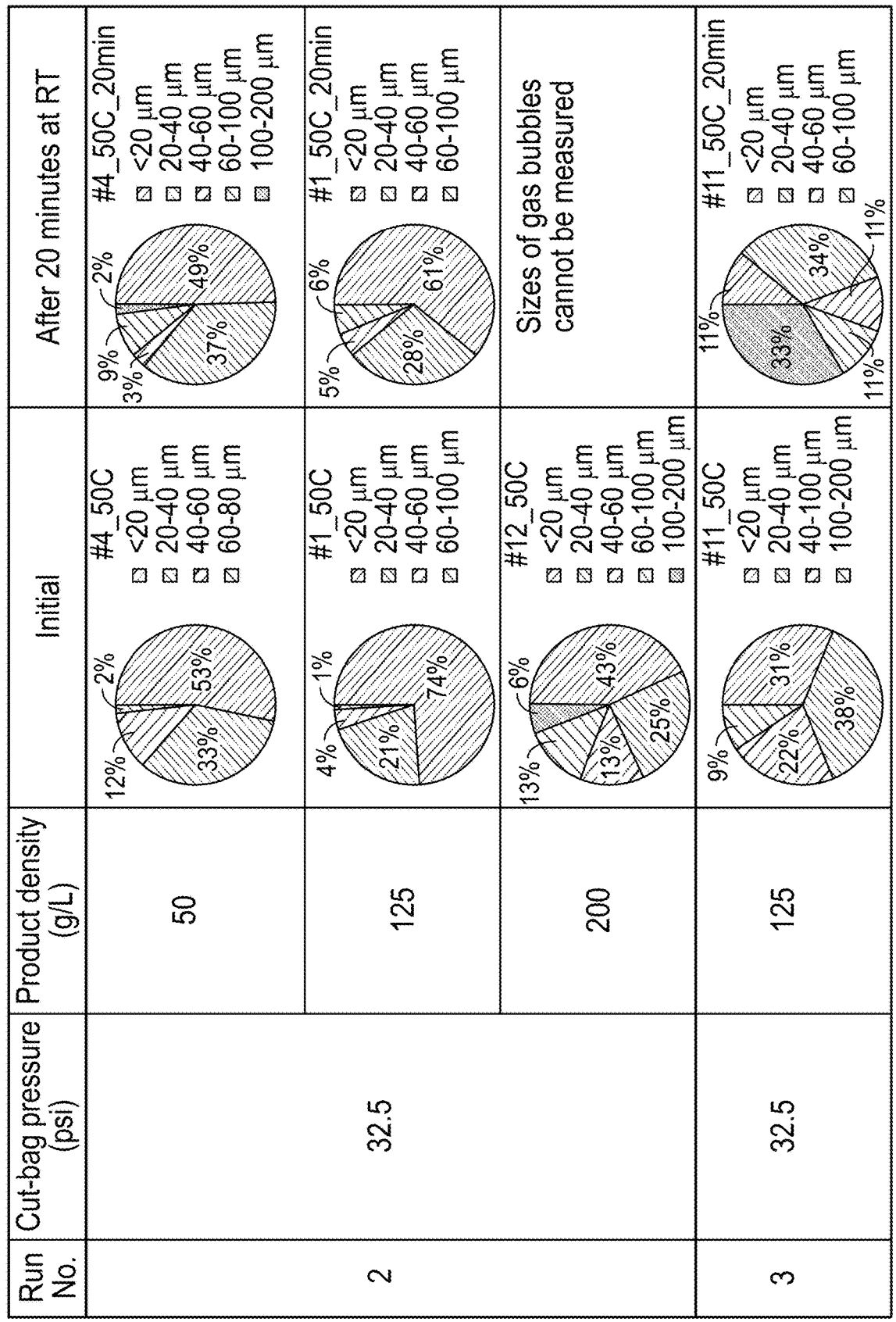
Figure 27:
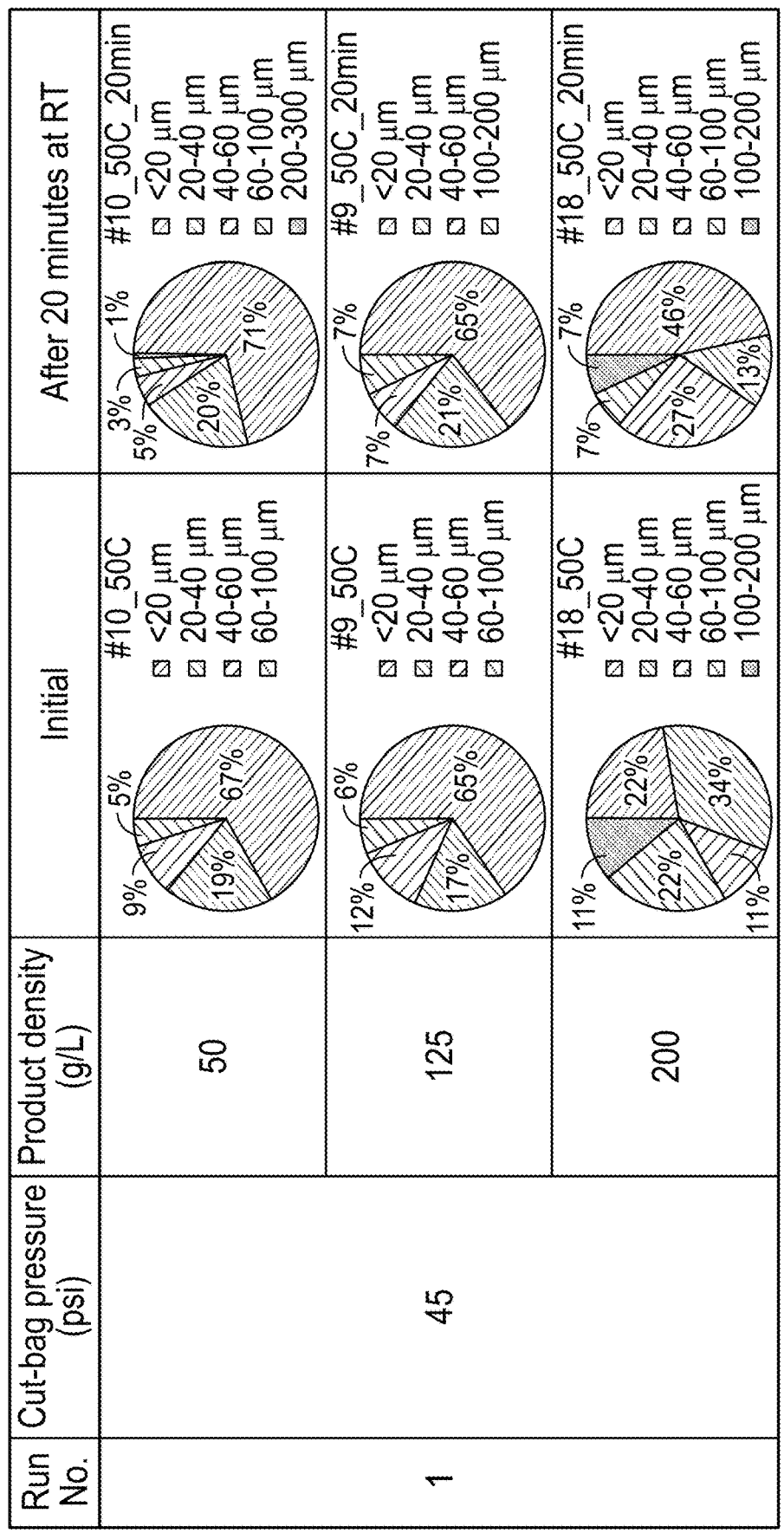
FIG. 27 Distribution of gas bubbles ($N_2O$) in photomicrographs (at 500× magnification) for "whipped-foam" delivered from whipped sunscreen samples (manufactured at cut-bag pressure 45 psi with various product densities), which had been stored at 50° C./75% RH for 1 week.
Figure 27:
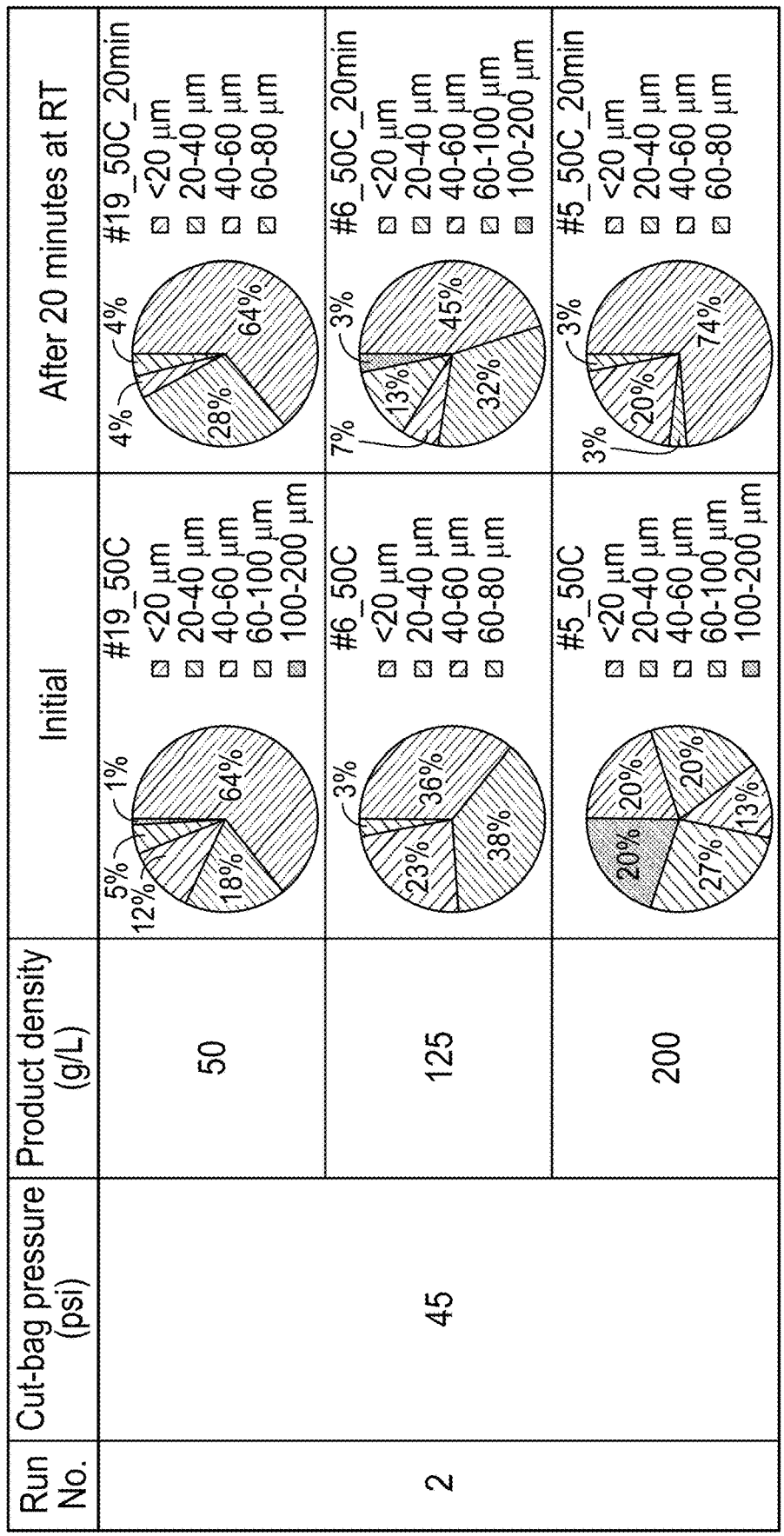

High temperature stability: no significant changes in appearance of "whipped foam", bubble size and distribution at 50° C. (FIG. 7).

Changes in cut-bag pressure have minimal effect on "whipped foam" characteristics.

Both the bubble density (FIG. 8) and number of bubbles (FIG. 8) in each density/cut bag pressure variable sampled showed: Increases in bubble density/bubble number at low product density and low cut bag pressure; Decreases in bubble density/bubble number at high density and high cut bag pressure. This appears to be the result of the lower density variables containing more entrapped gas and having less external pressure to contain expansion of the bubbles. By contrast, the higher density product contains less gas and is capable of repressing bubble size due to high exerted pressures on the formulation contained within.

In conclusion, a single finished whipped lotion formulation, processed under a variety of conditions, is capable of possessing unique physical (pre-dispensed and post dispensed) characteristics. Furthermore, these characteristics often translate directly into the consumer experience and have been demonstrated to impact perceptible changes in key consumer criteria including auditory experience, skin feel, perception of the physical characteristics of the product, and application.

Fluid Dynamic Analysis

Fluid dynamic of "in can" product (finished product) was evaluated using CT Scan, which produces cross-sectional images (virtual "slices") of specific areas of a scanned object, allowing the user to see inside the object without cutting. Density (g/l) means product density (g/L); Cut Bag Pressure (PSIG) means Cut-bag Pressure (psi). Measured precision: Precision of fluid measurement (or CT number precision) was calculated to be: 1 SD: 0.5 HU; Max range: 2 HU. Results are shown in Table 6.

TABLE 6

| Sample | Mean fluid density [%] | SD | Mean sub-resolution bubble density [%] | SD | Mean visible bubble density [%] | SD | Total bubble count [%] | SD | Mean # of visible bubbles | SD | Max # of bubbles | Density (g/l) | Bag pressure [PSIG] |
|---|---|---|---|---|---|---|---|---|---|---|---|---|---|
| 1 | 69.1 | 5.7 | 28.7 | 5.4 | 2.5 | 0.8 | 31.2 | 5.5 | 19.7 | 4.7 | 30 | 125 | 32.5 |
| 2 | 6.3 | 2.6 | 37.8 | 5.1 | 56.3 | 7.4 | 94.1 | 9.0 | 137.4 | 29.2 | 187 | 50 | 20 |
| 3 | 54.3 | 5.4 | 38.9 | 4 | 7.6 | 1.6 | 46.5 | 4.3 | 103.8 | 32 | 160 | 125 | 20 |
| 4 | 0 | 0.02 | 15.1 | 7.4 | 84.9 | 7.4 | 100.0 | 10.5 | 127.6 | 29.2 | 187 | 50 | 32.5 |
| 5 | 80.9 | 4.8 | 19 | 4.2 | 1.3 | 0.9 | 20.3 | 4.3 | 2.3 | 1.6 | 7 | 200 | 45 |
| 6 | 76.2 | 7 | 24 | 6.8 | 1 | 0.6 | 25.0 | 6.8 | 3.6 | 2.9 | 5 | 125 | 45 |
| 7 | 32 | 5.6 | 52.1 | 4 | 17.5 | 3.0 | 69.6 | 5.0 | 141.6 | 36 | 193 | 125 | 20 |
| 8 | 67 | 9.8 | 31.8 | 7.1 | 2.1 | 1.2 | 33.9 | 7.2 | 21.3 | 1 | 56 | 200 | 20 |
| 9 | 78.1 | 5.9 | 22.24 | 5.4 | 1 | 0.8 | 23.2 | 5.5 | 2.8 | 3.1 | 3 | 125 | 45 |
| 10 | 26.4 | 6.3 | 69.6 | 5.2 | 4.3 | 1.9 | 73.9 | 5.5 | 108.7 | 33.9 | 162 | 50 | 45 |
| 11 | 72.4 | 5.4 | 28 | 3.9 | 3.2 | 0.8 | 31.2 | 4.0 | 14 | 5.4 | 30 | 125 | 32.5 |
| 12 | 78.2 | 6.2 | 22.11 | 6.02 | 1.5 | 0.9 | 23.6 | 6.1 | 3.5 | 2.3 | 14 | 200 | 32.5 |
| 13 | 69.6 | 5.7 | 28 | 5.9 | 2.1 | 1.1 | 30.1 | 6.0 | 2.6 | 8.3 | 46 | 200 | 20 |
| 14 | 21.7 | 6.6 | 76.2 | 6.6 | 2.6 | 1.9 | 78.8 | 6.9 | 108.8 | 37 | 138 | 50 | 32.5 |
| 15 | 79.2 | 7.9 | 17.9 | 11.8 | 1.4 | 0.8 | 19.3 | 11.8 | 2.9 | 1.8 | 8 | 200 | 32.5 |
| 16 | 24.3 | 16.7 | 56.8 | 9.7 | 24.3 | 7.4 | 81.1 | 12.2 | 118.8 | 24.7 | 112 |  |  |
| 17 | 59.6 | 6.1 | 38.8 | 5.6 | 2.5 | 1 | 41.1 | 5.7 | 35.8 | 12.3 | 66 | 125 | 32.5 |
| 18 | 80 | 8.4 | 20 | 5.6 | 2.1 | 1 | 22.1 | 5.7 | 3.4 | 3.6 | 8 | 200 | 45 |
| 19 | 20.5 | 5.2 | 72.2 | 4.1 | 7.5 | 3 | 79.7 | 5.1 | 142.3 | 36.1 | 193 | 50 | 45 |
| 20 | 20.9 | 2.1 | 61.9 | 3.4 | 18.9 | 1.5 | 80.8 | 3.7 | 183.4 | 13 | 205 | 50 | 20 | remove sample 4 due to questionable fluid mixture

Table Key $$*\text{Fluid density}[\%]: \frac{\text{non bubble fluid}}{\text{Density}_{fluid}*} = 100 \frac{\overline{\text{Vol}_{non\_bubble\_fluid}}}{\text{Vol}_{all\_fluid}}$$

Note:

$\text{Vol}_{all\_fluid}$ includes total volume of sample within bag

Example 2B

Whipped sunscreen products consisting of a base emulsion formulation (concentrate) and a propellant (gas) are packaged into a pre-pressurized Bag on Valve (BOV) package. The objective of the example is to evaluate the characteristics of whipped sunscreen products manufactured at various process conditions. Formulations details for a whipped sunscreen product used in the following evaluation studies are summarized in Tables 10 and 11. Batches were prepared based on the whipped sunscreen product SPF 50 at various levels of process conditions: three different cut-bag pressures (20, 32.5, and 45 psi) and three different product densities (50, 125, and 200 g/L). See Table 9. The batches tested in the evaluation studies were manufactured and packaged at the intended manufacturing site.

TABLE 7

Composition of Whipped Sunscreen Product (Finished Products)

| Ingredient | SPF 50 Concentration (% w/w) |
|---|---|
| Avicel RC-591 | 2.00 |
| Disodium EDTA | 0.10 |
| Ganex P-904 LC | 0.80 |
| Glycerin | 2.50 |
| Sunspheres PGL | 8.00 |
| Octocrylene | 8.00 |
| Octisalate, USP | 4.50 |
| Homosalate | 10.00 |
| Dicaprylyl Ether | 2.00 |
| Tocopherol | 0.25 |
| Avobenzone | 3.00 |
| Oxybenzone | 6.00 |
| Prolipid 141 | 4.50 |
| Lanette 22 (CM) | 2.00 |
| Cetyl Alcohol | 1.00 |
| Chlorphenesin | 0.27 |
| Sodium Ascorbyl Phosphate | 0.01 |
| Benzyl Alcohol | 0.90 |
| Waterbabies 5235646 | 0.25 |
| Dry-Flo Pure | 4.00 |
| Water | Q.S. |

TABLE 8

Concentrate (Base Formulation): Whipped Sunscreen Lotion Concentrate, Batch Size: 1000 g

| | Concentration (% w/w) | Manufacturing Directions |
|---|---|---|
| Part A Ingredients | | |
| Purified water, USP | 43.77 | Step 1: In a container large enough to hold the entire batch, add the Water of Part A, with rapid mixing, add the Avicel RC-591 of Part A and mix until free from lumps. |
| Avicel RC-591 | 2.00 | |
| Part B Ingredients | | |
| Disodium EDTA | 0.10 | Step 2: Add the ingredients of Part B to the batch of Step 1 and mix until dispersed. Begin heating the aqueous phase to 158-167° F. (70-75° C.) with mixing. |
| Ganex P-904 LC | 0.80 | |
| Glycerin, USP | 2.50 | |
| Sunspheres PGL | 8.00 | |
| Part C Ingredients | | |
| Octocrylene, USP | 8.00 | Step 3: In a separate container, add the ingredients of Part C and heat to 158-167° F. (70-75° C.) with mixing until dissolved. |
| Octisalate, USP | 4.50 | |
| Homosalate, USP | 10.00 | |
| Dicaprylyl Ether | 2.00 | |
| Vitamine E, USP | 0.25 | |
| Avobenzone, USP | 3.00 | Step 4: Add the oil phase of Step 3 to the batch of Step 2 and mix until homogenous. Turn off heat and cool to at least 113° F. (45° C.). |
| Oxybenzone, USP | 6.00 | |
| Prolipid 141 | 4.50 | |
| Lanette 22 (CM) | 2.00 | |
| Cetyl Alcohol, NF | 1.00 | |
| Chlorphenesin | 0.27 | |
| Part D Ingredients | | |
| Sodium Ascorbyl Phosphate | 0.01 | Step 5: Add Part D ingredients to the batch then slowly added the Dry-Flo to the batch and mix well for at least 5 minutes. |
| Benzyl Alcohol, NF | 0.90 | |
| Fragrance | 0.40 | |
| Dry-Flo Pure | 4.00 | |
| Part E Ingredients | | |
| Purified water, USP | Q.S. | Step 6: Q.S. the batch with water of Part E and mix well. Package accordingly. |

TABLE 9

| SAMPLE | CUT BAG PRESSURE (psi) | DENSITY (g/L) |
|---|---|---|
| 170 | NEAT - NO GAS | NEAT - NO GAS |
| 567 | CONTROL | CONTROL |
| 852 | 20 | 50 |
| 819 | 32.5 | 50 |
| 903 | 45 | 50 |
| 33 | 20 | 125 |
| 754 | 32.5 | 125 |
| 90 | 45 | 125 |
| 707 | 20 | 200 |
| 836 | 32.5 | 200 |
| 125 | 45 | 200 |

The results are shown in FIG. 9-27.

Example 7 Sensory Impact Studies

Two intertwined process variables may contribute to controlling the consumer experience associated with a base formulation: gas loading (e.g., Nitrous Oxide), which impacts density, spreadability, sound impact upon expelling from the package, and physical appearance of product; and pre-gas can pressure, which influences stability of gas emulsion, sound, speed of dispense, sputtering, and "quality" characteristics. Sensory impact (such as appearance, sound, and skin impact) to the user of product variants of these two variables were evaluated by trained personnel to determine how product variants are perceived differently by the user, with statistical confidence.

The sensory impact studies were conducted by Sensory Spectrum (222 Oak Ave, Kannapolis, N.C. 28081; 554 Central Ave, New Providence, N.J. 07974). These studies involve skinfeel descriptive analysis of a whipped formulation. Whipped formulations with multiple variables are studied to understand impact of modified manufacturing processes on sensory characteristics of the formulation.

Study Design

Protocol Development

Sensory Spectrum consultants and panel leaders evaluate prototypes, method of dispensing/application and sound upon dispensing to develop a custom protocol for descriptive analysis. The Spectrum Descriptive Analysis Method grounds itself in the use of published and internal intensity reference scales to define intensity boundaries in sensory experiences. Skinfeel panelists are trained using the Spectrum Descriptive Analysis Method for personal care products. They are selected on their ability to detect and discriminate differences in visual and tactile properties. Panelists are trained on a universal scale that focuses on intensity or strength of the signal, coupled with detailed description and definitions of sensory attributes and use of calibrated training samples. All panelists receive a minimum of 100 hours of training and practice prior to commissioning of client research and are extensively trained in evaluation of sprays, creams, and related product forms.

Attribute intensity is rated on a 101-point intensity: scale with 0=none and 100=very strong/very high. The intensity scale uses 1-point increments. Panelists are trained to use the scale in a similar way across panelists and across samples. Use of a universal scale allows attributes to be compared in intensity to one another, (e.g. comparing intensity of slippery feel to intensity of sticky feel), as well as for comparison of samples within and across studies and products having shared attributes.

All evaluations are replicated. Data collection of this type is well suited to correlation with both instrumental and consumer research data. The samples are shown in Tables 6, 8, 9, and 10.

The study design involved monadic assessments of whipped sunscreen formulations in a randomized and balanced complete block design, and estimate mean values for each sensory attribute for each product. A trained panel performed all assessments using the Spectrum Descriptive Analysis Method.

The analyses provide both descriptive (qualitative) and intensity measures (quantitative) of the products. The descriptive analysis methodologies are based on those described in ASTM Manual 26, Sensory Testing Methods, 2nd Ed, E. Chambers IV, editor, and ASTM Manual on Descriptive Analysis Testing for Sensory Evaluation, R. Hootman, editor, and Sensory Evaluation Techniques by Meilgard, Civille and Carr.

Prototype Evaluations—Appearance

Sensory Spectrum consultants evaluated the color of the prototypes (hue, intensity, brightness, opacity) via consensus.

Prototype Evaluations—Sound

Sensory Spectrum's Skinfeel Descriptive analysis panel (minimum of eight panelists) was trained to evaluate the volume and pitch of the perceptible sounds of the prototypes as they were dispensed from their containers. They also assessed the presence/absence of qualitative characteristics of the sound.

Prototype Evaluations—Skinfeel Panel Composition: Eight (8) to eleven (11) trained panelists evaluated the products. All panelists passed an annual validation test.

Test Article Description

The sunscreen test articles/products contain sunscreen ingredients that comply with the types, combinations and concentrations specified by the 1999 FDA Final Sunscreen Monograph or subsequent FDA regulations. All products are over-labeled and bulk packaged and/or over-labeled in their marketed packaging. Products that are not sunscreens may also be tested as benchmarks along with the sunscreen test articles/products.

Test Article Description:

Whipped Sunscreen SPF 50 Lotion; Sunscreen Lotion SPF 50 Non-Whipped.

Procedures

Two 4"×2" rectangular evaluation sites were scribed on each volar forearm. Panelists spread the product within the rectangle with index or middle finger, using a gentle oval motion, at a rate of two strokes per second.

Whipped Product Dispensing Instructions:

Pick up can and with other hand twist actuator noting that the icon moves from the locked position to the unlocked. Place index finger into saddle-shaped curve in actuator in preparation to dispense. Rotate can down at an angle, so that the actuator orifice is positioned close (¼ inch) to the petri dish, in preparation to dispense. Depress actuator and allow product to dispense by building into itself on the petri dish and then slowly pull can up and away. Release the actuator after 2 beats of a metronome set at 120 BPM. NOTE: This amount may be enough to cover a whole appendage (arm, leg, or one side of a torso).

Neat Product Dispensing Instructions:

In a plastic petri dish, the panel leader or technician dispenses the product from a standard bottle in a spiral shape using a nickel size circle, filling it from the edge to the center.

No adverse events were reported.

The study sampling plan used a randomized and balanced complete block design. Nine samples (Tables 6, 8, 9, and 10) were replicated so that each sample was seen twice by each panelist, and one sample was seen three times by each panelist. The average of the replicate evaluations by each panelist was used in the summary analysis for each attribute. Mean and standard deviation for each attribute was analyzed for each sample. SAS was used to conduct this analysis.

Perceptual maps of the samples were developed to better understand the relationships among the attributes that define the sensory space of the sample category tested and where the products fall in that space. This information is used to group samples in homogeneous groups.

Some of the findings are:

Chroma/Intensity (of Color)

Density appeared to provide a directional impact regarding Chroma and Intensity but statistics were not available.

Cracking/Popping

Both Density and Cut Bag Pressure appeared to provide a directional impact regarding Cracking/Popping noise but statistics were not available.

Sputtering

Both Density and Cut Bag Pressure at lower densities appeared to provide a directional impact regarding Sputtering but statistics were not available.

Noise

Density appeared to provide a directional impact regarding Noise but statistics were not available.

Sound

Overall, many of the samples have a low sound impact when dispensed from the packaging. Three samples are moderately loud and high-pitched. One sample makes a crackling/popping sound while two samples sputter when dispensed.

Three Key Dimensions explain 90% of the variability in descriptive profiles of skinfeel. Dimension 1—Oily during rubout with a glossy thick, greasy residue (53% of variability) Dimension 2—Glossy and low in firmness when dispensed (19% of variability). Dimension 3—Visually compact when dispensed into a petri dish (18% of variability).

Prototypes that stand out in Dimension 1 are as follows. Prototype 836 is oily and slow to absorb during rubout, leaves a moderately glossy finish on the skin, and has the highest, thickest residue that is oily & greasy in character. Prototype 567 absorbs quickly, is less glossy, and leaves a thinner residue.

Prototypes that stand out in Dimension 2 are as follows. When dispensed into a petri dish, Prototype 170 is the shiniest among all prototypes for up to 30 seconds. It is also the least firm when manipulated, but it should be noted that this sample was evaluated slightly differently due to its format (neat, not whipped). Prototype 819 is least glossy when dispensed into a petri dish, and is firmest among the whipped prototypes.

Prototypes that stand out in Dimension 3 are as follows. When dispensed into a petri dish, Prototypes 170 and 903 are visually compact and hold their shape. Prototypes 033, 125 & 567 are airier when dispensed and don't hold their shape as well as other prototypes.

Tables 10-16 display some of the data. Attribute intensity is rated on a 101-point intensity: scale with 0=none and 100=very strong/very high.

TABLE 10

Sound Impact

| Sample | Attributes | |
|---|---|---|
| | Volume | Tone |
| 033 | 6.0 CD | 7.0 C |
| 090 | 4.8 D | 4.9 CD |
| 125 | 3.2 E | 3.5 D |
| 170* | n/a | n/a |
| 567 | 6.9 C | 7.2 C |
| 707 | 3.2 E | 3.5 D |
| 754 ** | 4.8 D | 5.6 CD |
| 819 | 41.5 A | 41.2 A |
| 836 | 3.1 E | 3.0 D |
| 852 | 38.1 B | 36.8 B |
| 903 | 40.1 A | 42.6 A |
| p-value | <.0001 | <.0001 |
| lsd | 1.50 | 2.93 |
| sig | ** | ** |

*Lotion format; dispensed via pipette
** Sample was replicated twice for a total of 3 evaluations

TABLE 11

Color Sensory Spectrum consultants evaluated via consensus the color of the prototypes when dispensed into a petri dish.

| | Hue (qualitative) | Chroma | Intensity* (means) | Opacity |
|---|---|---|---|---|
| 033 | yellow | 76.4 | 7.8 | 100.0 |
| 090 | yellow | 63.7 | 10.1 | 100.0 |
| 125 | yellow | 71.6 | 9.2 | 100.0 |
| 170 | yellow | 68.4 | 8.2 | 100.0 |
| 567 | white | 75.6 | 0.0 | 100.0 |
| 707 | yellow | 70.0 | 8.7 | 100.0 |
| 754 | yellow | 70.1 | 8.1 | 100.0 |
| 819 | white | 85.9 | 0.0 | 100.0 |
| 836 | yellow | 74.3 | 6.5 | 100.0 |
| 852 | white | 86.0 | 0.0 | 100.0 |
| 903 | white | 84.7 | 0.0 | 100.0 |

NOTES:
Standard 15-point scale was used for this evaluation
*White is the absence of color, therefore the intensity = 0

TABLE 12

Rubout

| Attributes | 033 | 090 | 125 | 170 | 567 | 707 | 754 |
|---|---|---|---|---|---|---|---|
| Wetness-RO | 52.2 DE | 51.9 E | 56.4 AB | 54.0 CD | 46.8 G | 52.5 DE | 54.8 BC |
| Spreadability-RO | 64.6 DEF | 66.8 BCD | 68.1 ABC | 64.9 DEF | 62.9 FG | 69.3 AB | 67.8 ABC |
| Coolness-RO | 6.1 FG | 8.0 CD | 8.9 BC | 7.5 DE | 6.5 EFG | 10.1 AB | 7.9 CD |
| Thickness-RO | 36.0 BC | 36.4 BC | 36.0 BC | 35.6 C | 34.9 C | 37.5 AB | 35.9 BC |
| Slipperiness-RO | 72.0 D | 75.4 B | 79.9 A | 72.5 CD | 67.9 F | 80.4 A | 74.8 BC |
| Oil-RO | 23.3 DEF | 23.4 DE | 28.0 B | 20.8 EFG | 19.7 G | 27.0 BC | 24.6 CD |

TABLE 12-continued

| | | | Rubout | | | | |
|---|---|---|---|---|---|---|---|
| Wax-RO | 10.1 BCDE | 9.2 CDE | 8.9 DE | 12.4 A | 10.2 ABCD | 8.9 DE | 11.5 AB |
| Grease-RO | 35.3 CD | 38.6 AB | 39.2 AB | 35.2 CD | 33.7 DE | 40.4 A | 36.9 BC |
| Whitening-RO | 18.5 C | 16.9 C | 53.2 B | 14.8 CD | 4.5 E | 52.8 B | 20.8 C |
| Rubs to Absorbency | 53.9 C | 44.5 D | 74.3 B | 35.0 EF | 35.0 EF | 71.5 B | 41.8 DE |

| Attributes | 819 | 836 | 852 | 903 | p-value | lsd | sig |
|---|---|---|---|---|---|---|---|
| Wetness-RO | 48.7 FG | 58.0 A | 53.9 CD | 49.5 F | <.0001 | 1.99 | ** |
| Spreadability-RO | 61.1 G | 70.2 A | 65.5 CDE | 63.1 EFG | <.0001 | 2.55 | ** |
| Coolness-RO | 5.5 G | 10.5 A | 6.9 DEF | 5.9 FG | <.0001 | 1.32 | ** |
| Thickness-RO | 35.6 BC | 39.1 A | 34.7 C | 35.5 C | 0.0003 | 1.83 | ** |
| Slipperiness-RO | 70.2 DEF | 80.7 A | 71.3 DE | 69.2 EF | <.0001 | 2.38 | ** |
| Oil-RO | 21.3 EFG | 31.5 A | 21.8 DEFG | 20.4 FG | <.0001 | 2.95 | ** |
| Wax-RO | 10.0 BCDE | 7.9 E | 10.6 ABCD | 11.4 ABC | 0.0040 | 2.20 | ** |
| Grease-RO | 35.0 CD | 39.8 A | 31.9 E | 35.7 CD | <.0001 | 2.80 | ** |
| Whitening-RO | 7.4 DE | 75.7 A | 5.3 E | 6.6 DE | <.0001 | 8.20 | ** |
| Rubs to Absorbency | 32.4 F | 93.1 A | 33.5 EF | 30.4 F | <.0001 | 8.54 | ** |

Means that share a common letter within an attribute are not statistically significantly different at the indicated CL
** = Significantly different at 95% confidence level
* = Significantly different at 90% confidence level
lsd = Is reported at 95% if p-value < 0.05 and 90% if 0.05 < p-value < 0.10

TABLE 13

| | | | Immediate Afterfeel | | | | |
|---|---|---|---|---|---|---|---|
| Attributes | 033 | 090 | 125 | 170 | 567 | 707 | 754 |
| Gloss-Imm | 21.4 CD | 23.0 C | 34.2 B | 20.6 CDE | 16.0 E | 36.1 B | 22.5 C |
| Whitening-Imm | 2.4 C | 3.0 C | 12.9 B | 2.8 C | 0.7 C | 16.8 B | 3.1 C |
| Tautness-Imm | 15.4 | 15.2 | 15.4 | 15.4 | 15.2 | 15.0 | 15.4 |
| Stickiness-Imm | 8.3 C | 8.6 C | 8.7 C | 8.4 C | 6.2 D | 10.5 B | 9.4 BC |
| Roughness-Imm | 18.2 A | 18.5 A | 18.6 A | 18.7 A | 18.7 A | 18.0 A | 18.4 A |
| Slipperiness-Imm | 67.2 CD | 69.4 BC | 69.5 BC | 69.7 B | 66.3 D | 69.9 B | 70.2 B |
| Thickness of Residue-Imm | 17.5 B | 17.3 B | 18.9 B | 15.1 C | 12.3 E | 19.2 B | 17.6 B |
| Amount of Residue-Imm | 25.5 D | 25.6 D | 29.0 BC | 22.0 E | 17.5 F | 30.0 B | 26.4 CD |
| Oily Intensity-Imm | 14.2 CD | 15.3 CD | 20.8 B | 14.0 CDE | 11.3 E | 20.5 B | 16.3 C |
| Waxy Intensity-Imm | 18.0 | 19.5 | 21.3 | 21.0 | 20.2 | 19.7 | 18.7 |
| Greasy Intensity-Imm | 30.5 CD | 32.3 C | 35.1 AB | 31.7 CD | 26.5 E | 36.6 A | 32.5 BC |
| Silicone Intensity-Imm | 1.1 BCD | 0.9 BCD | 3.0 A | 0.7 BCD | 0.0 D | 1.4 BC | 0.3 CD |
| Plastic/Coated Intensity-Imm | 3.5 A | 2.7 AB | 0.0 D | 2.7 AB | 2.7 AB | 1.8 BC | 1.5 BC |

| Attributes | 819 | 836 | 852 | 903 | p-value | lsd | sig |
|---|---|---|---|---|---|---|---|
| Gloss-Imm | 19.3 CDE | 46.9 A | 17.6 DE | 16.8 DE | <.0001 | 4.63 | ** |
| Whitening-Imm | 1.7 C | 32.9 A | 1.6 C | 2.5 C | <.0001 | 5.22 | ** |
| Tautness-Imm | 15.3 | 15.4 | 15.6 | 15.2 | 0.4690 | — | |
| Stickiness-Imm | 6.5 D | 12.7 A | 8.2 C | 6.0 D | <.0001 | 1.53 | ** |
| Roughness-Imm | 18.8 A | 16.5 B | 19.0 A | 18.8 A | 0.0002 | 1.02 | ** |
| Slipperiness-Imm | 70.1 B | 73.2 A | 70.5 B | 71.5 AB | <.0001 | 2.36 | ** |
| Thickness of Residue-Imm | 12.8 DE | 22.4 A | 14.5 CD | 13.5 CDE | <.0001 | 1.98 | ** |
| Amount of Residue-Imm | 18.4 F | 39.0 A | 19.9 EF | 18.9 F | <.0001 | 2.86 | ** |
| Oily Intensity-Imm | 13.4 DE | 24.8 A | 14.8 CD | 12.8 DE | <.0001 | 2.84 | ** |
| Waxy Intensity-Imm | 22.2 | 18.0 | 19.0 | 21.0 | 0.1774 | — | |
| Greasy Intensity-Imm | 29.4 D | 37.5 A | 30.7 CD | 31.4 CD | <.0001 | 2.74 | ** |

TABLE 13-continued

Immediate Afterfeel

| | | | | | | | |
|---|---|---|---|---|---|---|---|
| Silicone Intensity-Imm | 0.7 BCD | 1.8 AB | 0.5 CD | 0.5 CD | 0.0008 | 1.29 | ** |
| Plastic/Coated Intensity-Imm | 1.8 BC | 0.9 CD | 2.3 ABC | 1.8 BC | 0.0003 | 1.47 | ** |

Means that share a common letter within an attribute are not statistically significantly different at the indicated CL
** = Significantly different at 95% confidence level
* = Significantly different at 90% confidence level
lsd = Is reported at 95% if p-value < 0.05 and 90% if 0.05 < p-value < 0.10

TABLE 14

10-minute Afterfeel

| Attributes | 033 | 090 | 125 | 170 | 567 | 707 | 754 |
|---|---|---|---|---|---|---|---|
| Gloss-10 Min | 14.0 BC | 13.7 BC | 19.1 A | 13.2 BCD | 11.3 D | 17.5 A | 14.4 B |
| Whitening-10 Min | 0.8 C | 1.0 C | 3.6 B | 0.5 C | 0.0 C | 5.5 AB | 0.2 C |
| Tautness-10 Min | 14.5 | 14.9 | 15.1 | 14.8 | 14.9 | 14.4 | 15.0 |
| Stickiness-10 Min | 3.9 CD | 3.5 D | 4.9 BC | 3.0 DE | 2.0 EF | 6.0 B | 3.9 CD |
| Roughness-10 Min | 18.9 | 19.0 | 19.2 | 18.9 | 18.9 | 18.7 | 18.8 |
| Slipperiness-10 Min | 74.4 AB | 73.3 BCD | 72.0 D | 74.3 ABC | 72.9 BCD | 72.3 CD | 74.4 AB |
| Thickness of Residue-10 Min | 11.1 DE | 12.0 CD | 13.4 BC | 9.7 EF | 8.2 G | 13.4 B | 11.6 D |
| Amount of Residue-10 Min | 15.9 CD | 16.9 C | 19.7 B | 14.0 DE | 12.1 EF | 20.0 B | 15.9 CD |
| Oily Intensity-10 Min | 7.8 CDE | 8.3 CD | 12.8 B | 8.1 CD | 5.7 E | 13.9 B | 9.2 C |
| Waxy Intensity-10 Min | 21.4 CD | 23.5 BC | 24.0 BC | 23.7 BC | 23.1 BCD | 23.5 BC | 22.2 CD |
| Greasy Intensity-10 Min | 24.2 CD | 27.0 BC | 26.9 BC | 24.5 CD | 18.6 E | 28.2 B | 26.5 BC |
| Silicone Intensity-10 Min | 0.9 | 1.6 | 1.8 | 2.3 | 2.0 | 1.7 | 1.2 |
| Plastic/Coated Intensity-10 Min | 4.2 A | 2.7 BCD | 1.8 DE | 3.2 ABC | 2.7 BCD | 3.6 AB | 2.1 CDE |

| Attributes | 819 | 836 | 852 | 903 | p-value | lsd | sig |
|---|---|---|---|---|---|---|---|
| Gloss-10 Min | 12.2 BCD | 19.6 A | 12.5 BCD | 11.7 CD | <.0001 | 2.29 | ** |
| Whitening-10 Min | 0.0 C | 6.8 A | 0.5 C | 0.5 C | <.0001 | 1.92 | ** |
| Tautness-10 Min | 15.1 | 15.1 | 14.9 | 14.9 | 0.4953 | — | |
| Stickiness-10 Min | 1.3 F | 7.4 A | 2.9 DE | 1.8 EF | <.0001 | 1.26 | ** |
| Roughness-10 Min | 18.8 | 18.1 | 19.3 | 18.8 | 0.3659 | — | |
| Slipperiness-10 Min | 75.7 A | 74.0 ABC | 74.5 AB | 75.5 A | 0.0049 | 2.02 | ** |
| Thickness of Residue-10 Min | 8.7 FG | 16.2 A | 9.7 EF | 8.4 FG | <.0001 | 1.43 | ** |
| Amount of Residue-10 Min | 11.7 F | 25.0 A | 13.5 EF | 11.6 F | <.0001 | 1.96 | ** |
| Oily Intensity-10 Min | 7.1 CDE | 16.2 A | 9.0 C | 6.1 DE | <.0001 | 2.20 | ** |
| Waxy Intensity-10 Min | 27.8 A | 19.9 D | 25.8 AB | 26.2 AB | 0.0007 | 3.38 | ** |
| Greasy Intensity-10 Min | 23.2 D | 31.6 A | 23.6 D | 22.6 D | <.0001 | 2.85 | ** |
| Silicone Intensity-10 Min | 3.3 | 1.9 | 1.6 | 2.0 | 0.1559 | — | |
| Plastic/Coated Intensity-10 Min | 2.3 CDE | 1.4 E | 2.7 BCD | 2.7 BCD | 0.0006 | 1.20 | ** |

Means that share a common letter within an attribute are not statistically significantly different at the indicated CL
** = Significantly different at 95% confidence level
* = Significantly different at 90% confidence level
lsd = Is reported at 95% if p-value < 0.05 and 90% if 0.05 < p-value < 0.1

TABLE 15

| | Manipulation | | | | | | |
|---|---|---|---|---|---|---|---|
| Attributes | 033 | 090 | 125 | 170 | 567 | 707 | 754 |
| Firmness in Hand/ Firmness | 42.8 B | 41.5 BC | 39.4 D | 31.4 F | 39.1 D | 36.8 E | 36.7 E |
| Stickiness | 29.4 AB | 29.6 A | 28.3 ABC | 25.6 F | 26.7 DEF | 28.6 ABC | 26.4 EF |
| Cohesiveness | 9.3 B | 8.8 BCD | 9.5 B | 11.3 A | 8.3 CDE | 9.2 BC | 8.6 BCDE |
| Peaking | 31.2 B | 27.7 BC | 31.3 B | 38.6 A | 26.0 CD | 31.3 B | 31.4 B |
| Attributes | 819 | 836 | 852 | 903 | p-value | lsd | sig |
| Firmness in Hand/ Firmness | 46.6 A | 36.3 E | 40.3 CD | 40.8 CD | <.0001 | 1.95 | ** |
| Stickiness | 28.1 BCD | 28.4 ABC | 27.7 CDE | 26.3 EF | <.0001 | 1.46 | ** |
| Cohesiveness | 7.8 E | 9.3 B | 9.1 BC | 7.9 DE | <.0001 | 0.94 | ** |
| Peaking | 16.9 F | 26.9 C | 23.1 DE | 20.6 EF | <.0001 | 3.81 | ** |

Means that share a common letter within an attribute are not statistically significantly different at the indicated CL
** = Significantly different at 95% confidence level
* = Significantly different at 90% confidence level
lsd = Is reported at 95% if p-value < 0.05 and 90% if 0.05 < p-value < 0.10

TABLE 16

| | Appearance | | | | | | |
|---|---|---|---|---|---|---|---|
| Attributes | 033 | 090 | 125 | 170 | 567 | 707 | 754 |
| Visual Compactness-Imm | 75.5 EF | 77.5 CDE | 73.2 F | 84.3 A | 73.9 F | 76.3 DEF | 80.4 BC |
| Integrity of Shape-Imm | 81.0 DE | 80.5 DE | 79.1 E | 87.1 A | 78.8 E | 79.2 E | 83.1 CD |
| Gloss-Imm | 80.6 AB | 80.4 AB | 80.1 AB | 81.5 A | 79.7 B | 80.7 AB | 80.6 AB |
| Visual Compactness-10 Sec | 75.4 EF | 77.1 CDE | 73.2 F | 83.9 A | 73.5 F | 76.1 DEF | 80.1 BC |
| Integrity of Shape-10 Sec | 79.5 CD | 78.3 CD | 78.3 CD | 85.5 A | 77.1 D | 78.4 CD | 81.8 BC |
| Gloss-10 Sec | 80.6 AB | 80.4 AB | 80.1 AB | 81.5 A | 79.7 B | 80.7 AB | 80.6 AB |
| Visual Compactness-30 Sec | 75.3 DE | 77.1 CD | 73.4 E | 83.6 A | 73.6 E | 76.0 DE | 80.1 BC |
| Integrity of Shape-30 Sec | 78.4 CD | 77.1 DE | 76.9 DE | 84.5 A | 75.0 EF | 77.4 DE | 80.9 BC |
| Gloss-30 Sec | 80.6 AB | 80.4 AB | 80.1 AB | 81.5 A | 79.7 B | 80.7 AB | 80.6 AB |
| Visual Compactness-60 Sec | 74.8 EF | 77.0 CDE | 72.7 F | 83.3 A | 73.1 F | 75.6 DEF | 80.0 ABC |
| Integrity of Shape-60 Sec | 76.7 C | 76.1 C | 75.3 C | 83.8 AB | 73.8 CD | 76.4 C | 80.5 B |
| Gloss-60 Sec | 80.1 AB | 81.5 A | 80.6 AB | 79.5 BC | 80.7 AB | 80.6 AB | 76.0 D |
| Attributes | 819 | 836 | 852 | 903 | p-value | lsd | sig |
| Visual Compactness-Imm | 81.1 AB | 79.1 BCD | 80.4 BC | 81.5 AB | <.0001 | 3.51 | ** |
| Integrity of Shape-Imm | 83.3 BCD | 73.3 F | 85.7 ABC | 86.5 AB | <.0001 | 3.34 | ** |
| Gloss-Imm | 76.0 D | 80.0 AB | 79.7 B | 78.1 C | <.0001 | 1.48 | ** |
| Visual Compactness-10 Sec | 80.5 AB | 78.9 BCD | 80.1 BC | 81.4 AB | <.0001 | 3.38 | ** |

TABLE 16-continued

| | | | Appearance | | | | |
|---|---|---|---|---|---|---|---|
| Integrity of Shape-10 Sec | 79.0 CD | 72.3 E | 84.1 AB | 85.8 A | <.0001 | 3.51 | ** |
| Gloss-10 Sec | 76.0 D | 80.0 AB | 79.7 B | 78.1 C | <.0001 | 1.48 | ** |
| Visual Compactness-30 Sec | 80.3 ABC | 78.6 BCD | 80.0 BC | 81.3 AB | <.0001 | 3.39 | ** |
| Integrity of Shape-30 Sec | 77.2 DE | 71.6 F | 83.5 AB | 85.3 A | <.0001 | 3.40 | ** |
| Gloss-30 Sec | 76.0 D | 80.0 AB | 79.7 B | 78.1 C | <.0001 | 1.48 | ** |
| Visual Compactness-60 Sec | 80.2 ABC | 78.7 BCD | 79.9 BC | 81.4 AB | <.0001 | 3.40 | ** |
| Integrity of Shape-60 Sec | 76.2 C | 70.8 D | 83.1 AB | 84.8 A | <.0001 | 3.43 | ** |
| Gloss-60 Sec | 80.0 AB | 79.7 B | 80.4 AB | 78.1 C | <.0001 | 1.48 | ** |

Means that share a common letter within an attribute are not statistically significantly different at the indicated CL A summary of the study parameters is below.
As it is Dispensed
 a. Firmness
 b. Stickiness
 c. Integrity of Shape
 d. Peaking
 e. Gloss vs Dull (matte to Shinniness)
 f. Sound
i. During Dispensing
 1. Loudness
 2. Harshness
 3. Whoosh?
 4. Fart sound?
ii. During Pinching for Firmness
 1. Crackling/Popping
 g. Porosity (Dense whip-cream vs Foam, which has large porosity)
 h. Coloration (scale ranging from yellow to white), where white is not a bad thing but indicates amount of gas in product
Rub-Out
 a. Wetness
 b. Spreadability
 c. Thickness
 d. Oil
 e. Wax
 f. Grease
 g. Whitening
 h. Rubs to Absorb
 i. Crackling/Popping as rubbing out
 j. Cooling
 k. Cushioning/Softness
 l. Density of Dollup (volume vs weight)
Afterfeel
 a. Immediate
i. Gloss
ii. Whitening
iii. Stickiness
iv. Thickness of Residue
v. Amount of Residue
vi. Oil
vii. Wax
viii. Grease
ix. Silicone
x. Plastic coated
 b. After 10 minutes
i. Gloss
ii. Whitening
iii. Stickiness
iv. Thickness of Residue
v. Amount of Residue
vi. Oil
vii. Wax
viii. Grease
ix. Silicone
x. Plastic coated Other Embodiments The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A formulation expelled from a pressurized package, the formulation comprising one or more skincare active agents, one or more of which being one or more solid ingredient(s); wherein said formulation is made by:
 (i) blending the formulation comprising an amount of a whipping agent and said one or more skincare active agents; and
 (ii) rapidly mixing said formulation with a series of infusion gas injector ports controlling the whipping agent pressure and rate of flow of the formulation, in a high shear, continuous-flow, high-pressure whipping head, pressurized under controlled temperature, rate of flow, and pressure, saturating the whipping agent into the formulation;
wherein said pressurized package is under sufficient pressure suitable to maintain the whipping agent dispersed in the formulation; and
wherein said pressurized package is under sufficient pressure to expel said formulation as a whipped formulation upon application of external force on said formulation in said package; wherein said whipping agent is nitrogen, nitrous oxide, carbon dioxide, argon, air, oxygen, or a combination thereof; wherein said whipped formulation is a reduced density gas emulsion with a multitude of gas microbubbles continuously distributed throughout the whipped formulation; wherein said one or more solid ingredient(s) are about 10% w/w to about 60% w/w of said formulation.

2. The formulation of claim 1, comprising less than 20% water.

3. The formulation of claim 1, wherein said package is a bag on valve (BOV) pressurized assembly, comprising a two-way fill and dispensing valve, an attached internal high barrier bag affixed to said valve, and rigid container capable of holding positive pressure, affixed to the valve.

4. The formulation of claim 3, wherein said container is glass, barrier resin, metal or alloy, or another material capable of holding positive pressure.

5. The formulation of claim 3, wherein the BOV pressurized assembly dispenses the formulation in a metered dispensing system.

6. The formulation of claim 1, wherein said formulation is readily spreadable and spread evenly after the formulation is expelled from the package.

7. The formulation of claim 1, wherein said solid ingredient comprises zinc oxide.

8. The formulation of claim 7, wherein said zinc oxide is from between about 10% w/w to about 40% w/w of said formulation.

9. A pressurized package comprising a whippable formulation, the formulation one or more of which being one or more solid ingredient(s); wherein said formulation is made by:
  (i) blending the formulation comprising an amount of a whipping agent and said one or more skincare active agents; and
  (ii) rapidly mixing said formulation with a series of infusion gas injector ports controlling the whipping agent pressure and rate of flow of the formulation, in a high shear, continuous-flow, high-pressure whipping head, pressurized under controlled temperature, rate of flow, and pressure, saturating the whipping agent into the formulation;
  wherein said pressurized package is under sufficient pressure suitable to maintain the whipping agent dispersed in the formulation; and
  wherein said pressurized package is under sufficient pressure to expel said formulation as a whipped formulation upon application of external force on said formulation in said package; wherein said whipping agent is nitrogen, nitrous oxide, carbon dioxide, argon, air, oxygen, or a combination thereof; wherein said whipped formulation is a reduced density gas emulsion with a multitude of gas microbubbles continuously distributed throughout the whipped formulation; wherein said one or more solid ingredient(s) are about 10% w/w to about 60% w/w of said formulation.

10. The package of claim 9, wherein said package is a bag on valve (BOV) pressurized assembly, comprising a two-way fill/dispensing valve, an attached internal high barrier bag affixed to said valve, and rigid container capable of holding positive pressure, affixed to the valve.

11. The package of claim 9, wherein said formulation is readily spreadable and spread evenly after the formulation is expelled from the package, after being expelled from the package.

12. The package of claim 9, wherein said solid ingredients, comprises zinc oxide.

13. The package of claim 12, wherein said zinc oxide is from between about 10% w/w to about 40% w/w of said formulation.

14. The package of claim 10, wherein the BOV pressurized assembly dispenses the formulation in a metered dispensing system.

* * * * *